(12) United States Patent
Trout et al.

(10) Patent No.: US 9,205,089 B2
(45) Date of Patent: Dec. 8, 2015

(54) LAYER PROCESSING FOR PHARMACEUTICALS

(75) Inventors: Bernhardt Levy Trout, Lexington, MA (US); Trevor Alan Hatton, Sudbury, MA (US); Emily Chang, Edison, NJ (US); James M B Evans, Sudbury, MA (US); Salvatore Mascia, Boston, MA (US); Won Kim, Gyeonggi-Do (KR); Ryan Richard Slaughter, Riverside, CA (US); Yi Du, Union Township, NJ (US); Himanshu Hemant Dhamankar, Cambridge, MA (US); Keith M. Forward, Somerville, MA (US); Gregory C. Rutledge, Newton, MA (US); Mao Wang, Belmont, MA (US); Allan Stuart Myerson, Boston, MA (US); Blair Kathryn Brettmann, Cambridge, MA (US); Nikhil Padhye, Cambridge, MA (US); Jung-Hoon Chun, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 418 days.

(21) Appl. No.: 13/458,222

(22) Filed: Apr. 27, 2012

(65) Prior Publication Data

US 2012/0305174 A1 Dec. 6, 2012

Related U.S. Application Data

(60) Provisional application No. 61/535,630, filed on Sep. 16, 2011, provisional application No. 61/480,756, filed on Apr. 29, 2011.

(51) Int. Cl.
*A61K 9/70* (2006.01)
*A61K 31/55* (2006.01)
(Continued)

(52) U.S. Cl.
CPC . *A61K 31/55* (2013.01); *A61J 3/00* (2013.01); *A61K 9/209* (2013.01); *A61K 9/2027* (2013.01);
(Continued)

(58) Field of Classification Search
None
See application file for complete search history.

(56) References Cited

U.S. PATENT DOCUMENTS

| 168,240 A | 9/1875 | Dunton |
|---|---|---|
| 2,836,291 A | 5/1958 | Stroop |

(Continued)

FOREIGN PATENT DOCUMENTS

| EP | 0 651 997 B1 | 10/1998 |
|---|---|---|
| EP | 1 088 787 A1 | 4/2001 |

(Continued)

OTHER PUBLICATIONS

Kim, "Layer Bonding of Solvent-Cast Thin Films for Pharmaceutical Solid Dosage Forms", Sep. 2010, pp. 1-84.*

(Continued)

*Primary Examiner* — Brian Gulledge
(74) *Attorney, Agent, or Firm* — Wolf, Greenfield & Sacks, P.C.

(57) ABSTRACT

Layer processing for pharmaceuticals, and related systems, methods, and articles are generally described. In some embodiments, ingestible pharmaceutical products (e.g., tablets) can be formed by processing one or more layers containing a pharmaceutically active composition. For example, at least one layer containing a pharmaceutically active composition can be manipulated (e.g., folded, rolled, stacked, etc.) such that the average thickness of the product formed by the manipulation is at least about two times the average thickness of the portions of the layer(s) used to form the product. In some embodiments, after the layer is manipulated, it can be processed (e.g., cut, coated, etc.) to form a final product such as, for example, a tablet.

42 Claims, 46 Drawing Sheets

(51) Int. Cl.
*A61K 9/20* (2006.01)
*A61K 9/24* (2006.01)
*A61K 31/165* (2006.01)
*A61K 31/426* (2006.01)
*A61J 3/00* (2006.01)
*A61J 3/06* (2006.01)
*A61J 3/10* (2006.01)

(52) U.S. Cl.
CPC ............ *A61K 31/165* (2013.01); *A61K 31/426* (2013.01); *A61J 3/06* (2013.01); *A61J 3/10* (2013.01); *A61K 9/7007* (2013.01); *Y10T 156/1051* (2015.01)

(56) References Cited

U.S. PATENT DOCUMENTS

| | | |
|---|---|---|
| 3,007,848 A | 11/1961 | Stroop |
| 3,625,214 A | 12/1971 | Higuchi et al. |
| 3,917,251 A | 11/1975 | De Lise et al. |
| 3,917,255 A | 11/1975 | Watrous |
| 4,029,757 A | 6/1977 | Mlodozeniec et al. |
| 4,029,758 A | 6/1977 | Mlodozeniec et al. |
| 4,031,200 A | 6/1977 | Reif |
| 4,069,084 A | 1/1978 | Mlodozeniec et al. |
| 4,069,086 A | 1/1978 | Reif |
| 4,072,551 A | 2/1978 | Dabal et al. |
| 4,083,741 A | 4/1978 | Goldberg |
| 4,126,502 A | 11/1978 | Dabal et al. |
| 4,126,503 A | 11/1978 | Gardner |
| 4,128,444 A | 12/1978 | Mlodozeniec |
| 4,128,445 A * | 12/1978 | Sturzenegger et al. ......... 156/64 |
| 4,165,998 A | 8/1979 | Adams et al. |
| 4,197,289 A | 4/1980 | Lipinsky et al. |
| 4,228,149 A | 10/1980 | Brewer et al. |
| 4,307,555 A | 12/1981 | Mlodozeniec et al. |
| 4,308,250 A | 12/1981 | Griffin et al. |
| 4,322,449 A | 3/1982 | Voss et al. |
| 4,332,789 A | 6/1982 | Mlodozeniec |
| 4,349,531 A | 9/1982 | Mlodozeniec et al. |
| RE31,764 E | 12/1984 | Voss et al. |
| 5,948,430 A | 9/1999 | Zerbe et al. |
| 6,177,096 B1 | 1/2001 | Zerbe et al. |
| 6,284,264 B1 | 9/2001 | Zerbe et al. |
| 6,287,595 B1 | 9/2001 | Loewy et al. |
| 6,303,143 B1 | 10/2001 | Chrai et al. |
| 6,306,428 B1 | 10/2001 | Lehmann et al. |
| 6,449,925 B1 | 9/2002 | Otsu et al. |
| 6,552,024 B1 | 4/2003 | Chen et al. |
| 6,592,887 B2 | 7/2003 | Zerbe et al. |
| 6,655,112 B1 | 12/2003 | Cremer et al. |
| 6,702,894 B2 | 3/2004 | Lee et al. |
| 6,709,671 B2 | 3/2004 | Zerbe et al. |
| 6,783,768 B1 | 8/2004 | Brown et al. |
| 7,008,668 B2 | 3/2006 | Hogan et al. |
| 7,070,656 B2 | 7/2006 | Hogan et al. |
| 7,083,805 B2 | 8/2006 | Begleiter |
| 7,153,538 B2 | 12/2006 | Brown et al. |
| 7,285,303 B2 | 10/2007 | Martin et al. |
| 7,357,891 B2 | 4/2008 | Yang et al. |
| 7,425,292 B2 | 9/2008 | Yang et al. |
| 7,470,397 B2 | 12/2008 | Meathrel et al. |
| 7,666,337 B2 | 2/2010 | Yang et al. |
| 7,727,466 B2 | 6/2010 | Meathrel et al. |
| 7,732,020 B2 | 6/2010 | King et al. |
| 7,824,588 B2 | 11/2010 | Yang et al. |
| RE42,126 E | 2/2011 | Ye et al. |
| 7,897,080 B2 | 3/2011 | Yang et al. |
| 7,910,031 B2 | 3/2011 | Yang et al. |
| 7,910,641 B2 | 3/2011 | Myers |
| 7,972,618 B2 | 7/2011 | Fuisz et al. |
| 8,017,150 B2 | 9/2011 | Yang et al. |
| 8,084,059 B2 | 12/2011 | Edgren et al. |
| 8,388,994 B1 | 3/2013 | Scheer et al. |
| 2002/0032220 A1* | 3/2002 | Al-Ghazawi et al. ......... 514/321 |
| 2002/0068092 A1 | 6/2002 | Bosch et al. |
| 2004/0228919 A1 | 11/2004 | Lundegaard et al. |
| 2005/0158362 A1 | 7/2005 | Wheatley et al. |
| 2005/0180992 A1 | 8/2005 | Belcher et al. |
| 2006/0013869 A1 | 1/2006 | Ignatious et al. |
| 2006/0273279 A1 | 12/2006 | Kaplan et al. |
| 2008/0026040 A1 | 1/2008 | Farr et al. |
| 2008/0075772 A1* | 3/2008 | Solomon et al. ............... 424/464 |
| 2008/0241216 A1 | 10/2008 | Von Falkenhausen et al. |
| 2009/0061496 A1 | 3/2009 | Kuhn et al. |
| 2010/0119583 A1* | 5/2010 | Rosenberg et al. ........... 424/443 |
| 2011/0129510 A1 | 6/2011 | Liebmann et al. |
| 2011/0136669 A1 | 6/2011 | Liebmann et al. |
| 2011/0300626 A1 | 12/2011 | Arinzeh |
| 2012/0309250 A1 | 12/2012 | Velev et al. |

FOREIGN PATENT DOCUMENTS

| | | | |
|---|---|---|---|
| EP | 1 671 612 A2 | 6/2006 | |
| EP | 1 920 768 A1 | 5/2008 | |
| WO | WO 80/01984 A1 | 10/1980 | |
| WO | WO 2005/000264 A1 | 1/2005 | |
| WO | WO 2008/056001 * | 5/2008 | ............... A61K 9/20 |
| WO | WO 2010/002418 * | 1/2010 | ............ A61K 48/00 |
| WO | WO 2010/002418 A2 | 1/2010 | |

OTHER PUBLICATIONS

International Search Report and Written Opinion for Application No. PCT/US2012/035464 mailed Sep. 7, 2012.

Cardell, Study of polymeric film bonding for pharmaceutical applications. Thesis paper. Massachusetts Institute of Technology. Cambridge, Massachusetts. Jun. 2011. 29 pages.

Forward et al., Free surface electrospinning from a wire electrode.. IOP Institute of Physics. Apr. 10-14, 2011. Bangor University, Wales. UK. Abstract presented at Electrostatics 2011. 1 page.

Forward et al., Free surface electrospinning.. IOP Institute of Physics. Electrostatic 2011 meeting presentation. Apr. 10-14, 2011. Bangor University, Wales. UK.. 22 pages.

Revalor et al., Electrospraying active pharmaceutical ingredients. Abstract presented at ISIC 18. 18$^{th}$ International Symposium on Industrial Crystallization. Sep. 13-16, 2011. Zurich, Switzerland. 4 pages.

Cardell, Study of polymeric film bonding for pharmaceutical applications. Thesis paper. Massachusetts Institute of Technology. Cambridge, Massachusetts. Oct. 20, 2011. 29 pages.

Brown, The adhesion between polymers. Annual Review of Materials Science. Aug. 1991. 21(1):463-489. DOI: 10.1146/annurev.ms. 21.080191.002335.

Chen et al., Electrospun magnetic fibrillar polystyrene nanocomposites reinforced with nickel nanoparticles. Macromol Chem Phys. 2010;211:1775-83.

De Gennes, The formation of polymer/polymer junctions. Tribology Series, 7:355-367,1981.

Dong et al., Encapsulation of multiple biological compounds within a single electrospun fiber. Small. Jul. 2009;5(13):1508-12.

Jud et al., Fracture mechanics studies of crack healing and welding of polymers. Journal of Materials Science. Jan. 1, 1981. 16(1):204-210. DOI: 10.1007/BF00552073.

Jud et al., Load transfer through chain molecules after interpenetration at interfaces. Polymer Bulletin. 1979. 1(10):697-707. DOI: 10.1007/BF00255445.

Kausch et al., Polymer interdiffusion. Annual Review of Materials Science. Aug. 1989. 19: 341-77. DOI: 10.1146/annurev.ms.19. 080189.002013.

Klein, The interdiffusion of polymers. Science. Nov. 2, 1990;250(4981):640-6.

Kline et al., Polymer welding relations investigated by a lap shear joint method. Polymer Engineering & Science. Jan. 1988. 28(1):52-57. DOI: 10.1002/pen.760280109 Epub Aug. 25, 2004.

Kunz et al., Initial stages of interdiffusion of PMMA across an interface. Macromolecules. Mar. 25, 1996. 29(7): 2548-54.

(56) References Cited

OTHER PUBLICATIONS

Lee et al., Adhesion of high polymers. i. influence of diffusion, adsorption, and physical state on polymer adhesion. Journal of Polymer Science Part A-2: Polymer Physics. Jul. 1967 5(4):751-60 DOI: 10.1002/pol.1967.160050410. Epub Mar. 10, 2003.

Lee et al., Direct measurement of molecular mobility in actively deformed polymer glasses. Science. Jan. 9, 2009;323(5911):231-4. doi: 10.1126/science.1165995. Epub Nov. 27, 2008.

Lukas et al., Self-organization of jets in electrospinning from a free liquid surface: A generalized approach. Journal of Applied Physics. Apr. 25, 2008. 103:084309. doi: 10.1063/1.2907967.

Nagy et al., Comparison of electrospun and extruded soluplus-based solid dosage forms of improvised dissolution. Journal of Pharmaceutical Sciences. Jan. 2012;101(1):322-32.

Prager et al., The healing process at polymer-polymer interfaces. The journal of chemical physics. Nov. 15, 1981. 75(10):5194-8. DOI:10.1063/1.441871.

Schaber et al., Economic analysis of integrated continuous and batch pharmaceutical manufacturing: a case study. Industrial & Engineering Chemistry Research. Jul. 27, 2011 50(17):10083-92. DOI: 10.1021/ie2006752.

Scholten et al., Electrospray as a tool for drug micro- and nanoparticle patterning. Langmuir. Jun. 7, 2011;27(11):6683-8. doi: 10.1021/la201065n. Epub May 6, 2011.

Sun et al., Preparations, properties and applications of chitosan based nanofibers fabricated by electrospinning. Express Polymer Letters. 2011;5(4):342-61.

Voyutskii et al., The role of diffusion phenomena in polymer-to-polymer adhesion. Journal of Applied Polymer Science. 1963. 7(2):475-491. DOI: 10.1002/app.1963.070070207. Epub Mar. 9, 2003.

Wang et al., A novel controlled release drug delivery system for multiple drugs based on electrospun nanofibers containing nanoparticles. Journal of Pharmaceutical Sciences. May 3, 2010;99(12):4805-11.

Wang et al., A novel method for preparing electrospun fibers with nano-/micro-scale porous structures. Polym Bull. Apr. 2009;63:259-65.

Wang et al., Effect of tethering chemistry of cationic surfactants on clay exfoliation, electrospinning and diameter of PMMA/clay nanocomposite fibers. Polymer 51. 2010:6295-302.

Wang et al., Magnolol entrapped ultra-fine fibrous mats electrospun from poly(ethylene glycol)-b-poly(l-lactide) and in vitro release. Chinese Journal of Polymer Science. Jan. 2011;29(2):173-9.

Wang et al., Production and Characterization of Monodisperse, Carbamazepine Nanocrystals by An Electrospray Technique. Novartis-MIT Center for Continuous Manufacturing and Department of Chemical Engineering. Massachusetts Institute of Technology. Abstract. Submitted May 1, 2011.

Wool et al., A theory crack healing in polymers. Journal of Applied Physics. Oct. 1, 1981. 52(10): 5953-5963. DOI: 10.1063/1.328526.

Xiao et al., Immobilization of zerovalent iron nanoparticles into electrospun polymer nanofibers: Synthesis, characterization, and potential environmental applications. J Phys Chem C. 2009;113(42):18062-8.

\* cited by examiner

Rollers for folding

Multiple Reduction Rollers for Bonding

LAYER PROCESSING FOR PHARMACEUTICALS

RELATED APPLICATIONS

This application claims priority under 35 U.S.C. §119(e) to U.S. Provisional Patent Application Ser. No. 61/480,756, filed Apr. 29, 2011, and entitled "Layer Processing for Pharmaceuticals," and to U.S. Provisional Patent Application Ser. No. 61/535,630, filed Sep. 16, 2011, and entitled "Layer Processing for Pharmaceuticals," each of which is incorporated herein by reference in its entirety for all purposes.

FIELD OF INVENTION

Layer processing for pharmaceuticals, and related systems, methods, and articles are generally described.

BACKGROUND

Pharmaceutical manufacturing involves the development of drug products that effectively deliver pharmaceutically active compositions to patients. During the development of such processes, properties of the formulation including bioavailability, drug loading, appearance, and disintegration profile are generally tailored to the specific needs of the patient to whom the drug will be administered. To date, tablets and capsules are some of the most common oral drug delivery systems because of their low manufacturing cost, acceptable forms, designable disintegration profiles, and portable conveniences. Generally, tablets and capsules are designed with one particular pharmaceutically active composition in mind, and include predetermined pharmacological, stability, and manufacturing properties. When the pharmaceutically active composition is of the wrong size, shape, or bulk density, additional steps such as milling and wet granulation are often employed to ensure content uniformity. Common problems in tablet or capsule manufacturing often include lack of pharmaceutically active composition uniformity, loss of powder during operation, and/or uneven powder flow, all of which unnecessarily increase the manufacturing cost, compromise precision, and extend product development.

Recently, a new drug delivery system, fast dissolving oral films, was developed based on the technology of the transdermal patch. Generally, in such systems, a thin strip is designed to be placed on the patient's tongue, where it can become wet and adhere at the site of application. In many cases, the manufacturing costs of oral films are competitive with those of conventional tablets. Generally, thin film manufacturing can reduce cost due to its solution-based approach and its large surface area, and because solid handling and drying time are reduced. These advantages can be magnified when the pharmaceutically active composition is hard to disperse well in a solid form and/or when the pharmaceutically active composition is difficult to handle, both of which can lead to a reduction in pharmaceutically active composition yield and increased cost.

However, the fast disintegration and rapid lease features of thin-film oral strips tend to limit their application to pharmaceutically active compositions compatible with a fast release profile in the patient's mouth. In addition, thin films can have disadvantages associated with their transport; thin films can be difficult to carry, store, and/or handle because of their fragility and general lack of mechanical robustness.

Accordingly, improved systems and methods for producing ingestible pharmaceutical products would be desirable.

SUMMARY OF THE INVENTION

Systems, methods, and articles related to layer processing for pharmaceuticals are provided. The subject matter of the present invention involves, in some cases, interrelated products, alternative solutions to a particular problem, and/or a plurality of different uses of one or more systems and/or articles.

In one aspect, a method is provided. In some embodiments, the method can be used for manufacturing an article comprising an ingestible pharmaceutical product or a precursor thereof, and can comprise forming a layer comprising a pharmaceutically active composition; and manipulating the layer about an elongated dimension to form the article, wherein an average thickness of the article is at least about two times an average thickness of portions of the layer used to form the article. In some embodiments, polymeric layers can be used for tablet-making.

In another aspect, multiple members comprising a pharmaceutically active composition may be positioned adjacent one another and then bonded together to form an article, such as a tablet or other ingestible pharmaceutical product. Each member may have a surface facing an adjacent member and an opposing surface, facing away from the adjacent member. In some embodiments, both the surface facing the adjacent member and the opposing surface may contain the pharmaceutically active composition. In some embodiments, the number of members may be in excess of three. In some embodiments, the members may be positioned adjacent one another by overlapping portions of a larger layer, such as by folding the larger layer onto itself.

In some embodiments, the method comprises providing a precursor of a pharmaceutically active composition within a fluid; producing a pharmaceutically active composition from the precursor within the fluid; and forming a layer comprising the pharmaceutically active composition from the fluid.

Other advantages and novel features of the present invention will become apparent from the following detailed description of various non-limiting embodiments of the invention when considered in conjunction with the accompanying figures. The features described in the above summary and the following detailed description may be used in any suitable combination, such that it is not a requirement that every embodiment of the invention include every feature or provide every advantage described herein. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
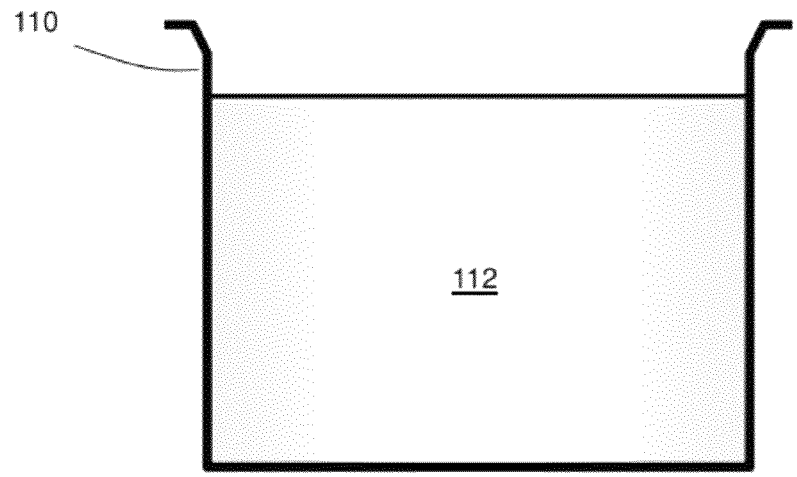
FIGS. 1A-1H include schematic illustrations outlining methods for manipulating layers, according to one set of embodiments.

The inventors have recognized and appreciated that improved quality and/or reduced cost may be achieved for many types of pharmaceutically active compositions through layer processing for pharmaceuticals, and related systems, methods, and articles.

In some embodiments, ingestible pharmaceutical products (e.g., tablets) can be formed by processing one or more layers containing a pharmaceutically active composition. For example, at least one layer containing a pharmaceutically active composition can be manipulated (e.g., folded, rolled, stacked, etc.) such that the average thickness of the product formed by the manipulation is at least about two times the average thickness of the portions of the layer(s) used to form the product. In some embodiments, the layer may be formed as an elongated strip, having an elongated dimension. The manipulation, such as folding or rolling, may be performed about the elongated dimension.

In some embodiments, after the layer is manipulated, it can be processed (e.g., cut, coated, etc.) to form a final product such as, for example, a tablet. As an example, the manipulated layers may be subject to a compressive force such that multiple layers are bonded as part of the pharmaceutical product.

The layer(s) from which the ingestible pharmaceutical product is produced can be formed by depositing a fluid containing the pharmaceutically active composition and/or a precursor thereof. For example, a fluid containing a pharmaceutically active composition and/or precursor can be cast, spin coated, electrodeposited, etc. The layer formed by depositing the fluid can, in some embodiments, may be further processed to form the ingestible pharmaceutical product or a precursor thereof. In some embodiments, the pre-formed pharmaceutically active composition can be combined with a fluid and subsequently incorporated into a layer. In other cases, a precursor of the pharmaceutically active composition can be used to form a pharmaceutically active composition within a fluid, and at least a part of that fluid can be used to form the layer.

Each layer may contain material in addition to the pharmaceutically active composition, such as one or more excipients, including a polymer and/or a plasticizer.

The systems and methods described herein can provide a number of advantages over traditional pharmaceutical product manufacturing techniques. For example, forming final products by manipulating layers (as opposed to, for example, powders) can greatly reduce the cost and complication associated with drying, filtering, and compressing pharmaceutically active compositions. In addition, many pharmaceutically active compositions that are not suitable for use in powder compression processes can be used in layer-based processing. In addition, the systems and methods described herein can achieve uniform mixing, uniform distribution of the pharmaceutically active composition(s), rapid processing, and reproducible product quality. Also, the equipment can occupy a relatively small footprint.

FIGS. 1A-1H include exemplary schematic diagrams illustrating a method for manufacturing an ingestible pharmaceutical product or a precursor thereof, according to one set of embodiments. In the illustrated examples, a fluid is used in forming a layer (or layers) that may then be formed into the pharmaceutical product. In FIG. 1A, a pharmaceutically active composition is provided within fluid 112, which is disposed within container 110. In some embodiments, the pharmaceutically active composition can be dissolved in fluid 112. In other cases, the pharmaceutically active composition can be suspended in fluid 112.

It should be appreciated that regardless of how the pharmaceutically active composition is incorporated into the fluid 112, the pharmaceutically active composition may contain one or more active pharmaceutical ingredients (API).

As described in greater detail below, one or more compounds may be included in fluid 112, as are suitable for forming a layer. Those additional compounds may include a polymer and/or other material that provides a matrix holding the pharmaceutically active composition in the layer, once formed. Fluid 112 may also contain one or more solvents, plasticizers and/or other components that facilitate in handling the fluid or forming the layer with desired properties.

The pharmaceutically active composition can be provided with the fluid via a variety of pathways. In some embodiments, a precursor of the pharmaceutically active composition can be provided within the fluid (e.g., by combining the fluid and the precursor and/or by producing the precursor within the fluid, for example, via a chemical reaction), and the precursor can be used to form a pharmaceutically active composition within the fluid. For example, the precursor can be chemically reacted within the fluid to form the pharmaceutically active composition. In other embodiments, the pharmaceutically active composition can be pre-formed outside the fluid, and the pharmaceutically active composition and the fluid can be combined (e.g., the fluid can be added to the pharmaceutically active composition and/or the pharmaceutically active composition can be added to the fluid).

In some embodiments, fluid 112 can be used to form a layer in any suitable way. For example, the layer may be formed by depositing fluid containing the pharmaceutically active composition. In the set of embodiments illustrated in FIG. 1B, layer 114 has been formed on substrate 115 using fluid 112. In some embodiments, substrate 115 may become a portion of a layer containing pharmaceutically active composition from fluid 112, which may be coated on or impregnated into substrate 115. Though, in other embodiments, a layer may be formed on substrate 115 and then separated from substrate 115 before the layer is used to form a pharmaceutical product. In such embodiments, the substrate may be selected to have properties that facilitate release of the layer or may be coated or otherwise treated to enhance release. The deposited layer, once removed from the substrate may be a self-supporting layer. Such a self-supporting layer may have one or more API's distributed throughout its thickness. For example, the pharmaceutically active compound may be distributed throughout at least 50% of the thickness of the resulting layer.

Layer 114 can include at least a portion of the pharmaceutically active composition contained within fluid 112. Layer 114 can be formed via a variety of methods. In some embodiments, layer 114 can be formed by electro spraying fluid 112 onto a substrate (e.g., substrate 115). Layer 114 can also be formed by electro spinning fluid 112 on a substrate. In some embodiments, layer 114 can be formed by spin coating fluid 112 on a substrate. Layer 114 can also be formed by casting fluid 114 onto a substrate. Each of these methods is described in more detail elsewhere herein.

In some embodiments, after the layer 114 is deposited using fluid 112, layer 114 can be dried. Any suitable method can be used to dry layer 114. In some embodiments, heat can be applied to the layer, for example, directly (e.g., via a heated gas such as ambient air) or indirectly (e.g., by heating the substrate on which the layer is formed). In some embodiments, multiple drying zones can be used to evaporate one or more materials (e.g., solvents) from the layer. Evaporation of the solvents can be partial or complete, depending on the requirements of downstream operations. Drying techniques can be adjusted based on compatibility with the chosen pharmaceutically active composition.

In some embodiments, the thickness of the layer can decrease after the layer has been dried. For example, in some embodiments, drying the layer can decrease the layer thickness by at least about 10%, at least about 25%, at least about 50%, at least about 75%, or more.

Figure 1B:
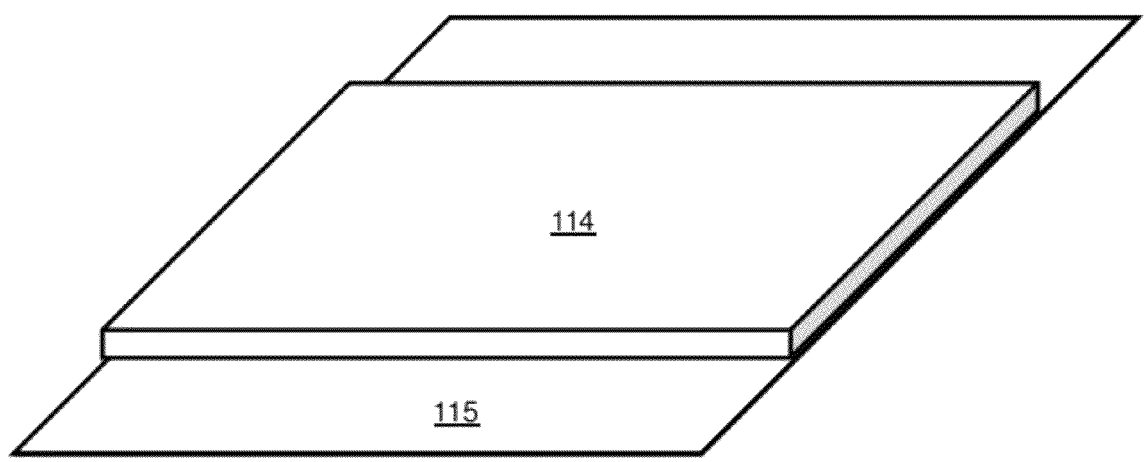

In the embodiment illustrated in FIG. 1B, layer 114 extends across the substrate 115. It should be appreciated that substrate 115 may, but need not, have a size that matches the size of a layer to be formed. In some embodiments, for example, a layer may be formed on a substrate that is elongated in one dimension such that, when the layer is formed on the substrate, the layer will be in the form of an elongated strip. Though, in other embodiments, the substrate may be such that, as liquid is deposited and dried in one region, the dried film may be removed from the substrate in another region. Such a substrate may be constructed as a drum or moving belt, for example. Moreover, it should be appreciated that a layer need not be deposited in the format in which it is used. For example, a layer shaped as an elongated strip may be made by cutting a larger sheet into multiple elongated sheets, each of which can serve as a layer for subsequent processing.

Regardless of the manner in which layer 114 is formed, it can be manipulated to form an article, which can be ingestible pharmaceutical product or a precursor of an ingestible pharmaceutical product. In some embodiments, the layer(s) is manipulated such that at least a portion of a surface of the layer is brought into contact with another portion of that surface or of another surface (of the same layer and/or of another layer). For example, layer 114 can be folded, rolled, stacked, or manipulated in any other suitable manner. These manipulations may be performed about an elongated axis, parallel with an elongated dimension, of the layer. In some embodiments, the article formed by manipulating the layer (alone, or along with another layer) can have an average thickness that is at least about two times, at least about three times, at least about 5 times, at least about 10 times, or at least about 50 times thicker than the average thickness of the portions of the layer(s) used to form the article.

Figure 1C:
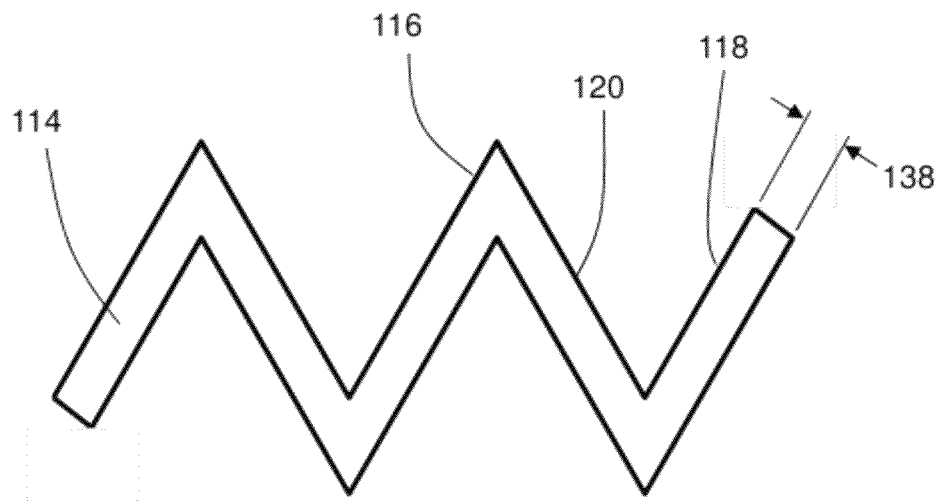

In some embodiments, manipulating the layer comprises folding at least a portion of the layer such that a first portion of a surface of the layer is folded onto a second portion of the same surface. FIG. 1C includes an exemplary cross-sectional schematic illustration of one such process. In FIG. 1C, layer 114 has been removed from substrate 115 and layer 114 is folded to form the folded article 121 in FIG. 1D. Layer 114 includes top surface 116, and first portion 118 of top surface 116 can be folded such that it is in contact with second portion 120 of top surface 116. In some embodiments, portions 118 and 120 can form an interface, such as interface 122 illustrated in FIG. 1D. In addition, in some embodiments, folding a layer as shown in FIG. 1C can produce a crease, such as crease 123 in FIG. 1D. In some embodiments, the folds are parallel to the elongated dimension of the layer.

Figure 1D:
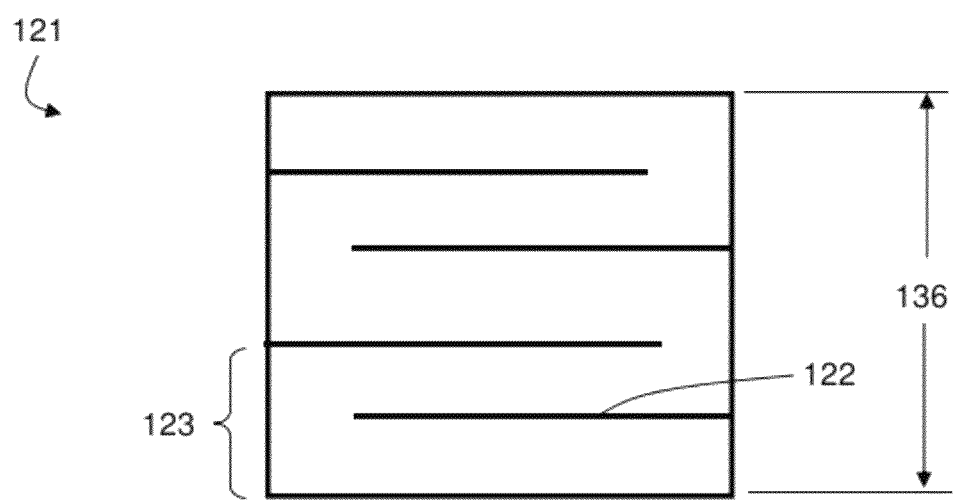

In FIG. 1D, the folds form members comprising a pharmaceutically active composition. In this example, the folding positions those members adjacent one another such that they may then be bonded together to form an article, such as a tablet or other ingestible pharmaceutical product. Each member may have a surface facing an adjacent member and an opposing surface, facing away from the adjacent member. The facing surfaces may be bonded to each other. In some embodiments, including embodiments in which the pharmaceutically active composition is distributed throughout the layer, both the surface facing the adjacent member and the opposing surface may contain the pharmaceutically active composition.

Figure 1E:
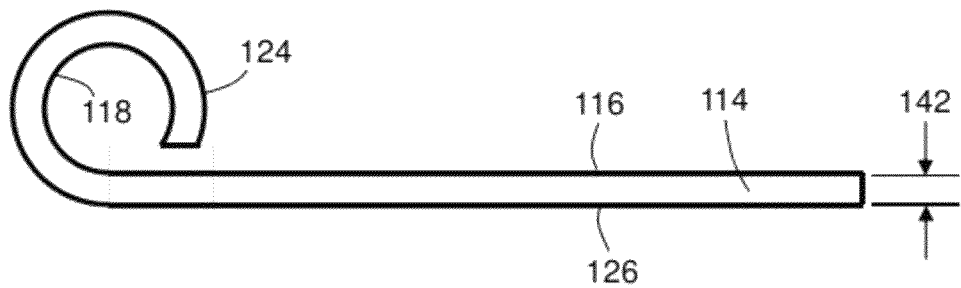
Figure 1F:
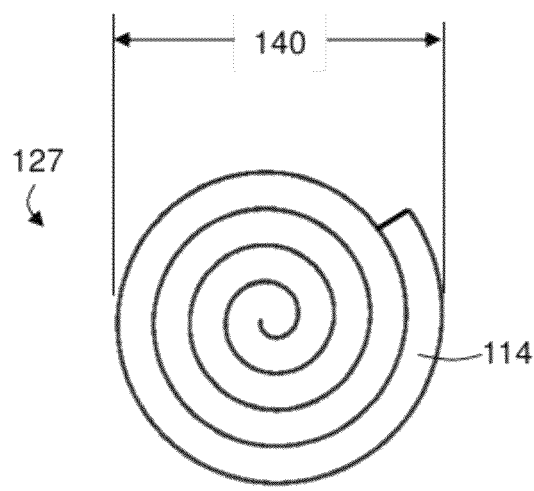
Figure 1G:
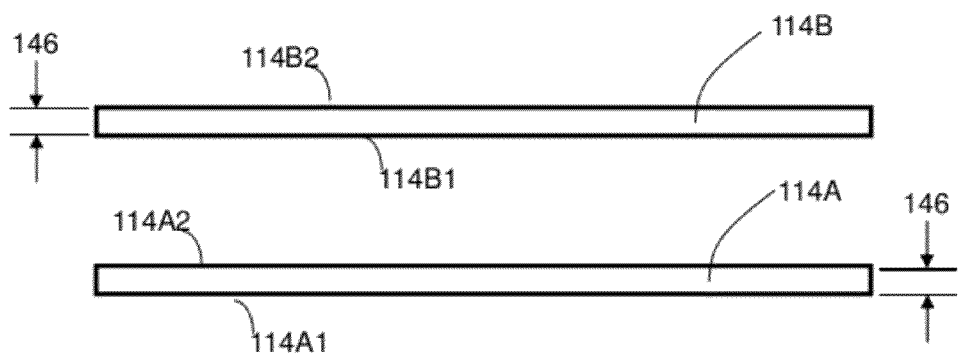
Figure 1H:
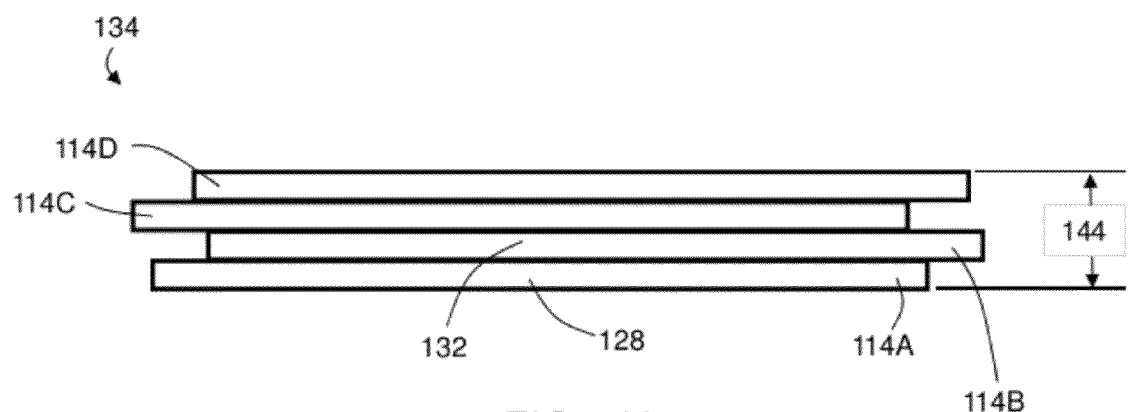

A layer can be manipulated in other ways to form the ingestible pharmaceutical product or a precursor thereof. For example, in some embodiments, manipulating a layer can comprise bringing at least a portion of a first surface into contact with at least a portion of a second, opposite surface. For example, in the set of embodiments illustrated in FIG. 1E, layer 114 includes top surface 116 and bottom surface 126, which is opposite top surface 116. In FIG. 1E, first portion 118 of top surface 116 can be brought into contact with first portion 124 of bottom surface 126. In some embodiments, the layer can be rolled to form, for example, a structure similar to the article 127 illustrated in FIG. 1F.

In some embodiments, the layer may have an elongated axis and the manipulation of the layer may be about the elongated axis. In an embodiment in which the elongated axis of the layer of FIG. 1E is extending out of the plane of the page, FIG. 1E illustrates rolling the layer around its elongated axis.

In still other embodiments, manipulating the layer can comprise stacking at least a portion of the layer on at least a portion of another layer. For example, in the set of embodiments illustrated in FIG. 1G, layers 114A and 114B are provided. Layers 114A and 114B can be formed (e.g., deposited on a substrate) as separate layers, or they can be cut from a single layer to produce separate layers. In the set of embodiments illustrated in FIG. 1H, portion 128 of layer 114A has been stacked on portion 132 of layer 114B. In some embodiments, further layers may be stacked upon layers 114A and 114B. For example, in FIG. 1H, optional layers 114C and 114D have been stacked on top of layers 114A and 114B to form article 134. Any suitable number of layers (e.g., at least 2, at least 3, at least 4, at least 5, at least 10, at least 50, at least 100, or more) can be stacked to form the pharmaceutical product or precursor thereof. In some embodiments, each of the stacked layers may be substantially aligned with the layer below it. In other cases, the layers are not aligned as they are stacked, and suitable alignment can be achieved, for example, via stamping or otherwise cutting the layers to form the article.

Techniques as described herein may result in layers through which a pharmaceutically active composition is dispersed. For example, layers 114A and 114B may contain pharmaceutically active composition through at least about 50% of their thickness. In some embodiments, the pharmaceutically active composition may extend through the layer such that surfaces 114A1 and 114B1 as well as surfaces 114A2 and 114B2 contain the pharmaceutically active composition. As a result, when layers 114A and 114B are positioned adjacent to each other, surfaces 114A2 and 114B1, which are adjacent surfaces, will both contain the pharmaceutically active composition. Though, the opposing surfaces on each layer, surfaces 114A1 and 114B2 in this example may also contain the pharmaceutically active composition. In this way, an article formed from the layer may have the pharmaceutically active composition dispersed throughout its thickness. In embodiments in which it is undesirable for an exterior surface of an article to contain the pharmaceutically active composition, the article may be coated, as is known in the art, or a layer with a different composition may be used to form the outer layers of the article. These approaches may be applicable regardless of the techniques used to form and manipulate the layers.

In some embodiments, one or more layers can be manipulated such that the maximum thickness of the article formed by manipulating the layers (e.g., article 121 in FIG. 1D, article 127 in FIG. 1F, article 134 in FIG. 1H) is at least about two times, at least about three times, at least about 5 times, at least about 10 times, at least about 50 times, between about 2 times and about 1000 times, between about 3 times and about 1000 times, or between about 5 times and about 1000 times the maximum thickness of the portions of the layer(s) used to form the article. In some embodiments, one or more layers can be manipulated such that the average thickness of the article formed by manipulating the layers is at least about two times, at least about three times, at least about 5 times, at least about 10 times, at least about 50 times, between about 2 times and about 1000 times, between about 3 times and about 1000 times, or between about 5 times and about 1000 times the average thickness of the portions of the layer(s) used to form the article.

For example, in the set of embodiments illustrated in FIG. 1D, the thickness of article 121, as illustrated by dimension 136, is about 5 times thicker than the thicknesses of the portions used to form the article, as illustrated by dimension 138. In the set of embodiments illustrated in FIG. 1F, the thickness of article 127, as illustrated by dimension 140 is about 9 times thicker than the thickness of layer 114 (illustrated by dimension 142 in FIG. 1E) used to produce article 127. Finally, in the set of embodiments illustrated in FIG. 1H, the thickness of article 134, as illustrated by dimension 144, is about 4 times thicker than the thicknesses of layers 114A-D (indicated by dimension 146) in FIG. 1G. In some embodiments, the thickness may be based on the number of layers that are bonded to form the article, and any suitable number of layers may be used, including 2 or more. In some embodiments, at least 3 layers will be used. However, the specific number of layers is not critical to the invention.

In some embodiments, after the layer(s) have been manipulated, one or more compressive forces can be applied to the layer(s). Application of force can reduce or eliminate voids within the assembled layer(s). Alternatively or additionally, application of compressive force may aid in bonding adjacent portions of the layer into a unitary structure. In some embodiments, application of force can produce a final product with a density that falls within a desirable range. Force can be applied along more than one direction. For example, in some embodiments, a first compressive force can be applied along a first direction and a second compressive force can be applied along a second direction (e.g., orthogonal to the first direction). In addition, in some embodiments, a third force can be applied along a third direction, which can be different from the first two directions (e.g., orthogonal to the first and second directions). Any suitable force application steps can be applied in any suitable number of directions to achieve desirable properties within the final product. The effect of pressure and impact of controlling it in context to thin-polymeric-films is discussed in more detail below. In addition, a multiple roller-reduction strategy to achieve this in continuous mode may be used. Though, in other embodiments, compressive forces may be applied by a ram that enters a canister the layers holding the layers to be compressed. Accordingly, it should be appreciated that the compressive force may be applied to the layers using any suitable equipment.

In some embodiments, at least one of the compression steps can comprise applying a compressive force defining a pressure of between about 10 MPa and about 50 MPa, between about 20 MPa and about 45 MPa, between about 35 MPa and about 40 MPa, or about 37.5 MPa for a period of time. In some embodiments, the compressive force can be applied (e.g., including an applied pressure within any of pressure ranges mentioned above) for a period of time of at least about 10 seconds or at least about 30 seconds (e.g., between about 10 seconds and about 10 minutes or between about 30 seconds and about 90 seconds).

In some embodiments, after the layer(s) have been manipulated, further processing can be undertaken to form, for example, a final ingestible pharmaceutical product. For example, in some cases, the manipulated layer(s) can be cut. The layer(s) can be cut using any suitable technique and/or side indentations can be carried out. In some embodiments, the layer(s) can be stamped, for example, to form tablets with predetermined shapes and/or dimensions. In some embodiments, the layer(s) can be sliced using a blade such as, for example, a knife, rotating blade, or any other suitable blade. As one specific example, an article (e.g., ingot) can be cut by forcing it between two rotating circular plates equipped with blades at the edges; the plate edges can contain multiple cavities, each representing half of the tablet such that an entire tablet is formed when the edges of two plates meet. An integrated system design for conversion of thin-polymeric-films into tablets is described in detail below.

In some embodiments, a material can be applied to the manipulated layers, for example, after applying a compressive force(s) and/or after cutting the manipulated layers. For example, in some embodiments, a protective coating, a time release coating, and/or any other suitable coating can be applied after applying a compressive force(s) and/or after cutting.

FIGS. 2A-2D outline various processing steps that can be used to form ingestible pharmaceutical products using the systems and methods described herein. For example, in FIG. 2A, fluid 112 can be deposited on a substrate, and subsequently dried to form layer 214A. Subsequently, multiple layers can be stacked to form stack assembly 210A. Stack assembly 210 can be stamped using punch workpiece 212 to form tablet 216. In this example, punch workpiece 212 also applies a compressive force that bonds the layers. Though, it should be appreciated that it is not a requirement that a stamping operation be used to form layers of the desired shape of an article.

Figure 2A:
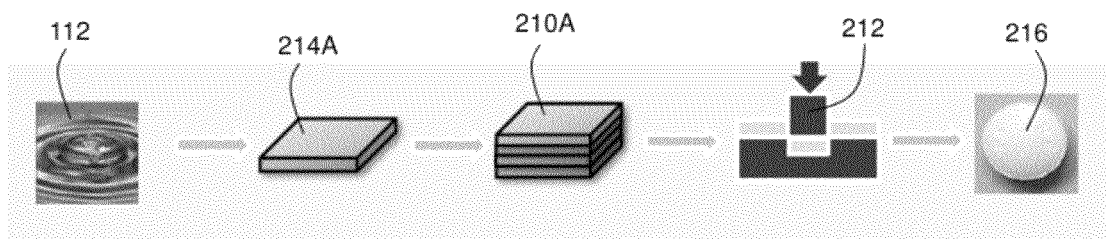
FIGS. 2A-2D include, according to some embodiments, schematic illustrations outlining methods for forming an ingestible pharmaceutical products.

FIG. 2A provides an example of an approach for positioning in parallel multiple planar structures some or all of which may contain a pharmaceutically active composition. Here more than three such planar structures are illustrated. Those planar structures may then be bonded together to form an article. Though, it should be appreciated that other approaches for disposing such planar structures in parallel may be used, including as illustrated in FIG. 2B and FIG. 3.

Figure 2B:
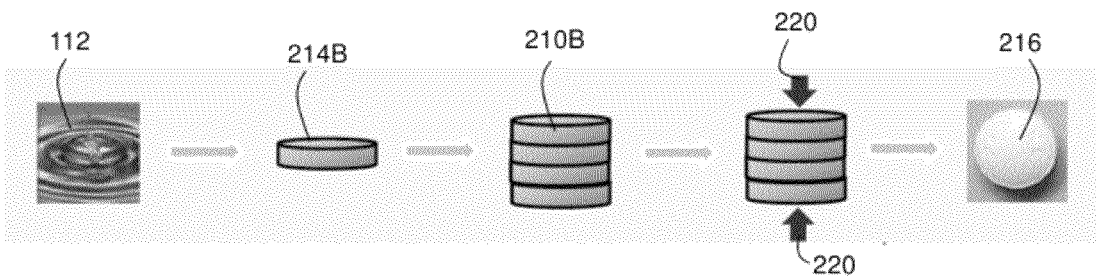
Figure 3:
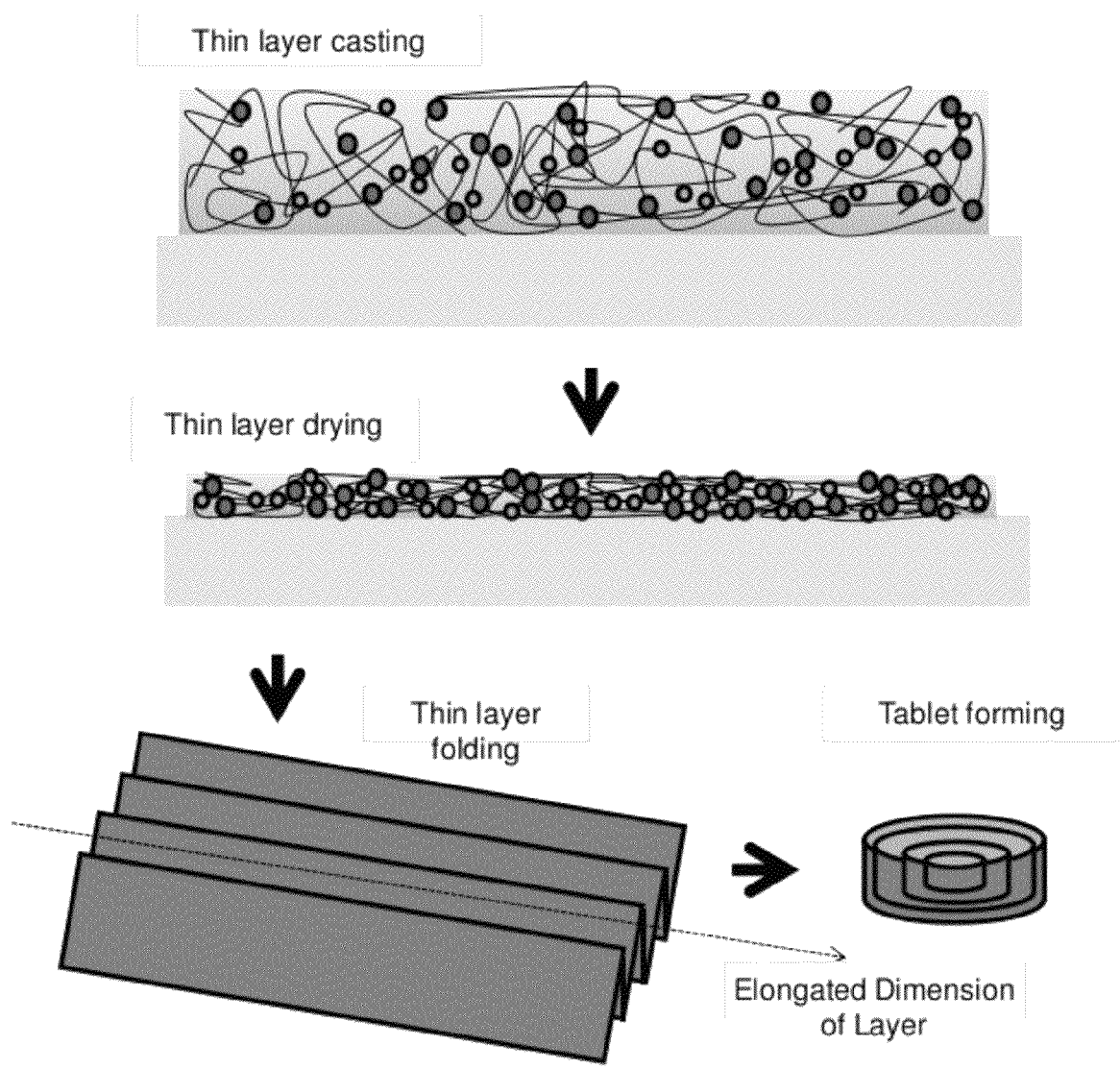
FIG. 3 includes an exemplary schematic outlining pharmaceutical thin layer casting, drying, folding and forming into tablets.

FIG. 2B provides an example in which layers are formed in a desired shape without stamping. In FIG. 2B, fluid 112 can be deposited on a substrate, and subsequently dried to form a layer 214B that is substantially the same length and width as the tablet to be formed. Multiple layers similar in size to that of 214B can be stacked to form stack assembly 210B. One or more forces (indicated by arrows 220) can be applied to compress stack assembly 210B and form tablet 216.

Figure 2C:
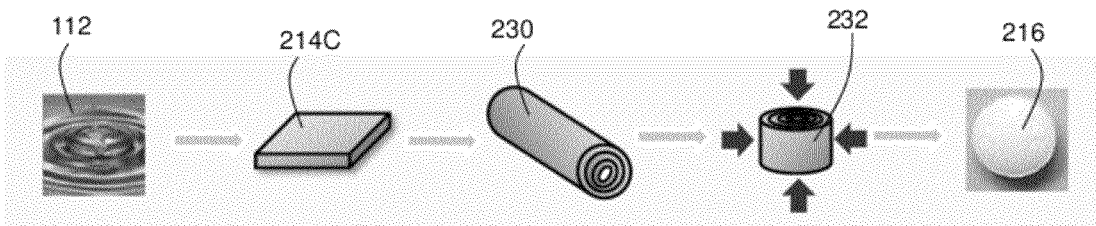

In the embodiment of FIG. 2C, fluid 112 can be deposited on a substrate to form layer 214C, which can subsequently be manipulated to form roll 230. In some embodiments, roll portion 232 (which can include all of roll 230 or a portion cut from roll 230) can be compressed by applying one or more forces to form tablet 216.

Figure 2D:
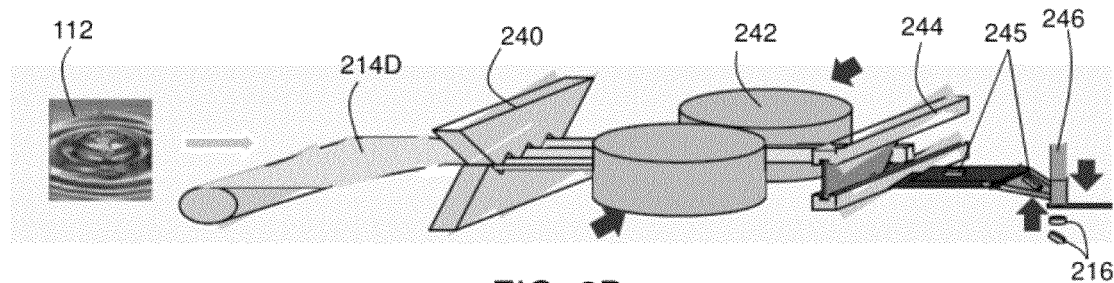

In yet another embodiment, FIG. 2D includes a schematic illustration of a system that can be used to substantially continuously produce tablets or other pharmaceutical products from a fluid containing a pharmaceutically active composition. In FIG. 2D, fluid 112 can be deposited to form a layer arranged as a roll 214D, which can be fed (e.g., continuously) to folding apparatus 240. Folding apparatus can be used to manipulate, such as by folding, the layer in any suitable pattern including, for example, the pattern illustrated in FIG. 1C. After the layer has been folded, it can be passed to compression apparatus 242, which can be used to compress the folded layer.

In this embodiment, compression is being used to bond the portions of the layer that have been formed by folding the layer being played off roll 214D. Though, it should be appreciated that continuous manufacturing operations may be constructed using other bonding techniques. It should also be appreciated that the manipulation and bonding of the layer need not be performed on the entire layer at once. As can be seen, the manipulation occurs on the layer as it is being played off the roll. Bonding occurs on a portion of the layer that has already been manipulated.

In the set of embodiments illustrated in FIG. 2D, compression apparatus 242 includes two cylinders that are rotated as the layer is passed (e.g., continuously) between them. Other suitable compression methods can also be used. The compressed layer can be transported (e.g., continuously) to cutting apparatus 244, which can be used to cut off portions 245 from the folded and compressed layer. In FIG. 2D, cutting apparatus 244 includes a blade that slices off portions of the compressed and folded layer. In other embodiments, other cutting machines (e.g., those employing rotatable blades) can be employed. In FIG. 2D, portions 245 can be fed to a stamping apparatus 246, where they are used to form tablets 216. While continuous operation has been illustrated, in other embodiments, the process can be run intermittently and/or in batches. The working parameters (e.g., pressure, compression rate, and time of pressure application etc.) for these operations can be determined based on mechanical and physical properties of layers.

A variety of ingestible pharmaceutical products can be formed using the systems and methods described herein. As outlined above, the ingestible pharmaceutical product can be in the form of a tablet. In some embodiments, the systems and methods described herein can be used to make sheets, ingots, or other relatively large-scale products from which other pharmaceutical products, such as tablets, can be formed.

A variety of pharmaceutically active compositions can be used in association with the systems and methods described herein. A pharmaceutically active composition may be any bioactive composition. In some embodiments, the pharmaceutically active composition may be selected from "Approved Drug Products with Therapeutic Equivalence and Evaluations," published by the United States Food and Drug Administration (F.D.A.) (the "Orange Book").

In some embodiments, the pharmaceutically active composition can be a small molecule. The term "small molecule" is art-recognized and refers to a composition which has a molecular weight of less than about 2000 g/mole, or less than about 1000 g/mole, and even less than about 500 g/mole. Small molecules may include, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be used in any systems, methods, and/or compositions of the invention.

In some embodiments, the pharmaceutically active composition can be amorphous. Examples of some such compositions include, but are not limited to, amorphous forms of Aliskiren, Aliskiren Hemifumarate, Carbamazepine (CBZ), Ibuprofen and its sodium salt, Indomethacin, Chloramphenicol, Acetaminophen, and Ketoprofen. In some embodiments, the pharmaceutically active composition can be crystalline. Exemplary crystalline compositions that can be used in association with the systems and methods described herein include, but are not limited to, crystalline forms of Acetaminophen and Ibuprofen and its sodium salt.

In some embodiments, one or more excipients can be included in the layer. For example, porogeneous and/or disintegrant agents can be included in the layer, for example, to modify dissolution profiles of the pharmaceutically active composition. The excipient can be added to the layer after it is formed and/or the excipient can be combined with the fluid used to form the layer. Exemplary excipients include, but are not limited to, carboxylmethyl cellulose (CMC), a polymer such as hydroxypropyl methylcellulose (HPMC), soluble starch, Lutrol F68/F127 (Poloxamer 188/407; Polyethyl oxide (PEO)-Polypropyl oxide (PPO)), chitosan, KolliCoat IR (BASF, Edison, N.J.), Kollidon SR (BASF, Edison, N.J.), Kollidon VA 64 (BASF, Edison, N.J.), Kollidon 90F (BASF, Edison, N.J.), polyvinyl alcohol, zein, hydroxyl propyl cellulose, starch, pectin, eurdagit, polyacrylic acid, poyl caprolactom/poyl lactic acid, polymethacrylic acid, gelatin, as well as other pharmaceutically acceptable film forming agents and excipients. In some embodiments, excipients are not needed, and the layer(s), the ingestible pharmaceutical product, and/or a precursor of the ingestible pharmaceutical product can be substantially free of excipients.

In some embodiments, one or more plasticizers can be included in the layer. The plasticizers can be added to the layer after it is formed and/or the plasticizers can be combined with the fluid used to form the layer. Exemplary plasticizers include, but are not limited to, polyethylene glycol, eudragit, propylene glycol, glycerol, polyols, and other pharmaceutically acceptable plasticizers. In some embodiments, plasticizers are not needed, and the layer(s), the ingestible pharmaceutical product, and/or a precursor of the ingestible pharmaceutical product can be substantially free of plasticizers. In some embodiments, the layer (and/or the final ingestible product, such as a tablet) can include between about 4 wt % and about 15 wt %, between about 7 wt % and about 11 wt %, between about 8 wt % and about 10 wt %, or about 9 wt % plasticizer. In some embodiments, the layer (and/or the final ingestible product, such as a tablet) can include between about 4 wt % and about 15 wt %, between about 7 wt % and about 11 wt %, between about 8 wt % and about 10 wt %, or about 9 wt % polyethylene glycol. In some embodiments in which the pharmaceutically active composition in the film comprises Aliskiren (SPP), the film can include a slightly lower amount of polyethylene glycol (e.g., between about 4 wt % and about 8 wt %, between about 5 wt % and about 7 wt %, or about 6 wt % polyethylene glycol in the film).

A layer containing the pharmaceutically active composition can have a variety of properties and configurations. In some embodiments, the layer can be a continuous layer, substantially free of discontinuities. In other embodiments, the layer can have one or more discontinuities within its boundaries.

Generally, layers comprising different components are likely to exhibit a wide range of properties. The success of converting a layer into an article (with specific mechanical and physical properties) can depend on operational regimes of the system designed to convert the layer. As discussed in more detail below, there are several ways this can be achieved.

The layer containing the pharmaceutically active composition can be relatively thin. For example, the layer containing the pharmaceutically active composition can be in the form of a thin film. Though, a layer may have any suitable structure, such as a matrix, which may be a polymer matrix, for example. Though, embodiments are described below in which a layer is formed by electrospinning a material containing a pharmaceutically active composition and spraying a pharmaceutically active composition on a mat or other matrix.

In some embodiments, the thickness of the layer can be relatively uniform. For example, in some cases, at least about 75%, at least about 90%, at least about 95%, at least about 99%, or substantially all of the layer has a thickness that is less than about 20%, less than about 10%, less than about 5%, or less than about 1% different than the average thickness of the layer. In these cases, the percentage difference between the thickness of the layer at a given point (t) and the average thickness of the layer ($t_{avg}$) is calculated as:

$$\% \text{ Difference} = \frac{|t - t_{avg}|}{t_{avg}} \quad [1]$$

One of ordinary skill in the art would be capable of measuring the thickness and thickness variability of a thin film using, for example, a micrometer. With respect to polymeric-thin-films, thickness control has been found to directly affect folding, bonding and tablet-shaping operations.

In some embodiments, the layer can have at least one thickness of less than about 10 mm, less than about 1 mm, less than about 500 micrometers, less than about 100, between about 10 microns and about 10 mm, or between about 100 micrometers and about 10 mm prior to drying the layer. In some embodiments, the layer can have an average thickness of less than about 10 mm, less than about 1 mm, less than about 500 micrometers, less than about 100, between about 10 microns and about 10 mm, or between about 100 micrometers and about 10 mm prior to drying the layer. In some embodiments, the layer can have at least one thickness of less than about 1 mm, less than about 500 micrometers, less than about 100, between about 1 micrometer and about 1 mm, or between about 10 micrometers and about 1 mm after drying the layer. In some embodiments, the layer can have an average thickness of less than about 1 mm, less than about 500 micrometers, less than about 100, between about 1 micrometer and about 1 mm, or between about 10 micrometers and about 1 mm after drying the layer.

In some embodiments, the average thickness (and/or the maximum thickness) of a deposited layer including a pharmaceutically active composition can be smaller than the smallest of the dimensions of the layer in the directions orthogonal to the layer thickness (e.g., a width and/or length of the layer measured parallel to the surface of the substrate on which the layer is deposited). For example, in some embodiments, the average thickness (and/or maximum thickness) of the layer can be at least about 5 times, at least about 10 times, or at least about 100 times smaller than the smallest dimension of the layer in the directions orthogonal to the thickness. The average thickness (and/or the maximum thickness) of a deposited layer can have any of the attributes listed above before and/or after it is dried.

In some embodiments, the layer(s) formed from the fluid can have one more beneficial properties. The layer(s) can be relatively elastic, in some embodiments. For example, in some embodiments, the layer(s) can have a relatively low Young's modulus such as, for example, less than about 1000, less than about 250, less than about 50, less than about 25, less than about 10, between about 1 and about 1000, between about 1 and about 250, between about 1 and about 50, between about 1 and about 25 MPa. The layer(s) can have a relatively high yield strength, in some instances. For example, in some embodiments, the layer(s) can have a yield strength of at least about 0.5, at least about 1, at least about 2, at least about 5, between about 0.5 and about 10, or between about 1 and about 10 MPa. In some embodiments, the layer(s) can have a relatively high fracture strain such as, for example, at least about 10%, at least about 25%, at least about 50%, at least about 75%, at least about 100%, between about 10% and about 150%, between about 50% and about 150%, or between about 100% and about 150%. In some embodiments, the layer(s) can have a relatively high fracture stress such as, for example, at least about 1, at least about 2, at least about 5, at least about 10, between about 1 and about 15, between about 2 and about 15, or between about 10 and about 15 MPa.

In some embodiments, the film can have a hardness within a desired range. For example, in some embodiments, the film can have a hardness of between about 25 MPa and about 40 MPa or between 26 MPa and 37.5 MPa. One of ordinary skill in the art would be capable of determining the hardness of a film using, for example, the Oliver-Phar method to calculate hardness using a wedge indenter and force controlling the mode of loading.

In some embodiments (e.g., when a layer (e.g., thin film) exhibits relatively large plastic deformation characteristics, or ideal-plastic flow), the pressure applied during the compression step can be substantially equal to the hardness of the layer (e.g., within 10%, within 5%, within 2%, or within 1% of the hardness of the layer). Applying such a pressure can enhance the degree to which bonding is achieved within the layer, in certain embodiments.

As mentioned above, one or more layers can be formed by electrospraying a fluid. Generally, electrospraying involves atomization of a liquid into a fine spray of charged droplets by the application of a sufficiently strong electric field. The fine spray can produce very smooth and uniform layers formed as the charged particles are attracted to and deposited on an electrically grounded surface.

In some embodiments, one or more layers can be formed by electro spinning a fluid onto a substrate. In this process, an electrical charge is used to draw very fine fibers (e.g., microscale and/or nanoscale fibers) from a liquid that is to be used to form the layer. The spun fibers can be deposited on a substrate to form a layer, which can then be dried and/or cured.

One or more fluid(s) can also be formed, in some embodiments, by spin coating the fluid onto a substrate. In a spin coating process, the fluid is deposited onto a rotatable substrate, and the substrate is rotated at relatively high speeds (e.g., at least 200 RPM, at least 500 RPM, at least 1000 RPM, at least 1500 RPM, or faster). As the substrate is rotated, the fluid is spread across the substrate surface, and can form a relatively even coating. Optionally, the fluid can be cured and/or dried to form a non-fluid layer after the spinning process.

In some embodiments, one or more layers can be formed by casting the fluid onto a substrate. Generally, this process involves passing the fluid through a defined opening with set dimensions (width, thickness). The opening can be created, for example, by positioning a blade such that it is a fixed distance away from the substrate onto which the fluid is to be deposited. In other cases, a blade is not used to define the opening.

In some embodiments, one or more layers can be formed by a combination of two or more of the techniques described herein. For example, in one set of embodiments, a layer can be formed by electro spinning a portion of the layer (e.g., a polymer matrix component of the layer) and spraying another portion of the layer (e.g., a fluid containing an API) to form a combined layer. As another example, in some embodiments, electro spraying and layer casting can be combined to produce uniform nanocrystals in a thin layer matrix.

As one specific example, in some embodiments, two fluids can be used to form one or more layers. The first fluid can contain a solution of a polymer and/or excipients, while the second fluid can contain one or more pharmaceutically active composition(s). The first fluid can be electro spun to provide a mat/thin layer, which can act as the carrier for the pharmaceutically active composition within the second fluid. The pharmaceutically active composition in the second fluid can be introduced to the mat via electro spraying, which can be tuned to produce either amorphous or crystalline material depending on the pharmacological requirements. The electrospun/sprayed system can then be manipulated using any of the systems and methods described herein to form any of the articles described herein.

The following examples are intended to illustrate certain embodiments of the present invention, but do not exemplify the full scope of the invention.

EXAMPLE 1

This example describes a novel process of fabricating pharmaceutical tablets from layers. The systems and methods in this example can lower manufacturing cost by increasing drying speed and reducing solid handling while producing a final product (e.g., a tablet) that can be used in a relatively wide variety of applications. Properties such as mechanical stability, API loading, crystallinity, polymorphism, stability and solubility, among others, were taken into account. APIs, excipients, plasticizers, surfactants and coating chemicals were considered simultaneously in order to alter the mechanical properties, disintegration profiles, and to alter flavor and color of the tablets. Appropriate layer casting and drying steps were developed, and layer folding and tablet forming was performed. To demonstrate the range of applicability of this process, two different types of APIs were studied: an amorphous API (Aliskiren) and a crystalline API (Acetaminophen (also known as Paracetamol)). It should be noted that preparing a solution and casting of films (that contains API) alleviates many (and in some cases all) issues related to non-homogenous distribution of the API; unlike many other and elsewhere reported manufacturing processes where API is deposited through electrodeposition/spraying or fan-folding methods. Moreover, casting solutions can reduce the issues related to online control or inspection of uniform drug-deposition etc. Though, embodiments are not limited to the specific techniques used to form a layer.

Figure 4A:
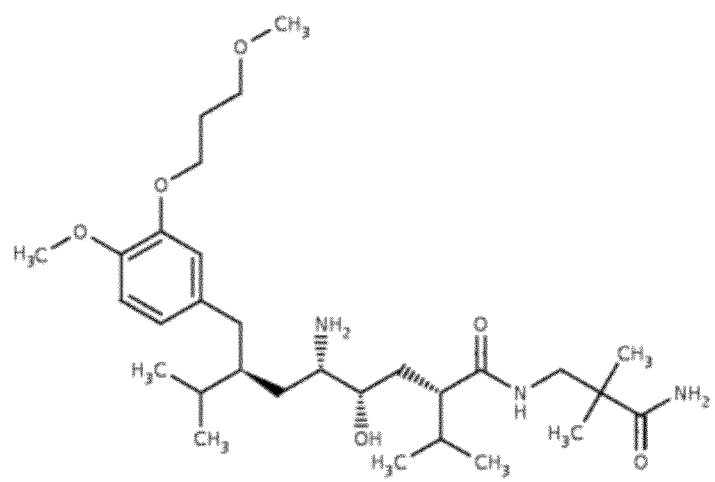
FIGS. 4A-4B include chemical structures of (A) Aliskiren and (B) acetaminophen compounds discussed in Example 1.
Figure 4B:
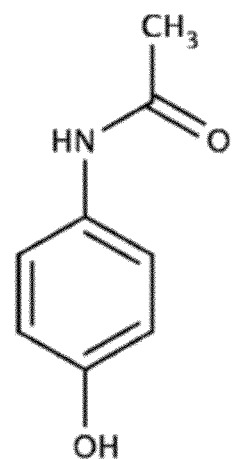

Experimental Section
  Materials:
  METHOCEL E3 and E15 PRM IV (Dow METHOCEL products are methylcellulose and hydroxypropyl methylcellulose (HPMC) rheology modifiers; 2% of E3 or E15 in water has a viscosity of 3 or 15 mPa·s at 20° C.) were supplied from Dow Chemical (Midland, Mich.). The information on average viscosity of the HPMC excipients was provided by the suppliers. Acetaminophen (Paracetamol; Sigma Ultra minimum 99.0%; A7085), Chitosan (low molecular weight; 448899) and Polyethylene glycol 400 (PEG400; P91853) were purchased from Sigma Aldrich. Aliskiren was a model API synthesized and supplied by Novartis, with a purity of 99.63% (determined by HPLC analysis). The chemical structure of Aliskiren and acetaminophen are shown in FIGS. 4A-4B for clarification. KolliCoat IR, Kollidon SR, Kollidon VA 64, Kollidon 90F were provided by BASF in Edison, N.J. Liners (clear polyester secondary non silicone release liner No. 4935 and high density cloudy polyethylene secondary silicone release liner No. 7527L) were provided by 3M in St Paul, Minn. Finally, the casting platform was manufactured using equipment as is known in the art to have the required geometry and dimensions.

Thin Layer Formulation and Casting Solution Preparation
  Aliskiren/HPMC Layer:
  METHOCEL E3 (5 g) and E15 (5 g) were slowly added into ethanol (40 g), under vigorous stirring, to form a homogeneous dispersion. 10 g ALISKIREN was dissolved in 40 g de-ionized (D.I.) water that was then added into the METHOCEL in ethanol dispersion. Subsequently 3.4 g PEG400 was added to the solution to have an API loading (all solid components) of 42.7%. Alternatively, 30 g ALISKIREN and 3.4 g PEG400 were dissolved in 40 g de-ionized (D.I.) water which was then added into the METHOCEL solution to have an API loading (all solid components) of 69.1%. The viscose was degassed by letting it sit under room conditions over night but sealed to avoid evaporation before casting.

Acetaminophen (ACM)/HPMC Layer:
  METHOCEL E3 (5 g) and E15 (5 g) were slowly added into ethanol (40 g), under vigorous stirring, to form a homogeneous dispersion. ACM solutions with concentrations of 1.49 g, 3.35 g, 5.74 g, 8.93 g, 13.4 g, and 20.1 g in 40 g D.I. water were added to METHOCEL/ethanol dispersion to form a mixture solution. 3.4 g of PEG 400 was added to the solutions as a plasticizer. The final ACM content in each case was 10%, 20%, 30%, 40%, 50% and 60% by weight %. The casting solution (viscose) was sealed to avoid evaporation and degassed by letting it sit under ambient conditions over night before casting.

Layer thickness was measured with a caliper and the thickest area measured was chosen to represent the overall thickness. All METHOCEL containing solutions had similar viscosities of about 2800 mPa·s at room temperature at a shear rate 25 s$^{-1}$. The solution viscosity changed significantly by varying the excipient—METHOCEL content. In addition to the excipient content, the METHOCEL E3 and E15 provided by DOW chemical had variations in molecular weight that affected the viscosity batch to batch. The solution viscosity in the studies was with a viscosity distribution up to 20% and it was not significantly affected by varying API type.

ACM or Aliskiren in Kollidon or Kollicoat Layers:
  All Kollidon or KolliCoat products used were very soluble in D.I. water and therefore additional plasticizers were not needed to avoid layer brittleness. The casting solution was prepared by mixing 1:1:8 stoichiometric proportions of excipients:drug:D.I.water. KolliCoat IR solutions had low viscosity (~300 mPa·s) while the KolliDon solutions had much higher viscosities at the same concentration (~2000 mPa·s).

ACM/Chitosan Layer:
  0.33 g chitosan was dispersed into 50 g D.I water with assistance of about 5 ml 99% acetic acid. The resulting solution had a viscosity of about 2000 mPa·s at room temperature under a shear rate 25 s$^{-1}$.

Layer Casting and Drying

For all casting solutions prepared above, two important issues were considered: (i) Film forming ability of the solution; which is largely governed by solution viscosity, and (ii) Coagulation of solution due to improper amounts of components.

A stainless steel casting board was custom made to affix the appropriate liners. The casting board had an edge fixed with aluminum foils to restrict the route of the casting knife. The layer gap could be adjusted in 10 micron intervals from 0 to 6 mm by means of two integrated micrometric screws in the casting knife. The layer gap was fixed to 1.2 mm unless otherwise specified. The dried layer thickness was dictated by the solid content in the starting solution. The dry layer thickness was 0.15±0.02 mm for the 42.7% Aliskiren/HPMC layers, 0.27±0.04 mm for the 69.1% Aliskiren/HPMC layers, and 0.30±0.05 mm in the case of 40% ACM/HPMC layers. The 60% ACM/HPMC layers had a significant thickness distribution from 0.19 to 0.55 mm as there was a clear phase separation between ACM and HPMC in the layers. Different liners were individually tested to optimize the release profile of the thin layer from the liner, as well as to ensure that no significant beading (layer shrinkage during the drying process) occurred. The results showed that both 3M polyethylene secondary silicone release liner and 3M polyester secondary non-silicone release liner were suitable, depending on which pharmaceutical formulation was employed. In order to successfully remove film from the liner, the peel-off energy of the thin-film from the liner can be chosen to be sufficiently lower than the fracture energy of the film. The 3M polyethylene secondary silicone release liner was easier to peel away from the dried layers but beading during the drying process was difficult to avoid with the HPMC/Ethanol/Water system when the solid content was below 30%. The polyester liner performed well regardless of the solid content, but it was significantly harder to peel away the layers from these liners. In this example, layers were dried at 20° C., 50% relative humidity (R.H.) for 3-6 hrs before collection and then sealed under vacuum for storage unless otherwise specified.

Layer Folding, Tablet Forming and Coating

Layers were peeled from the release liner and manually rolled, folded, and compacted into a tablet (300 mg) with dimensions of 4 mm height and 9 mm in diameter. FIG. 3 outlines the manual layer folding and tablet forming process. As can be seen, in this example the layer is folded about across a longitudinal dimension. In another operation, layers were manually peeled-off from the liner and circular discs were cut out using a custom-designed thin-film-cutter and compaction through custom designed die-set.

Tablet forming was done by Instron and a force of up to 25 kN (9 mm diameter die) was recorded. The as-made thin layer tablets are then coated by Opadry AMB for 60 min, with the final coating taking up 10% of the tablet weight. Every 30 tablets were stored in a plastic vial of about 40 ml in volume together with a small standard drying bag. Vials were sealed using aluminum foil and placed at 40° C. for 75% R.H. for 1 month or 3 months. Samples of Aliskiren/HPMC thin layer tablets were tested by HPLC after peeling off the blue coating materials to avoid cross contamination.

Characterization Methods

Scanning electron microscopy (SEM) was performed using a JEOL 6320FV field emission high-resolution SEM at an acceleration voltage of 10 kV. The samples were coated with 15 nm of Au/Pd prior to SEM imaging. Laboratory X-ray powder diffraction (XRD) patterns were recorded using a PANalytical X'Pert Pro diffractometer, fitted with a solid state X'Celerator detector. The diffractometer uses Cu K$\alpha$ radiation ($\lambda(K\alpha1)$=1.5406 Å, $\lambda(K\alpha2)$=1.5433 Å, weighted average $\lambda$=1.5418 Å) and operates in Bragg geometry. Differential scanning calorimetry (DSC) analysis of the layers was carried out using a TA Instruments Q2000 DSC. Samples were analyzed using a heating rate of 10° C./min over the desired temperature range. Moisture content was checked using a MA100 Sartorius moisture analyzer. Water content was measured using a V20 volumetric KF titration from Mettler Toledo. Ethanol content was measured by Agilent headspace gas chromatography (GC); the sample weights (50 mg to 60 mg) were measured precisely and dissolved into 5 ml of HPLC grade water in 20 ml GC headspace vials. ALISKIREN drug purity was verified by Agilent Q1200 series high performance liquid chromatography (HPLC). All analyses were carried out in triplicate. Dissolution testing was performed using a 279 nm UV lamp as the detector.

Tensile tests were performed on a Zwick mechanical tester using the tensile grips with a 500 N Load Cell. A layer strip with dimensions of 5×25 mm, free from air bubbles or physical imperfections, was held between two clamps positioned at a distance of 15 mm Double-sided tape was attached to the surface of the clamp in order to prevent the layer from being cut by the grooves of the clamp. During the measurement, the strips were pulled by the top clamp at a rate of 1.5 mm/min for layers with an elongation smaller than 20%, and 7.5 mm/min for layers with an elongation greater than 20%. The layers were stretched until the layers reached their breaking point. The force and displacement were measured and translated into engineering stress (MPa) and engineering strain (%). Results from layer samples, which broke at and not between the clamps were not included in the calculations. The measurements were repeated five times for each layer.

Thin Layer Casting, Drying and Folding into Tablets

Factors that were considered when forming layers suitable for pharmaceutical product manufacturing include the physico-chemical properties of the drug, as well as optimization of process parameters and conditions. In order to fold and compact the layers into oral tablets, the elasticity and plasticity of the layers were also considered. Additional factors (other than the fact that all materials preferably are GMP-compliant and/or GRAS were also considered as part of this example, including: 1) the excipients and plasticizers, along with the APIs, should be soluble in the volatile solvent and water mixture being used, 2) the excipients and plasticizers should not interact with the API during the thin layer casting/drying/folding process, 3) a stable solution with a reasonable range of solid content and viscosity should be formed to increase flexibility in the thin layer thickness and drug loading, 4) the layer should be homogeneous and should easily release from the casting liners, 5) the pharmaceutical thin layers must have the required tensile strength and plasticity so that they can be handled without substantial deformation and shaped into a tablets without substantial delamination, 6) the final formulation should satisfy pharmaceutical inspection, comprising less than 0.5% of class 2 solvents and less than 0.07% of class 3 solvents, and 7) the tablets should have a disintegration and dissolution profile necessary to meet the requirements for a given API.

A table of requirements and physical connections established for this example are shown in Table 1. In general, the required manufacturing properties include both robust mechanical properties and stable physical and chemical properties of the APIs in the thin layer tablet project. In order to design a formulation, measurable factors such as adhesion and tensile strength properties were included in Table 1, and were used to dictate the choices of excipients, solutions, and manufacturing conditions. For a continuous operation, parameters such as bonding pressure, dwell time and film-passing rate were found to be important in order to successfully transform thin-films into tablets.

TABLE 1

Requirements for thin layer tablet manufacturing and relationships between physical/chemical parameters and properties

| Manufacturing Requirements | Designable and Measurable Parameters | Desirable Properties in Physical Terms | |
|---|---|---|---|
| Thin Film Tablets | Robust Mechanical Properties | Adhesion | Good adhesion but low water content | |
| | | Tensile Strength | Flexible but not elastic | |
| | Stable physical and Chemical Properties | Stability | Compatible and long lasting | |
| | | Hardness | | |
| | | Drying | Simulation and understanding | Feeds back to all other desirable properties in physical terms and designable and measurable properties of hardness and dissolution |
| | | | Optimization - quality and cost | |
| | | Dissolution | | |

As shown from Table 1, the parameters impacted one another. The Manufacturing Requirements impacted Designable and Measurable Parameters, which in turn impacted Desirable Properties in Physical Terms, which in turn impacted Manufacturing Requirements. The simulation and understanding also impacted other desirable properties in physical terms and also impacted designable and measurable properties of hardness and dissolution. Specifically, in this example, the molecular weight of the excipients can greatly influence the viscosity of the solution, the mechanical properties of the layers, and dissolution profile of the tablets. However, it is not always desirable to increase or decrease the viscosity. For instance, a fast dissolving tablet (Aliskiren, etc.) can be produced by using excipients of low molecular weight; however, mechanically robust layers are generally formed using excipients with higher molecular weights. Therefore in some cases, a mixture of different molecular weight excipients can be used to balance the desired properties (METHOCEL E5 and E15, etc.). In addition, it was noted that; 1) changing the solvent types or ratios can largely influence the viscosity of the solutions and the layer drying profile, 2) changing the API loading influences the crystallization kinetics of the API in the layer which in turn influences the mechanical properties of the layer significantly, and 3) the plasticizer and small fast dissolving solids can act as additives to optimize the layer mechanical properties and the tablet dissolution profile relatively independently of other important properties. Later examples related to the design of integrated system include a discussion of how the alterations in properties of films brought through variable compositions within solution are tackled by modifying relevant characteristics in the integrated-system. However, one skilled in the art will recognize that there are many combinations of materials and concentrations that provide viable formulations.

The thermal and mechanical properties of polymers used in forming the layers were evaluated first to determine whether the polymers can serve as layer-forming materials. The choices of solvent mixed with the polymers to form the layers and the appropriate liners were considered to be important factors in obtaining good uniform layers. Layers lacking defects can usually form directly on a glass substrate, due to strong adhesion to the glass which reduces the normal shrinkage of the layer. However, strong adhesion can produce difficulties in peeling the layers off the substrate liners. As noted above, in this example, 3M polyethylene secondary silicone release liner and 3M polyester secondary non-silicone release liner were chosen in balancing adhesion and layer casting.

A variety of film casting and drying methods, including those known to those versed in the art, may be used. As one non-limiting example, high drying efficiency can be a major advantage in using thin layers to produce pharmaceutical products. Transport of solvent molecules in mixtures with polymer excipients and APIs can depend strongly on the solvent concentration. At the initial stage of drying, solvent concentration is high and its diffusion is qualitatively similar to that of simple liquids. As drying proceeds, solvent concentration decreases; polymer excipients and APIs start to form a dense network through which movements of solvent molecules are subject to significant energy barriers. Measurements in polymer-solvent binary systems typically indicate a 3 orders of magnitude or larger decrease in the solvent diffusivity comparing the high and low solvent concentration. For typical thin-layer drying situations, solvent concentration near the interface is lower than that in the bulk, which at the later stage of drying creates a "solidified" layer with much lower diffusivity on top of the layer and seriously impedes the transport of remaining moisture. As reflected in the drying curves, discussed in detail below, the drying rate drops substantially as drying proceeds and it is the last few percent of moisture that limits the total drying time. Efficient heating of the layer may reduce the drying time since solvent diffusion is strongly dependent on the temperature. For the layer thicknesses addressed in this example, heating from the bottom of the layer by a hot-plate can usually keep the layer sufficiently evenly heated. Additional heating from hot air blown onto the top of the layer can be added to "soften" the aforementioned solidified layer. Generally, it is desirable that films with uniform and smooth surfaces are formed, since bonding of films heavily depends upon the surface characteristics.

Conduction heating from the bottom of the liners can be used in some embodiments as it is often sufficient in maintaining a uniform temperature through the layer. Thin layer drying is generally an isothermal process, and the diffusion is driven by the concentration gradient of the solvent molecules. Hot air can also be provided to prevent surface solidification, and it has been proven to increase the evaporation rate. In addition, vacuum drying can efficiently reduce the drying time in this stage. However, in many cases, these measures should be taken with caution: applying either of the two at the early stage of drying can cause significant blister formation in the layer. Phase drying is recommended in an industrial process with conformal drying carried out initially and a forced drying by extra heat, reduced pressure or hot dry air blow to complete the process.

Figure 11:
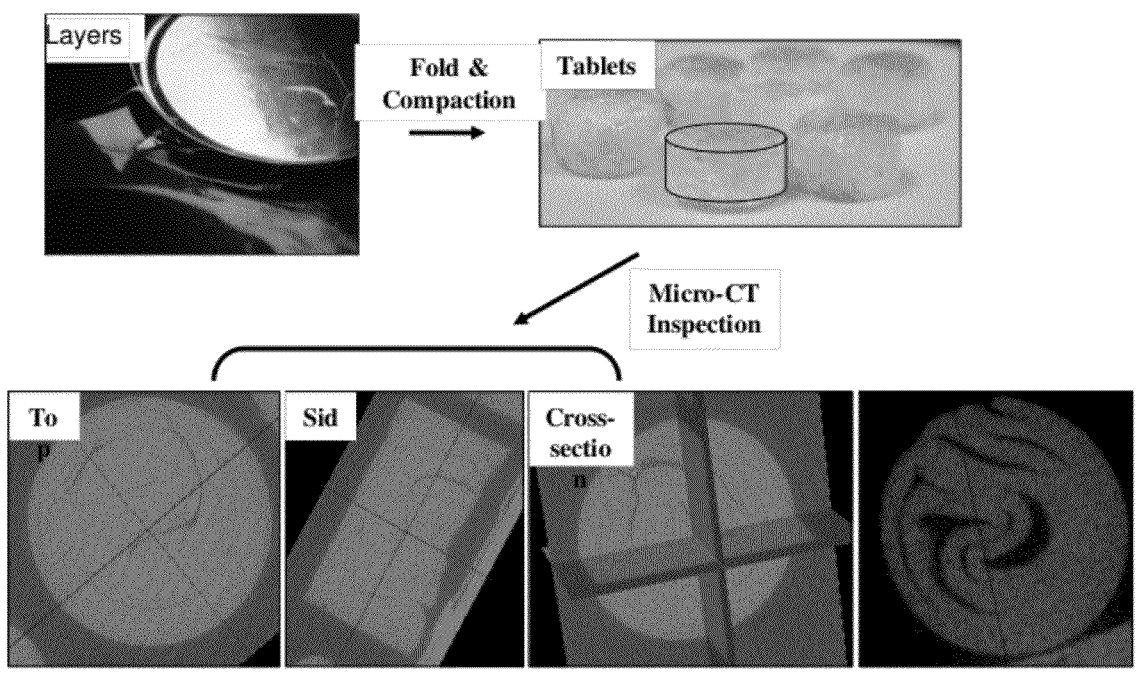
FIG. 11 includes photos of Aliskiren/HPMC layers and tablets made from the layers; with corresponding micro-CT cross-section view for a representative tablet.

Thin layer drying profiles also depend heavily on the APIs. In this example, aliskiren and acetaminophen were used to demonstrate thin layer casting, drying, folding and tablet forming (FIG. 3). API, excipients and plasticizers were mixed in solvent and the resulting viscose was layer-casted onto appropriate liners using a height adjustable casting knife. On average, in this example, the final thicknesses of the layers were ⅛ to ⅐ of the initial casting thickness. Layers were peeled from the liners after drying and stored under vacuum to remove remaining organic solvents and water. An area of approximately 16 cm² of the layer (about 120-150 micrometer thickness) with a mass around 300 mg was cut, folded manually, and compressed twice from different directions to form the final tablet with a diameter of 9 mm and a height of 4 mm. The corresponding layers and tablets produced by the process depicted in FIG. 3 are shown in FIG. 11.

Ten different layer-forming excipients were selected and studied in order to determine their capability to form mechanical robust layers with two APIs: aliskiren and acetaminophen. The excipients studied included: carboxylmethyl cellulose (CMC); hydroxyl propyl methyl cellulose (HPMC; METHOCEL E3 and E5 from Dow Chemical in Midland, Mich.); soluble starch; Lutrol F68/F127 (Poloxamer 188/407; Polyethyl oxide (PEO)-Polypropyl oxide (PPO)); Chitosan; KolliCoat IR; Kollidon 90F+VA64 (PVP), polyvinyl alcohol, and Zein. All of the excipients chosen are reported in the literature to be suitable for pharmaceutical formulations.

It was found that hydroxyl propyl methyl cellulose (HPMC; METHOCEL E3 and E5 from Dow Chemical in Midland, Mich.) was a suitable excipient for these embodiments because it was compatible with both APIs screened in this study and was mechanically robust in both cases. HPMC dried relatively quickly (less than 3 hrs) even at room temperature and with PEG400 (No. 91893 from Sigma Aldrich) as plasticizer, HPMC layers with either API can maintain its mechanical robustness even in the absolute absent of water. HPMC layers can also be easily folded and shaped into tablets. The HPMC system was used to study the formulation and properties relationship and to demonstrate the applicability of thin layer tablets.

Others of the compounds tested were less preferred for the specific example provided herein because of their performance with respect to one or more metrics, such as compatibility with the APIs, viscose solution drying time when casted, and the ability to fold and compact into tablets. Trials showed that carboxylmethyl cellulose (CMC), soluble starch, Lutrol F68/F127 (Poloxamer 188/407; Polyethyl oxide (PEO)-Polypropyl oxide (PPO)) and Zein were less desirable layer forming agents than the HPMC system with the APIs tested in this example. The dried layers produced using these agents were cracked, and further addition of the plasticizers used for this study did not alleviate the brittleness of the layer. The family that include polyvinyl propyl (PVP) mixtures (PVP, Kollidon 90F and 64A), polyvinyl alcohol (PVA) mixtures (PVA, KolliCoat IR (polyvinyl alcohol (PVA)-polyethyl glycol (PEG)) were very good facile layer forming agents, but they were not as good for tablet manufacturing as the HPMC system due to their high resistance to shaping and lack of cohesion in the compositions tested. PVA was also not compatible with acetaminophen. Chitosan was not compatible with aliskiren. In both cases, a cloudy suspension formed right after mixing. PVA was also extremely hygroscopic; meaning that the drying time was significantly higher than for the other excipients and was not used in this example because of experimental efficacy. Soluble starch, Lutrol F68/F127, Zein and KolliCoat IR were thinner than desired for the initial casting viscose for the manufacturing process used in this example. A simple example concerning the compression issues is given in FIG. 24C; even though Kollicoat IR is a good layer forming agent with or without plasticizers, it was not selected for this thin layer tablet study because delamination was observed after compressing into tablets.

Though, it should be appreciated with respect to this example, and the other examples provided herein, that in other contexts materials not selected as the most preferred may nonetheless be suitable. Moreover, in other scenarios, other material selection criteria, such as cost or availability, may be considered such that even materials not preferred in the specific examples given herein may be preferred or even the most preferred materials.

Amorphous Drug (Aliskiren) in Thin Layer Formulations

Figure 5A:
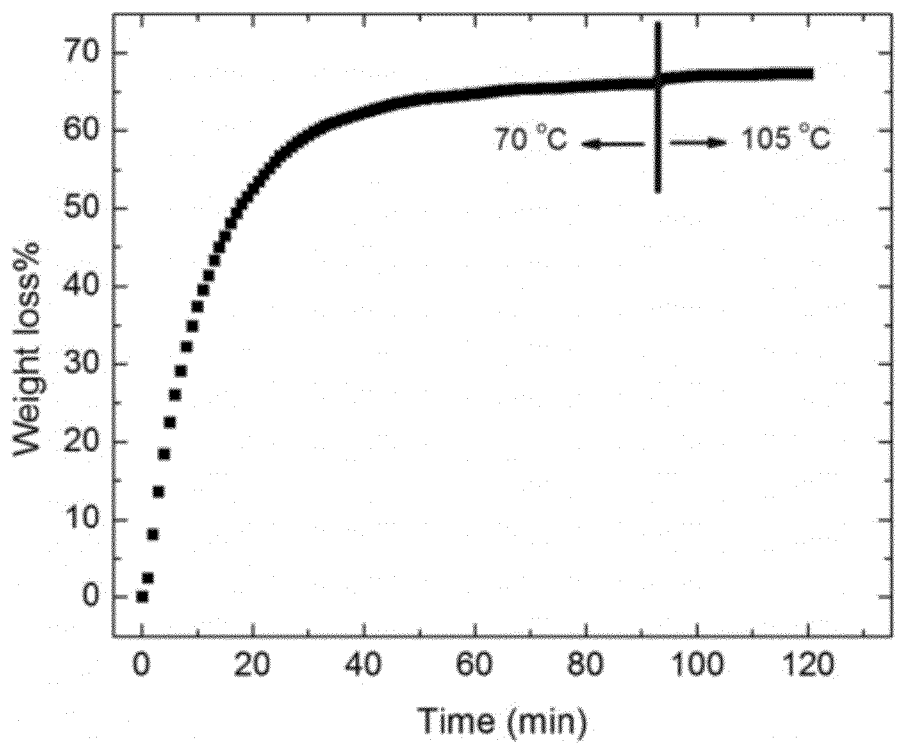
FIGS. 5A-5B include moisture analyzer drying curve data for layer casting of "Aliskiren/HPMC" at (a) moisture %=(weight at time Tx−weight at original)/original weight of sample; and (b) d weight=(weight at time Tn−weight at time Tn+1)/original weight of sample.
Figure 5B:
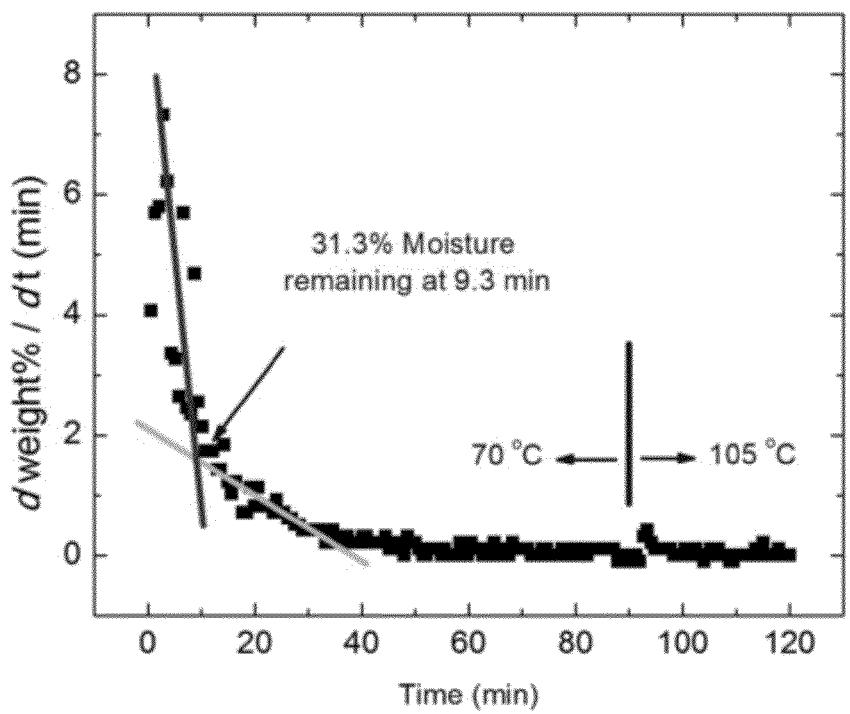

Upon casting 1.2 mm of viscose onto a 25×75 mm glass slide, the weight lost at 70° C. was recorded. Subsequently, the temperature was increased to 105° C. for complete drying on a real time oven balance. A weight loss of approximately 65.95% was observed after 90 min of drying at 70° C.; and a total of 67.30% weight loss was observed by heating to 105° C. for another 30 min (FIG. 5A). The weight loss was likely due to the initial solvent content (68.73%) taking into consideration that some of the solvents (ethanol and water) may have evaporated when the viscose was mixed using a mechanical stirring device before being measured in the moisture analyzer. By plotting the derivative of the drying curve, FIG. 5B, it is evident that drying rates at high and low moisture levels were different: fast drying was observed when the moisture % was above approximately 30%, after which a much lower drying rate was observed.

Figure 6:
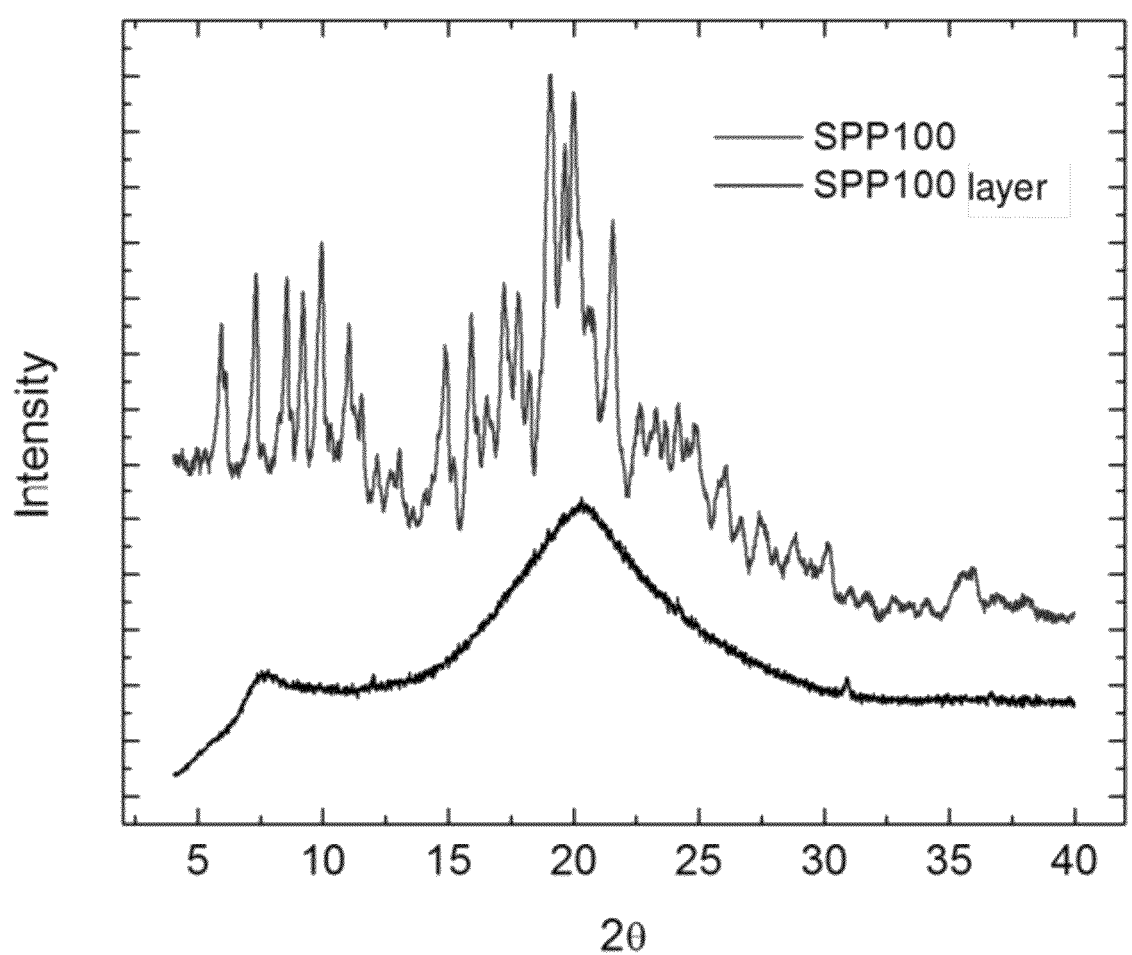
FIG. 6 includes XRD patterns of an amorphous Aliskiren/HPMC layer and a crystalline Aliskiren drug substance.
Figure 7:
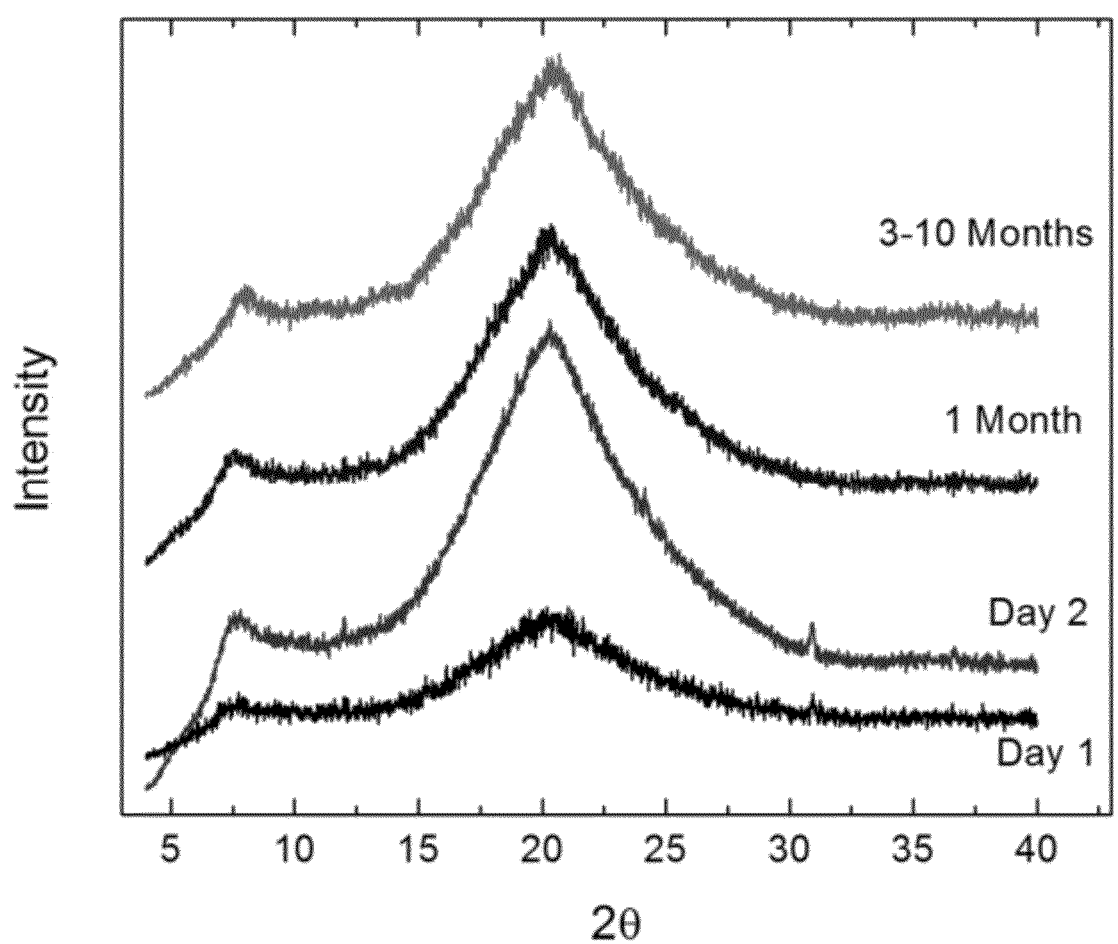
FIG. 7 includes XRD patterns of an amorphous Aliskiren/HPMC layer over times of 1 day, 2 days, 1 month, and 3 to 10 months.
Figure 8:
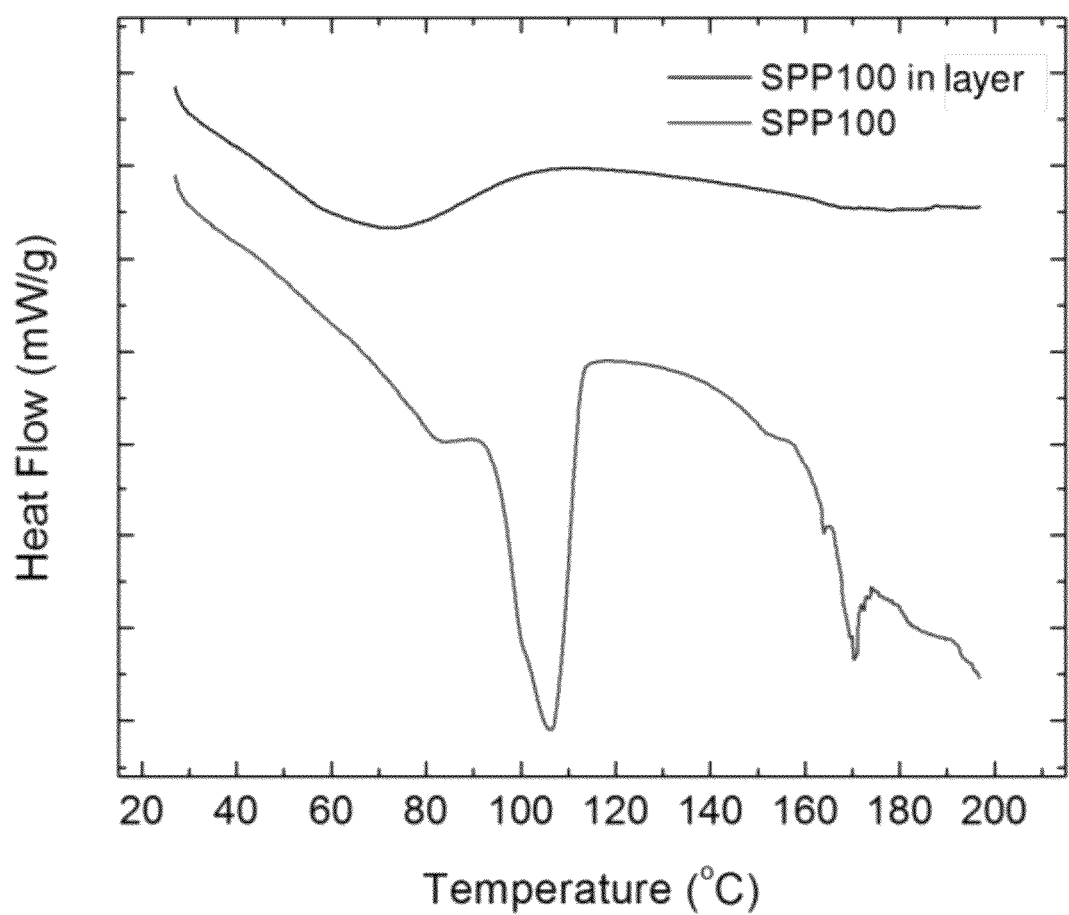
FIG. 8 includes DSC patterns of an amorphous Aliskiren/HPMC layer and a crystalline Aliskiren drug substance.
Figure 9:
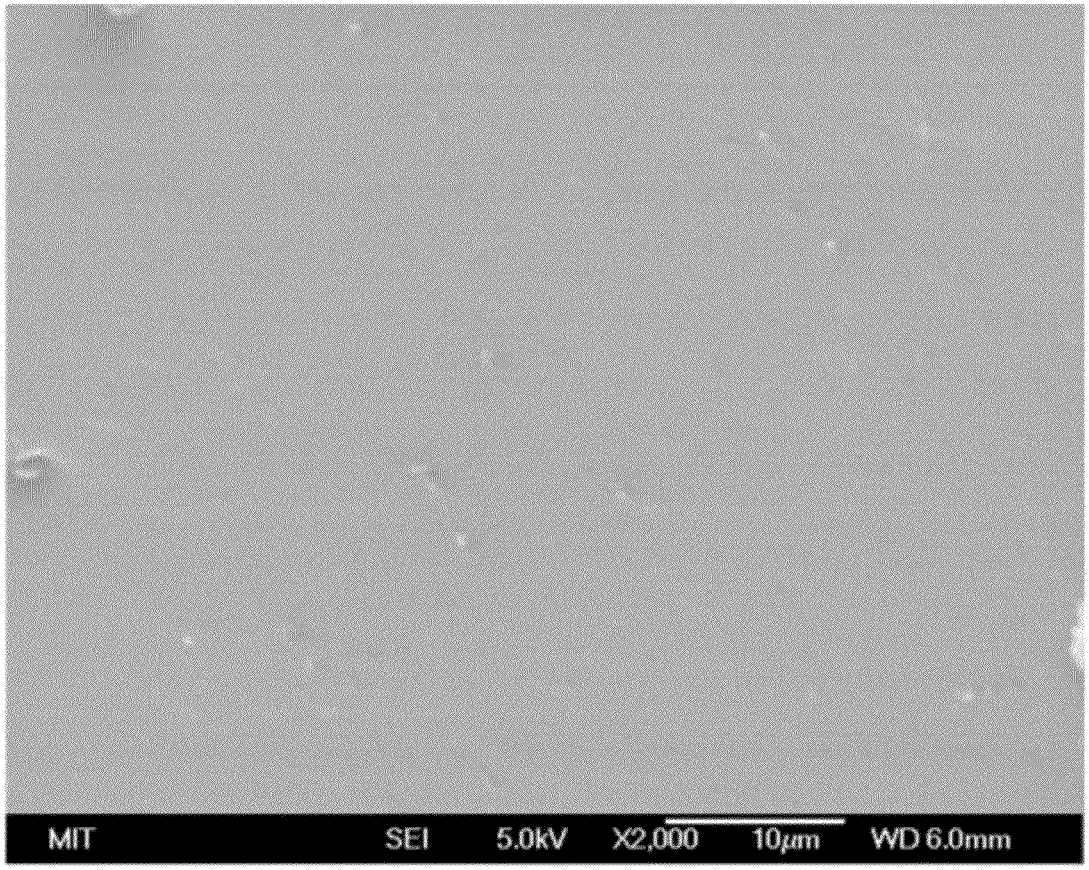
FIG. 9 includes an SEM image of Aliskiren/HPMC layers.

The physical stability of the aliskiren/HPMC layers was characterized by XRD and DSC, and the chemical stability was confirmed by HPLC. As shown in FIG. 6, the aliskiren/HPMC layer was completely amorphous, and it also remained amorphous over the time scale of these studies (10 months) as shown in FIG. 7. DSC data was also collected (FIG. 8) for further confirmation that the aliskiren was amorphous in the thin layer. A corresponding SEM image is shown in FIG. 9 and no characteristic indication of crystalline material was observed. Crystalline drugs, discussed later in this example, did not exhibit the same behavior (FIGS. 17A-H).

In order to confirm the chemical stability of the drug, HPLC was used. Different experiments were carried out to examine the level of degradation of aliskiren as the drying temperature and time increased. As shown in Table 2, as the temperature increased to above 90° C., aliskiren (10.9 min; aliskiren) degraded and a single degradation product, at the higher end of HPLC retention time (13.8 min; NAP 503-03), was observed. The highest allowable drying temperature was set to be 70° C. At 70° C., 60 min was the minimum drying time required to have layers that peel easily and that contain solvent content under regulatory requirements (ethanol<0.5% and water %<0.5%). The layers were stored in a vacuum desiccator overnight to remove excess solvent, and then sealed under vacuum for storage and further characterization.

TABLE 2

HPLC data for SPP 100 purity studies under different drying conditions and storage conditions

|  | 90° C. 30 min | 70° C. 30 min | 70° C. 60 min | 70° C. 90 min | 50° C. 90 min | 50° C. 180 min | 30° C. 180 min |
|---|---|---|---|---|---|---|---|
| ALISKIREN purity % | 98.8% | 99.5% | 99.3% | 99.2% | 99.5% | 99.5% | 99.6% |
| One single impurity >0.2% | Yes | No | No | No | No | No | No |

TABLE 2-continued

HPLC data for SPP 100 purity studies under different drying conditions and storage conditions

|  | 90° C. 30 min | 70° C. 30 min | 70° C. 60 min | 70° C. 90 min | 50° C. 90 min | 50° C. 180 min | 30° C. 180 min |
|---|---|---|---|---|---|---|---|
| Dry enough to be peeled off | — | No | Yes | Yes | Yes | Yes | Yes |
| Solvent inspection (<0.5%) after stored in dessicator overnight | — | — | Yes | Yes | Yes | Yes | Yes |

Figure 10:
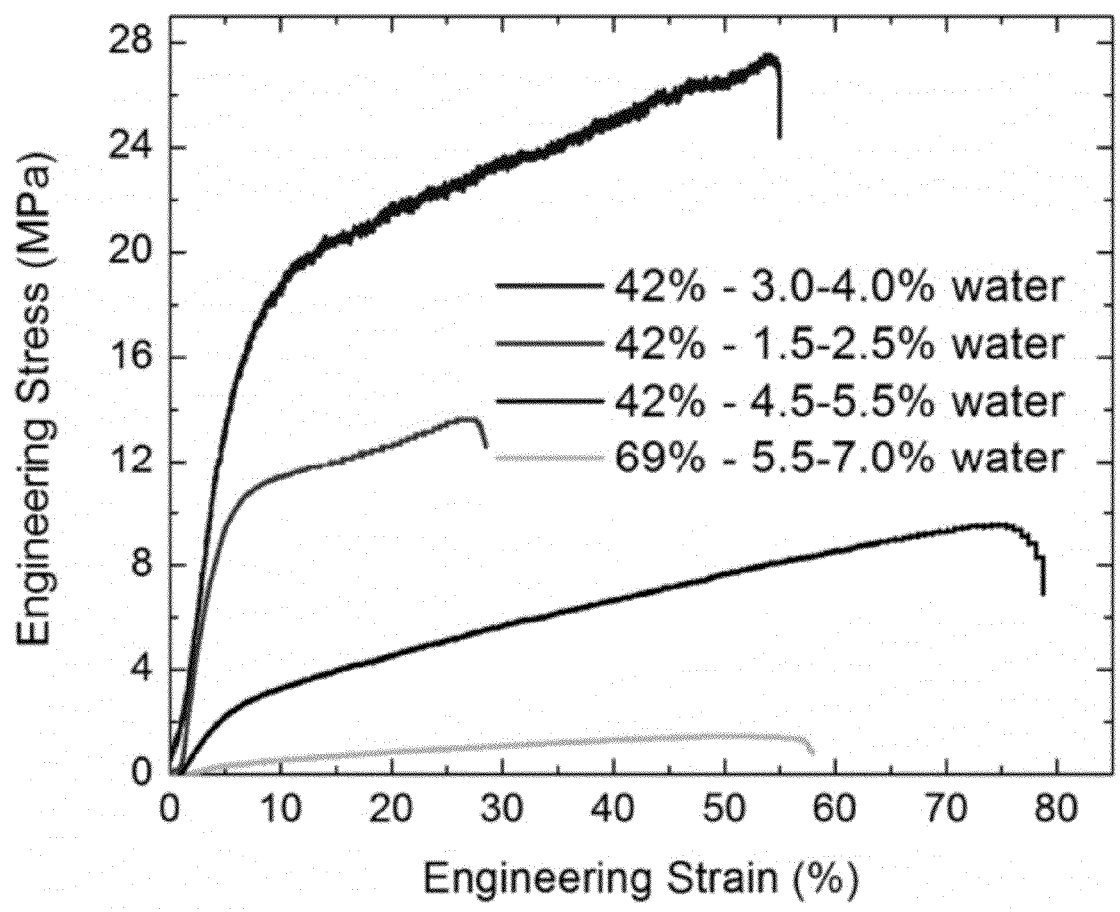
FIG. 10 includes Zwick of Aliskiren/HPMC layers with different water contents and different APIP contents.

The mechanical properties of the layers are important in determining whether layers can be manipulated as appropriate for the manufacturing process to be used. The tensile strengths of the layers varied with water content. When the layers were exposed to ambient air, relative humidity controlled the water content within the layer, and water acted as a plasticizer. In the Aliskiren/HPMC system tested in this example, both API and excipients were highly hydroscopic and absorbed atmospheric water easily, even during the time frame of one measurement (10 min). Increasing drying temperature and drying time, or storing the layer in desiccator decreased the amount of water contained in the layer. Zwick tensile tests were carried out under ambient conditions with lack of humidity control. Thus, there was significant error in the measurements of up to 20%. In addition, the water content in the layer varied during tensile test measurement; the water content before and after measurement did not agree and represented the range of water content for a given layer. As shown in FIG. 10, when the water content dropped from about 4.5-5.5% to 3.0-4.0%, the elongation at break was shortened while the engineering strain was extended. As the water % dropped further from 3.0-4.0% to 1.5-2.5%, the engineering strain reached a steady state while the engineering strain could be shortened further. The water content was calibrated by leaving the layer in ambient conditions to equilibrate. At 20° C., 50% RH, the layer with 42.7% API content reached a steady water % of about 4.5-5.5%. The drug content was increased to 69% and the tested water content was as high as 5.5-7% because of the highly hydroscopic effect of the API (Aliskiren) and correlated to a much lower engineering strain because of the lower percentage of polymer in the layer.

The transparent layers were manually folded and compacted into tablets (FIG. 11). The Micro-CT provided information on the quality of the tablets. It was clear that the tablets could maintain their round shape and less than 0.5% of void space observed. Lowering the plasticizer and increasing the excipient content both increased the void space in the folded and compacted tablets. Generally, better quality tablets were produced by carrying out the compaction in two directions The as-obtained tablets were then coated by Opadry AMB and placed at 40° C. for 75% R.H. for 1-month or 3-months stability tests. The results are summarized in Table 3. The as-obtained aliskiren/HPMC thin layer tablets had a pure aliskiren of 99.2% and a very similar qualified purity (99.1%) was maintained after one month storage in the coated samples and coated samples only. However, the same stability did not remain in uncoated samples or coated samples for up to 3 months storage in 40° C. and 75% R.H.

TABLE 3

Stability test for ALISKIREN/HPMC thin layer tablets stored at 40° C., 75% R.H.

| Purity of ALISKIREN | Pure ALISKIREN | Fresh thin layer tablets | 1 Month | 3 Months |
|---|---|---|---|---|
| Coated | 99.6% | 99.2% | 99.1% | 94.8% |
| Uncoated | 99.6% | 99.2% | 97.0% | 93.5% |

Figure 12:
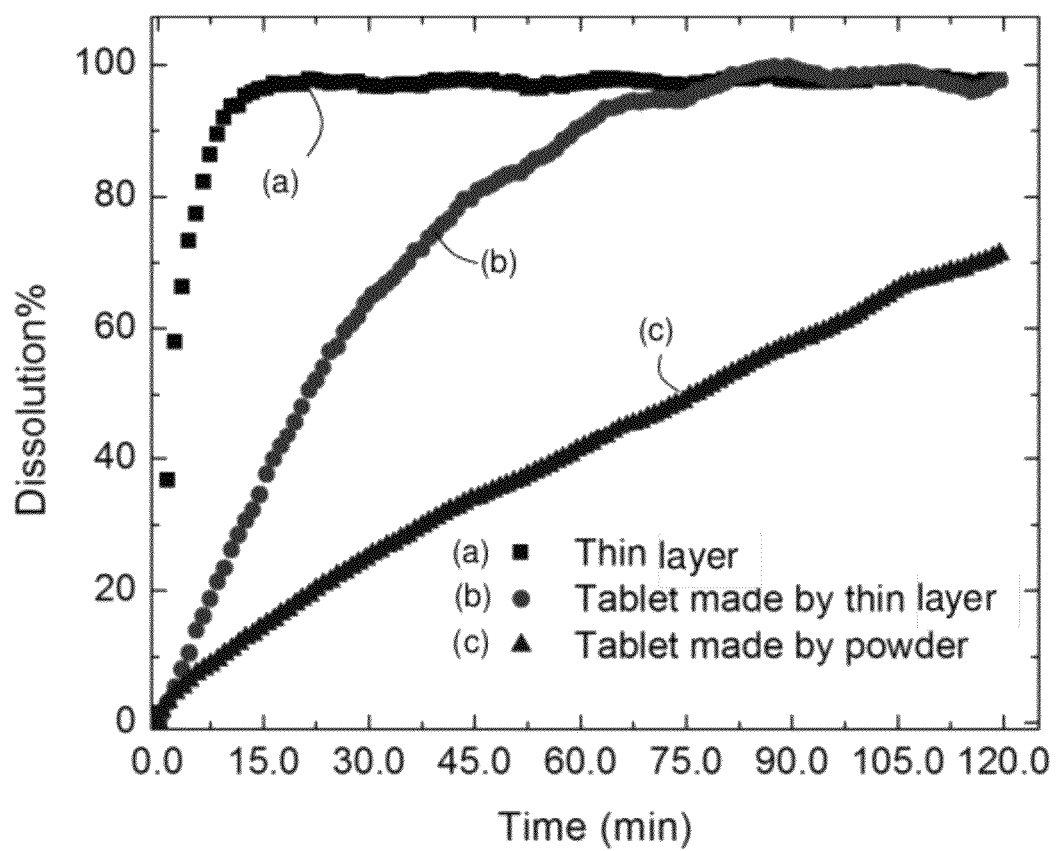
FIG. 12 includes dissolution profiles of Aliskiren/HPMC layers and tablets made from the layers with powder samples as reference.

Dissolution tests were carried out for the layers and tablets. For all dissolution tests, powder-compacted tablets were used as a control. FIG. 12 shows that the thin layer tablets exhibited an intermediate dissolution profile, when compared to pure thin layers and powder-compacted tablets. Dissolution tests were carried out in an artificial gastric setting consisting of 0.01 M HCl solution at 37° C. A reference solution containing pure API was used to calibrate the 100% dissolution point. The thin layer tablets dissolved much faster than the powdered tablets; this information can be used as a tool for designing a disintegration profile in addition to the excipient and drug's physical properties. But both tablet types had a delayed disintegration profile compared to the unprocessed thin layers. Not wishing to be bound by any particular theory, this may have been because HPMC forms a hydrogel shell around the outside the tablet which prevents the water from going in and further dissolving the API.

Crystallization Drug (ACM) in Different Thin Layer Formulations

To investigate formulation of crystalline drug in the thin layers, acetaminophen (ACM) was used because of its well-characterized physical and chemical properties. Compared to the amorphous drug (Aliskiren), ACM introduced additional challenges; its crystallinity influenced drug content, drying conditions, and the nature of the excipients and plasticizers that can be used.

Figure 13:
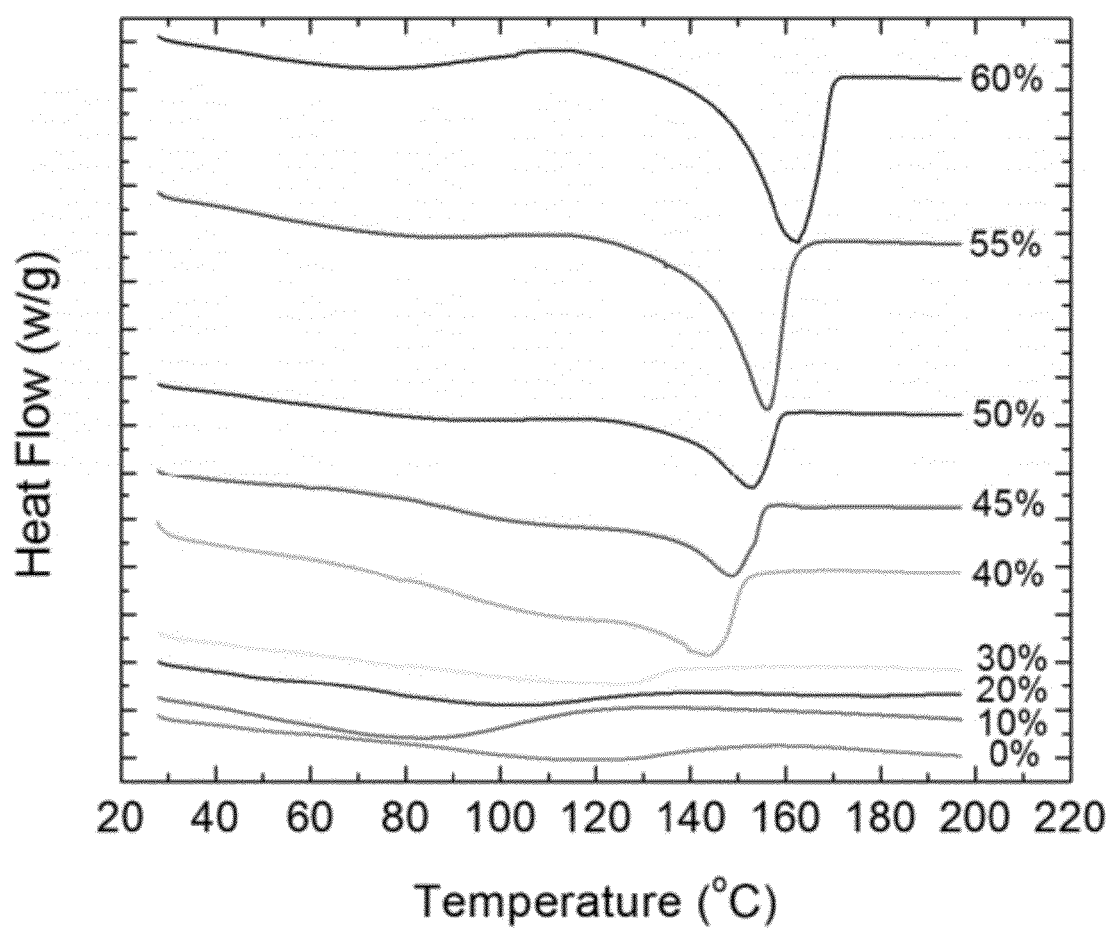
FIG. 13 includes DSC heating scans (dT/dt=+10° C./min) for acetaminophen/HPMC thin layer samples containing different amount of acetaminophen (10% to 60% API loading), together with a 0% layer (pure HPMC layers) as a reference.
Figure 14:
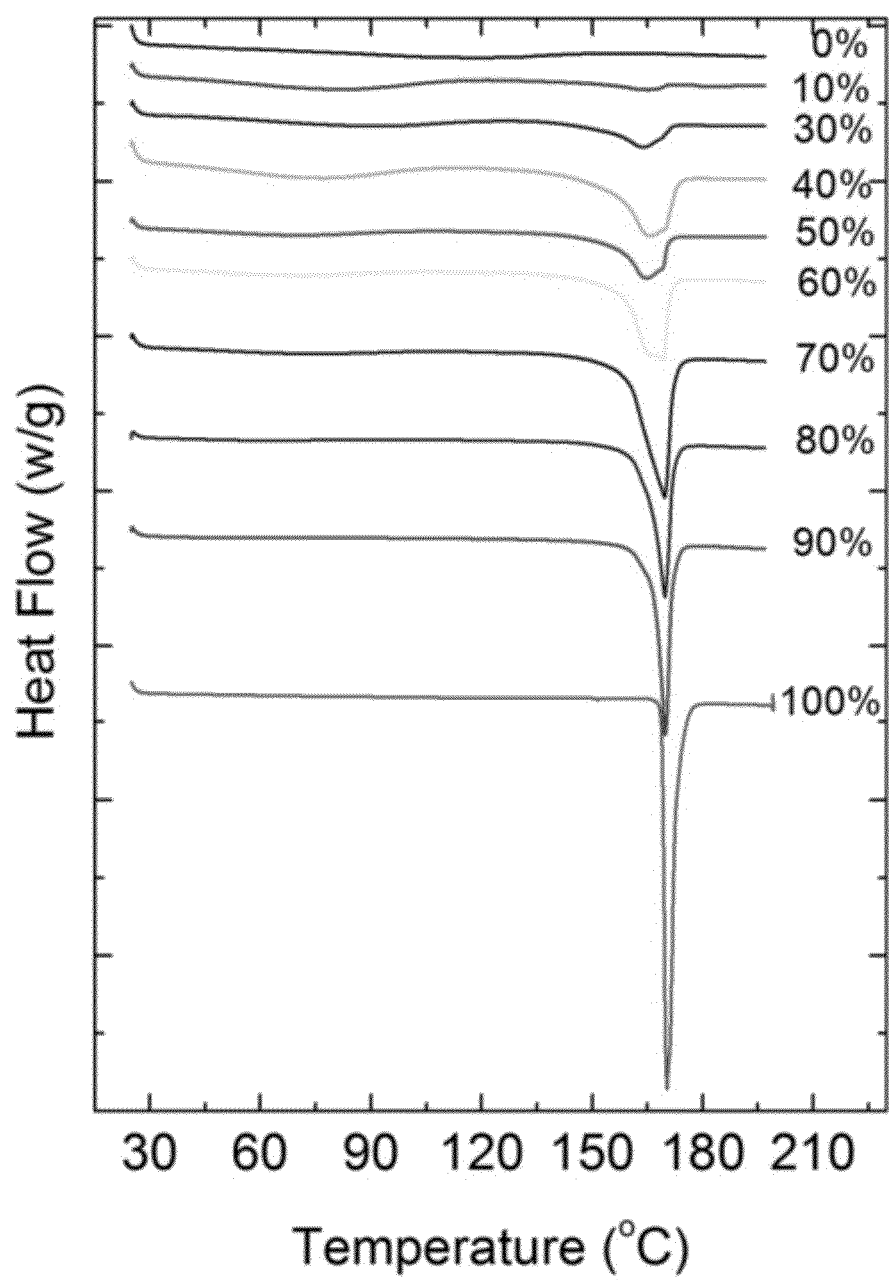
FIG. 14 includes DSC heating scans (dT/dt=+10° C./min) for acetaminophen/HPMC thin layer samples containing different amounts of acetaminophen (10% to 60% API loading), together with a 0% layer (pure HPMC layers) as reference.

Different amounts of ACM were loaded into a set quantity of HPMC solution using the following equation: ACM(xg)/(HPMC(1.0 g)+ACM(xg)+PEG(0.34 g))=10%, 20%, 30%, 40%, 50% and 60%. Layers were cast on a polyester liner with a starting thickness of about 1.2 mm. The cast layers were dried at room temperature with a relative humidity of 50% for 4 hours before being sealed under vacuum for further analysis. DSC patterns were collected on day 2 and are shown in FIG. 13. The resolvable melting peak in FIG. 13 for the Form I of ACM in the thin layer shifted from 162° C. to 143° C. as the drug content changed from 60% to 40%. The shift in the melting peak was affected by a miscible solid dispersion of ACM in a HPMC/PEG system. It was assumed that a pure physical mixture of the above mentioned chemicals at different percentages did not have influence peak shifts (FIG. 14).

Figure 15:
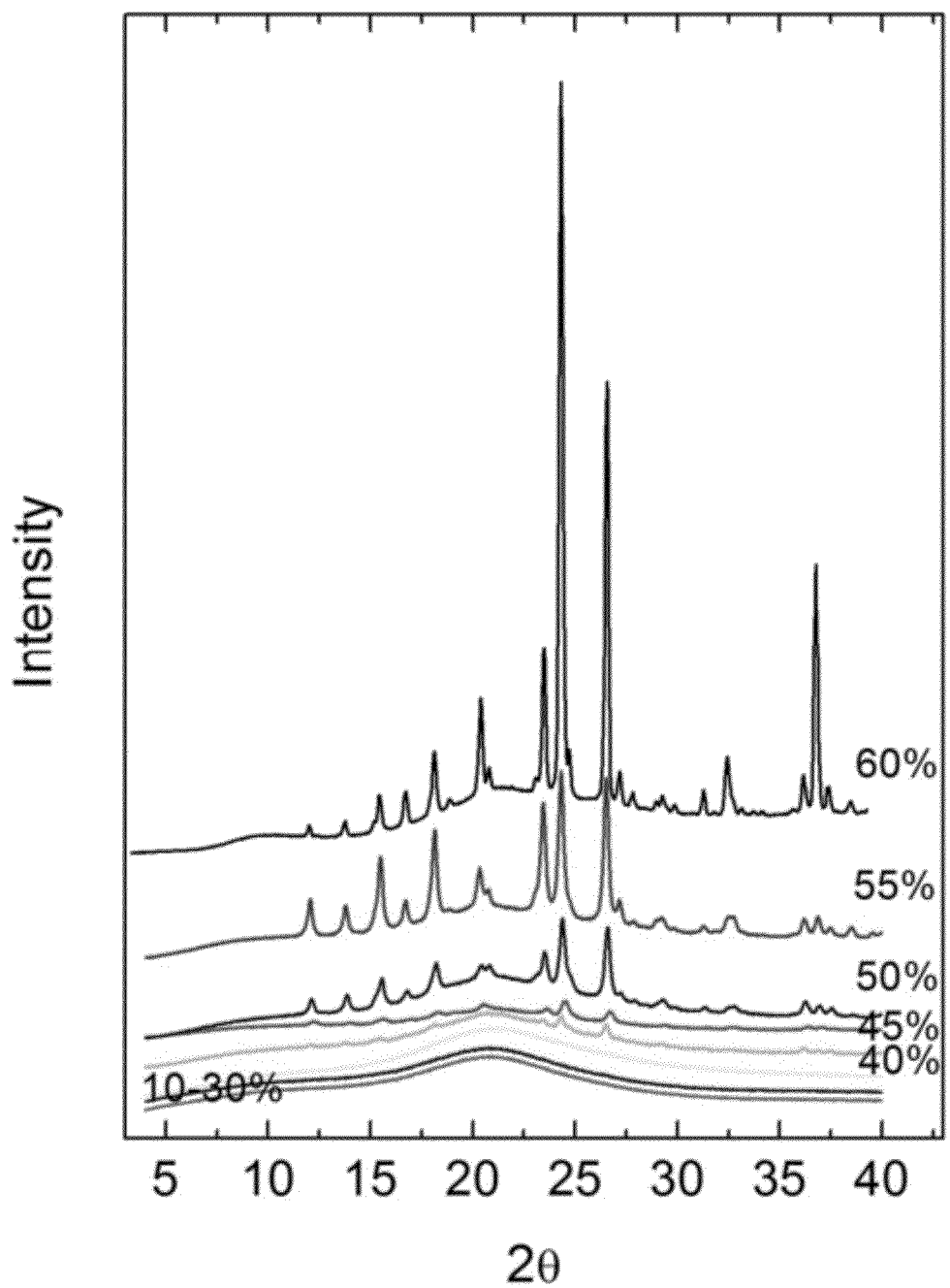
FIG. 15 includes XRD patterns for acetaminophen/HPMC thin layer samples containing different amounts of acetaminophen (10% to 60% API loading), corresponding to the DSC scans in FIG. 13.
Figure 18A:
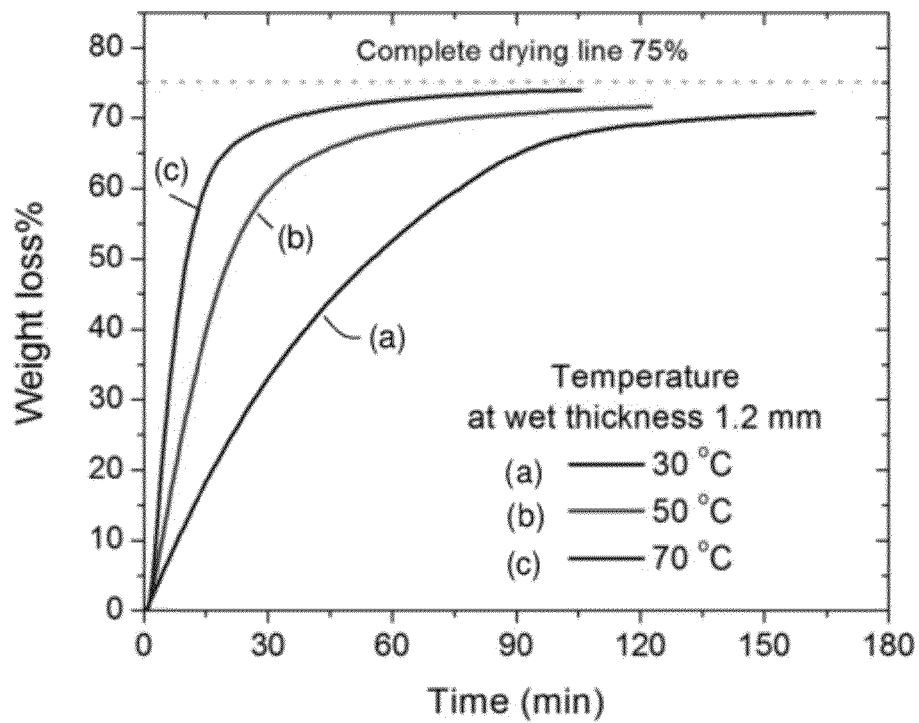
FIGS. 18A-18B include moisture analyzer drying curve data for layer casting of "60% sample" at (a) various casting temperatures and (b) various wet thicknesses.
Figure 18B:
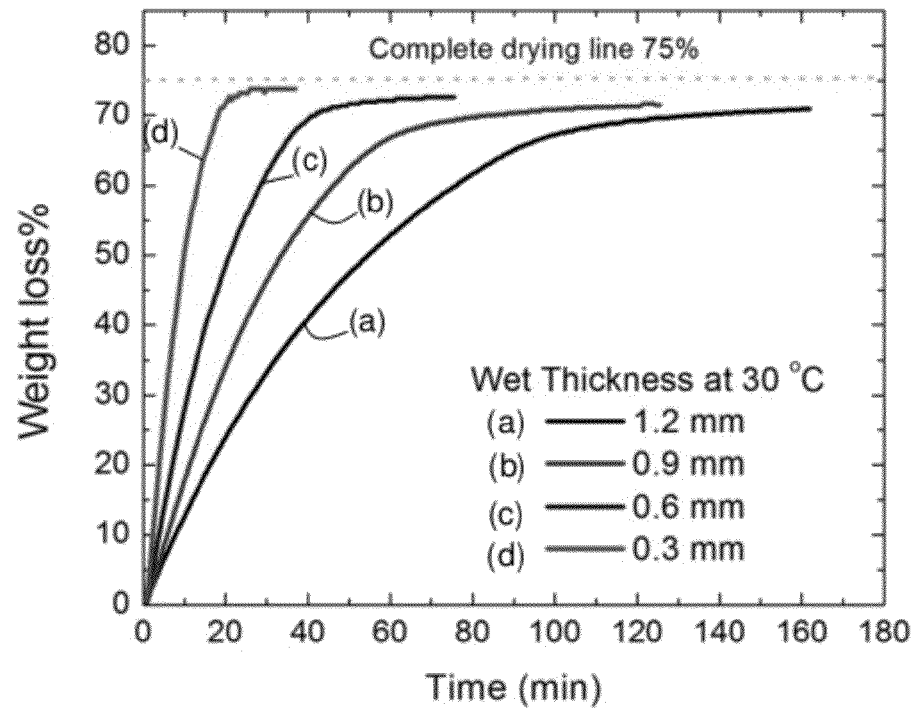
Figure 19A:
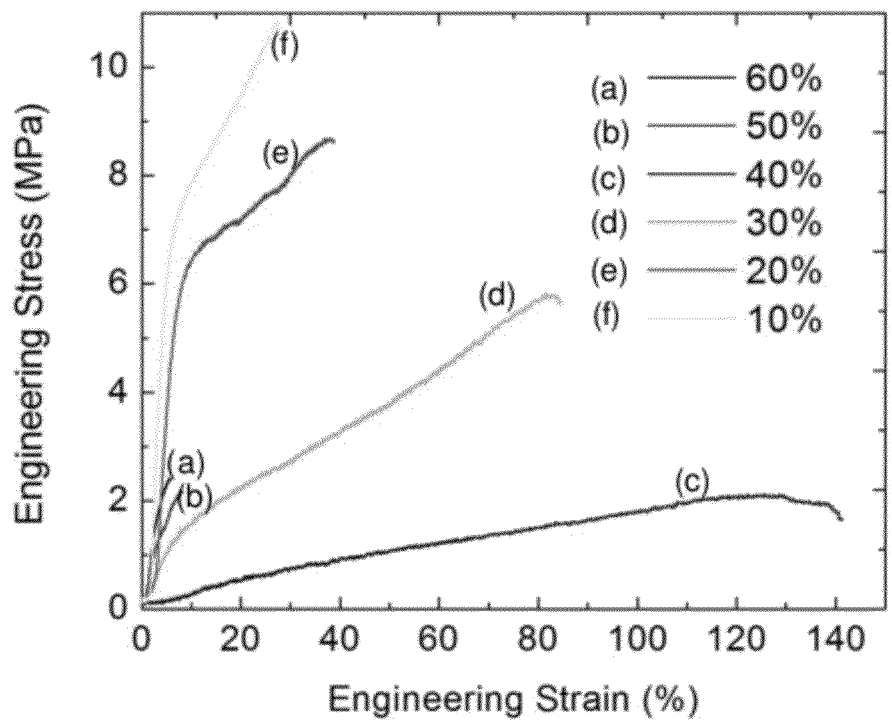
FIGS. 19A-19B include tensile strength data for different acetaminophen loadings (from 10 to 60%) in HPMC thin layers: (a) fresh layers; (b) after storage for 5 weeks under ambient conditions (20° C./50% R.H.).

The trend between final crystallinity and drug content was not linear, indicating that the kinetics of crystallization dramatically decreases as the ACM content decreases. Percent crystallinity data, shown in Table 4, was obtained by integrating the DSC melting endotherms after one month of storage, for drug content ranging from 60% to 10% using pure ACM. Physical mixtures of ACM and HPMC (ACM content ranging from 60-10%) were used as references to validate the DSC method. There are two regions that show a dramatic change in the % crystallinity: the first is 20% to 30% ACM loading, the second is 40 to 50% loading. These findings were in accordance with tensile strength test results for the layers (FIG. 19A). Samples with drug content below 20% showed very similar mechanical properties to pure polymers, which indicated a good solid dispersion or even solid solution within the drug and polymer containing layers. As the drug percentage was increased above 20% but below 40%, a small domain of drug started to crystallize, which weakened the polymer tensile strength. Once the drug content was above 45%, there was a clear phase separation between polymer and drug; in this regime, the polymer completely lost its original mechanical profile and appeared as a substrate or medium to retain the crystals. These observations were consistent with the SEM results (FIGS. 17A-H). Similar crystallization studies according to ACM content were also carried out by XRD as shown in FIG. 15 to validate the trend as shown in DSC in FIG. 13. But because the diffraction patterns can be largely influenced by the crystal preferred orientation and/or lattice defect other than percentage of crystallinity; the XRD patterns are not employed to quantitatively study the crystallization process of ACM in the layers.

of the polymeric excipients and the ACM was observed. The ACM crystals were rod shaped, 100 micrometers by 300 micrometers, and embedded in the polymer matrix. In FIGS. 18A and 18B, the layer drying conditions were systematically changed by temperature only and by thickness only to examine its effect on production rate and the quality of the layers with fully crystalline materials. Temperature-dependent drying gives correlated data in FIG. 18. Adjusting the drying temperature can effectively reduce the drying time; however, it can also compromise the crystallinity of ACM in the layers. The mobility of ACM molecules is reduced in the denser polymer matrix and the crystallization process was noticeably slowed when the driving temperature was adjusted.

Reducing layer thickness shortened drying time, and decreased the amount of water retained after drying (FIG. 18B). In the ACM/HPMC/PEG/Ethanol/water system that was studied in this example, it was difficult to quantitatively study the drying mechanism but, without wishing to be bound by any particular theory, the following qualitative observations might accurately describe the drying mechanism: At the interface between the casted viscose and air, the concentration of ethanol, is decreasing more rapidly due to its high volatility as compared to water. When the depletion of ethanol and water go to completion, further evaporation will encounter much more restrictions because of the solicitation of the polymer network. By then, both the water and ethanol concentration gradients will become steep. In this process, the initial thickness resulted in an increase in the total mass of ethanol and so a greater depletion time of ethanol, which will then cause a greater asymmetry in the final membrane structure with a thicker densified "skin," due to the higher polymer concentration near the free surface. However, research has shown that manufacturing of thinner layers will increase production cost in terms of building a drying platform, layer folding and tablet forming.

Figure 19B:
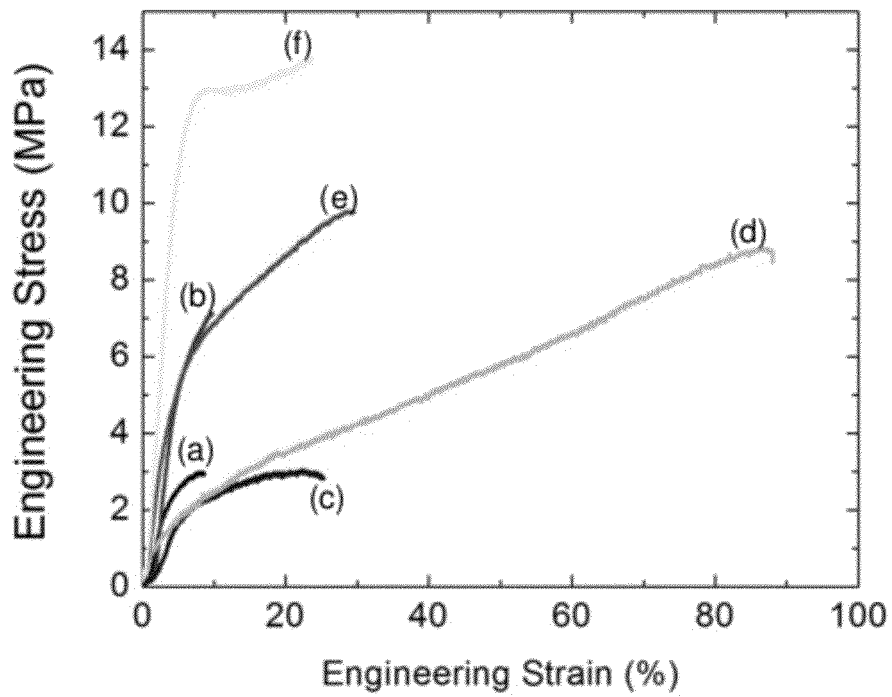

ACM/HPMC layers were characterized by their elastic mechanical properties at ambient temperature and 50% R.H. (FIG. 19). Mechanical parameters were tabulated in Table 5. Samples with ACM content below 40% showed elastoplastic like behavior with stress increasing rapidly at small strains and more slowly after a yield point. When ACM content was increased from 10% to 40%, acetaminophen behaved as a plasticizer and its tensile strength (Young's Modulus) was reduced, but its elongation at break (UTS) increased. In contrast, once the phase separation occurred, as in the cases of 40% one month storage layers vs. fresh ones, and the 50% and 60% layers, the crystalline ACM served as notches and weak-

TABLE 4

Percentage of crystallization analysis by DSC after 2 months storage at room condition (20° C., 50% R.H.)

|  | 10% | 20% | 30% | 40% | 50% | 60% |
| --- | --- | --- | --- | --- | --- | --- |
| Real pct of crystallization by DSC* | 0.0% | 1.9% | 12.3% | 19.2% | 64.4% | 97.5% |
| Real pct of crystallization by XRD (2θ = 24.3) | 0.0% | 0.0% | 0.0% | 1.4% | 11.3% | 100.0%[#] |

*Real pct of crystallization = pct of crystalline ACM in the layer calculated by DSC/pct of crystalline ACM in the layer assuming the crystallization process is complete

[#]60% ACM content in the layer is used as a reference to indicate a 100% crystallinity. The crystallization percentages for sample s 40% and 50% are then calculated based on diffraction peak area at 2θ = 24.3.

Figure 16:
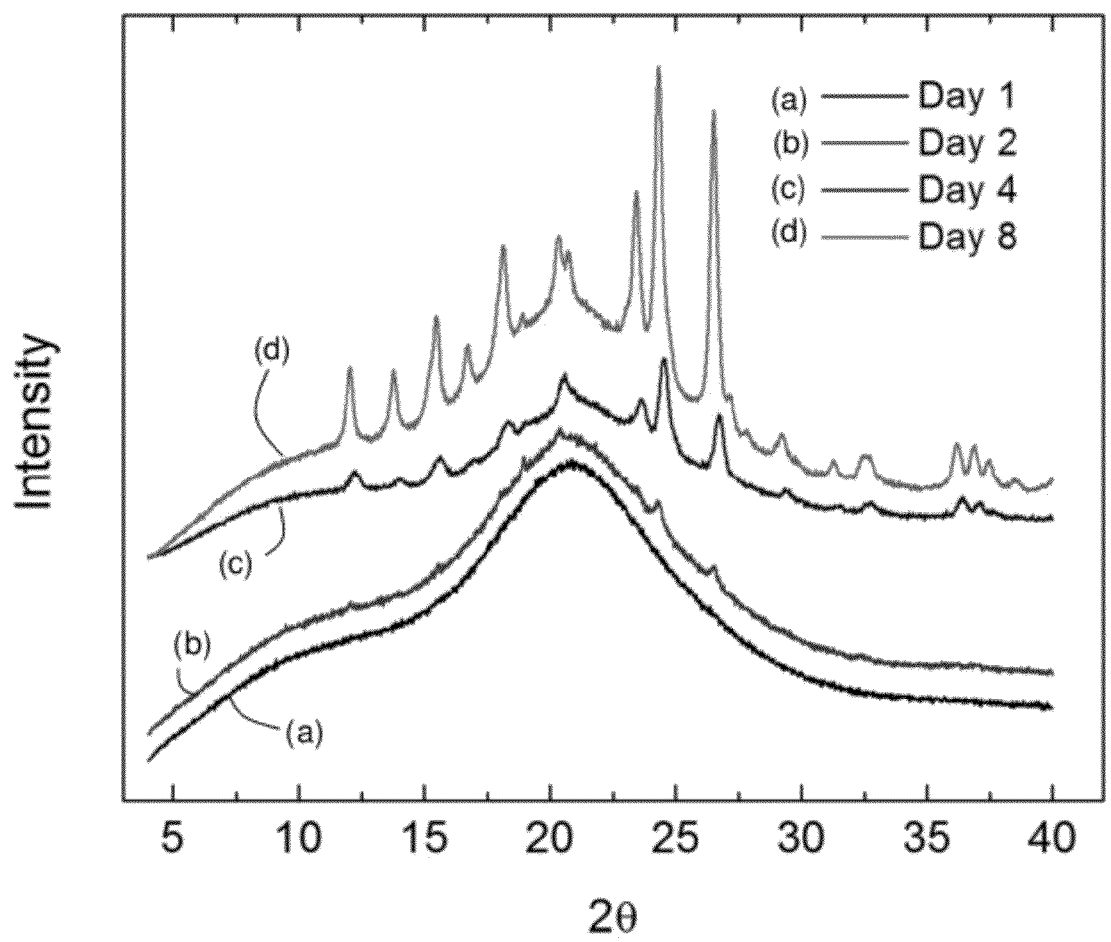
FIG. 16 includes XRD patterns of 45% ACM/HPMC thin layer samples at days 0, 1, 4 and 8.

A drug content of 45% was chosen to study the kinetics of crystallization because the ACM crystallized over a suitable time scale at this content level. The XRD patterns for this study are shown in FIG. 16, and all the diffraction patterns were characterized as the Form I of ACM. The XRD patterns indicated that the initial material was amorphous and kinetically stable over the 1 hr scan at room temperature. For the data collected at days 1, 4 and 8, the intensity of the diffraction peaks corresponding to crystalline ACM increased significantly. Changes in the DSC patterns were not as obvious as those in the XRD patterns for the 45% loading samples. This could be due to the lack of sensitivity to changes in crystallinity by DSC compared to XRD.

SEM images for the different drug contents are shown in FIGS. 17A-17D and show that as the ACM content increased, crystals with a better defined morphology were obtained. At a loading of 60%, as in FIGS. 17C-D, a clear phase separation ened the polymer layers resulting in a significant loss of Tensile strength (Young's Modulus) and plasticity (elongation at break).

TABLE 5

The mechanical properties of the thin layers with different amount of acetaminophen content.

| ACM content | Samples | Young's Modulus MPa | Yield Strength (0.2% off set) | | UTS | | Fracture Strain % | Fracture Stress (Mpa) |
|---|---|---|---|---|---|---|---|---|
| | | | Strain (%) | Stress (MPa) | Strain (%) | Stress (MPa) | | |
| 10% | Fresh | 232 ± 14 | 5.8 ± 0.1 | 6.7 ± 0.5 | 31.8 ± 4.1 | 10.9 ± 1.8 | 31.4 ± 4.8 | 10.5 ± 1.9 |
| | 1 month | 255 ± 25 | 4.9 ± 0.1 | 10.7 ± 0.2 | 23.8 ± 0.7 | 13.7 ± 2.1 | 24.3 ± 0.6 | 13.6 ± 2.1 |
| 20% | Fresh | 130 ± 30 | 2.4 ± 0.5 | 3.5 ± 0.3 | 38.7 ± 5.4 | 7.1 ± 0.5 | 38.2 ± 1.3 | 7.8 ± 0.4 |
| | 1 month | 129 ± 16 | 3.8 ± 0.3 | 4.4 ± 0.5 | 29.3 ± 2.1 | 9.7 ± 1.0 | 30.1 ± 2.0 | 9.6 ± 1.1 |
| 30% | Fresh | 16 ± 3 | 8.9 ± 1.9 | 1.4 ± 0.2 | 83.1 ± 14.6 | 5.6 ± 0.6 | 83.9 ± 16.6 | 5.4 ± 0.7 |
| | 1 month | 52 ± 17 | 1.8 ± 0.7 | 0.9 ± 0.4 | 86.7 ± 8.4 | 8.8 ± 1.3 | 88.0 ± 8.1 | 8.7 ± 1.5 |
| 40% | Fresh | 5 ± 1 | 5.2 ± 1.5 | 0.4 ± 0.1 | 128.9 ± 20.8 | 2.4 ± 0.5 | 138.8 ± 37.4 | 1.9 ± 0.3 |
| | 1 month | 36 ± 11 | 4.9 ± 0.4 | 1.7 ± 0.2 | 9.8 ± 3.0 | 7.1 ± 0.6 | 9.8 ± 2.8 | 7.1 ± 0.6 |
| 50% | Fresh | 56 ± 35 | 1.9 ± 0.8 | 1.3 ± 0.2 | 8.2 ± 1.5 | 2.3 ± 1.2 | 9.3 ± 2.7 | 2.1 ± 1.3 |
| | 1 month | 180 ± 9 | 3.2 ± 0.6 | 1.6 ± 0.6 | 22.8 ± 1.5 | 3.0 ± 0.4 | 25.4 ± 1.8 | 2.8 ± 0.3 |
| 60% | Fresh | 89 ± 10 | 2.5 ± 0.4 | 1.7 ± 0.3 | 5.6 ± 2.0 | 2.4 ± 0.2 | 6.7 ± 2.1 | 2.3 ± 0.2 |
| | 1 month | 102 ± 15 | 2.9 ± 1.3 | 2.8 ± 1.2 | 8.6 ± 0.9 | 3.0 ± 1.1 | 8.6 ± 0.9 | 3.0 ± 1.0 |

Figure 17:
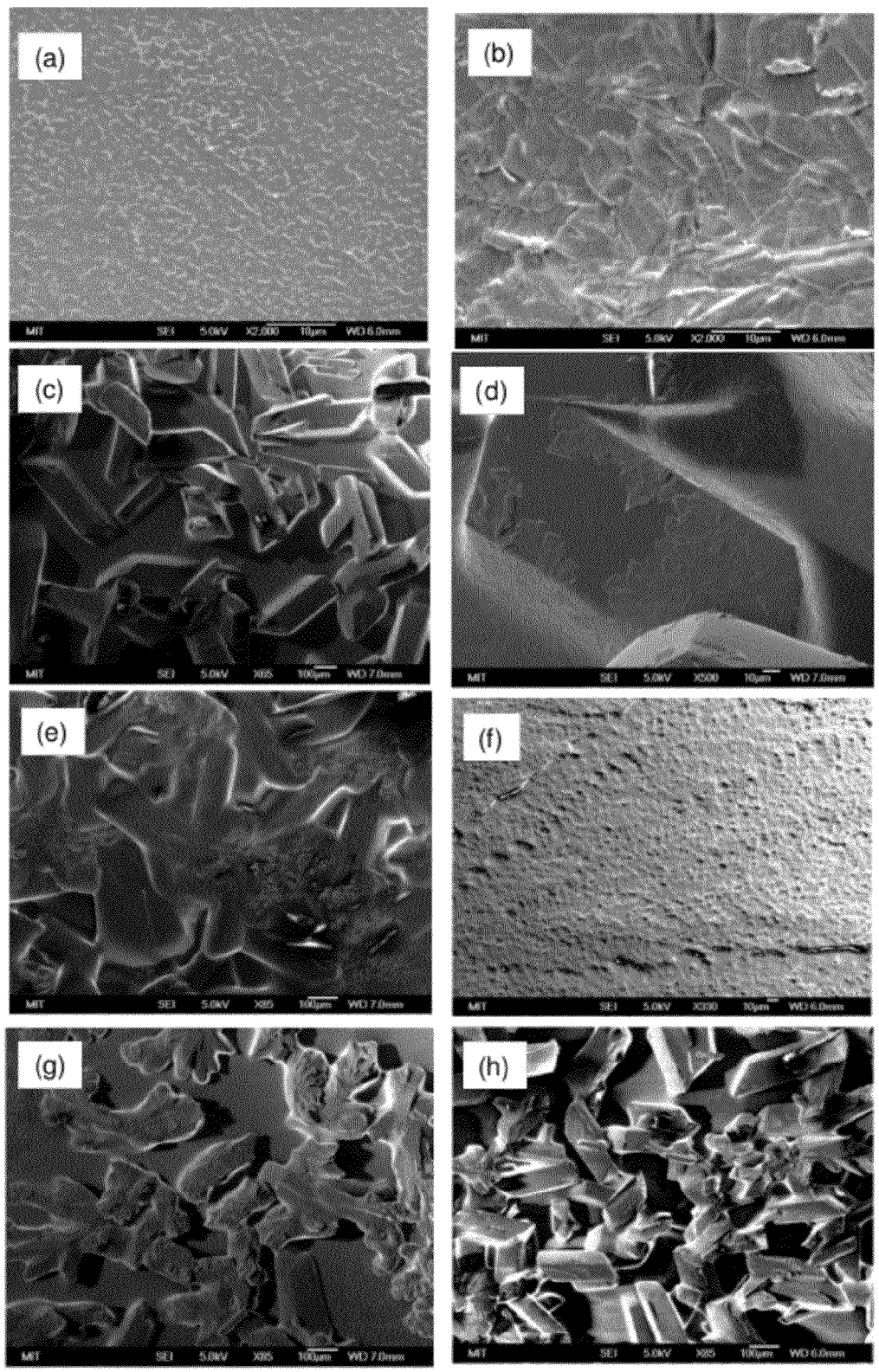
FIGS. 17A-17H include SEM images of the surface morphology of acetaminophen/HPMC layers: (a) 10% layer cast with a wet thickness of 1.2 mm 20° C. and 50% R.H.; (b) a 50% layer cast with a wet thickness of 1.2 mm 20° C. and 50% R.H.; (c, d) 60% layers cast with a wet thickness of 1.2 mm at 20° C. and 50% R.H.; (e) 60% layer cast with a wet thickness of 1.2 mm at 50° C.; (f) 60% layer cast with a wet thickness of 1.2 mm at 70° C.; (g) 60% layer cast with a wet thickness of 0.3 mm 20° C. and 50% R.H.; (h) 60% layer cast with a wet thickness of 0.6 mm 20° C. and 50% R.H.

High ACM content layers were brittle and had clear phase separation, which was verified by SEM images in FIG. 17. ACM crystals appeared on the layer; the 60% ACM layer had crystallites embedded in an amorphous HPMC phase and it weakened the hydrogen bonding in the polymer network (FIGS. 17C-D). In general, the tensile strength decreased proportionally to the ACM content, whereas the percentage elongation increased, particularly in the case of fresh 40% layers which reached almost 138.8% elongation at break; however, once phase separation occurred and ACM started to crystalline, the plasticity decreased significantly to only 9.8%. Any layers that had less than 30% ACM loading (with more than 30% fracture strain at break in Table 5) exhibited strong enough mechanical properties to be handled by layer folding and tablet forming, regardless of whether the layers were freshly made layers or one month old layers. However, the 60% layers, and the 40% and 50% one month layers experienced difficulties in a direct layer folding and table forming as the crystals tended to "tear apart" the layers by simple manually folding.

Figure 20:
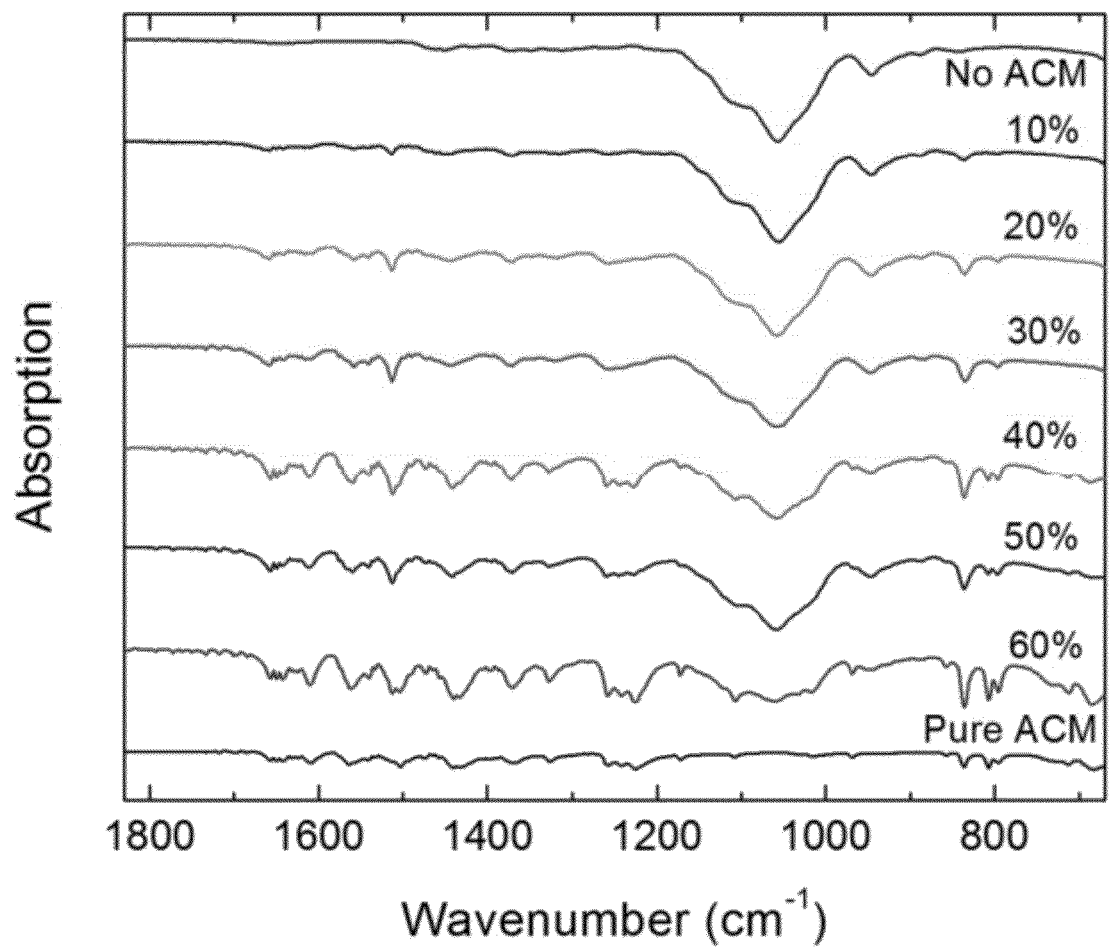
FIG. 20 includes FT-IR spectra for different acetaminophen loadings in HPMC thin layers.

FT-IR spectra of different ACM contents in the HPMC thin layers are shown in FIG. 20. The peaks at 1653-1641, 1562 and 1258-1226 cm$^{-1}$ were assigned to the C=O stretching vibration, N—H in-plane bending, C—N stretching bands, respectively. The peaks at 1609, 1513 and 1441 cm$^{-1}$ were likely due to the C—C bond stretching of the aromatic benzene ring. The peak at 1372 cm$^{-1}$ likely corresponded to the symmetric CH$_3$ bending vibration, and the peak at 1327 cm$^{-1}$ was assigned to the C—N stretching vibration. The peaks at 1258-1226 and 1171 cm$^{-1}$ also likely corresponded to the C—O stretching vibrations. A comparison of the three spectra with pure ACM indicated that there was no variation in the molecular interactions experienced by ACM before and after processing with polymers.

Figure 21:
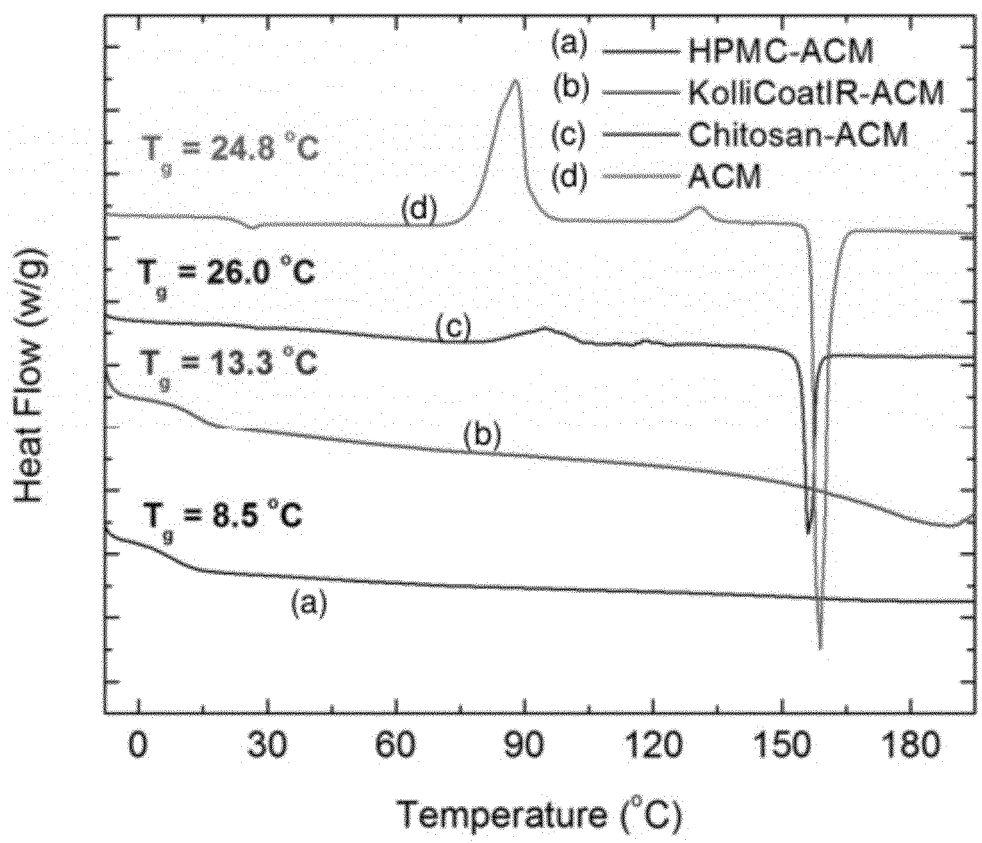
FIG. 21 includes DSC heating scan (dT/dt=+10° C./min) for (a) a completely amorphous acetaminophen sample prepared by rapid melt quenching. A glass transition at $T_g$=24.8° C., 26.0° C., 13.3° C. and 8.5° C. are observed for pure acetaminophen or acetaminophen in Chitosan, KolliCoat IR and HPMC thin layers, respectively.

Most thin layer drug products are initially amorphous, but tend to crystallize slowly over time. Time and material consuming storage experiments are usually required to study the stability of amorphous drug candidate. It is necessary to predict the amorphous stability of drug candidates early in the formulation process. However, the glass transition temperature of the polymer is masked by the melting peak of the drug and little extra information can be extracted. The DSC heating curve for a sample quench cooled after being melted gave information on the glass transition temperature, the crystallisation exotherm, and the melting endotherm (FIG. 21). Samples were prepared by melting in closed DSC pans from R.T. to 200° C. at a rate of 10° C./min and subsequently cooled to −10° C. at a cooling rate of 10° C./min. The pure ACM phases were well studied by DSC; the amorphous form a glass transition peak at 24.8° C., a crystallization peak between 65° C. to 100° C., a solid state transition at about 130° C. from Form III to Form II, and a melting peak for Form II at about 158° C. The glass transition for amorphous ACM shifted to a lower temperature as the kinetics of the crystallization of ACM (50% loading for example) in the layer decreased as the excipient was changed from HPMC ($T_g$=6.8° C.; crystallization of ACM in the layer happens in the order of months) to Chitosan ($T_g$=26° C.; crystallization of ACM in the layer happens in the order of hours) and KolliCoat IR ($T_g$=13.3° C.; crystallization of ACM in the layer happens in the order of days) (Table 6).

TABLE 6

Glass transition temperature for rapid quench 50% ACM layers with different excipients

| ACM layers in | HPMC | Chitosan | KolliCoat | ACM only |
|---|---|---|---|---|
| $T_g$ (° C.) | 6.8 | 26 | 13.3 | 24.8 |
| Crystallization time | >2 months | <6 hrs | 1-8 days | <6 hrs |

Figure 22:
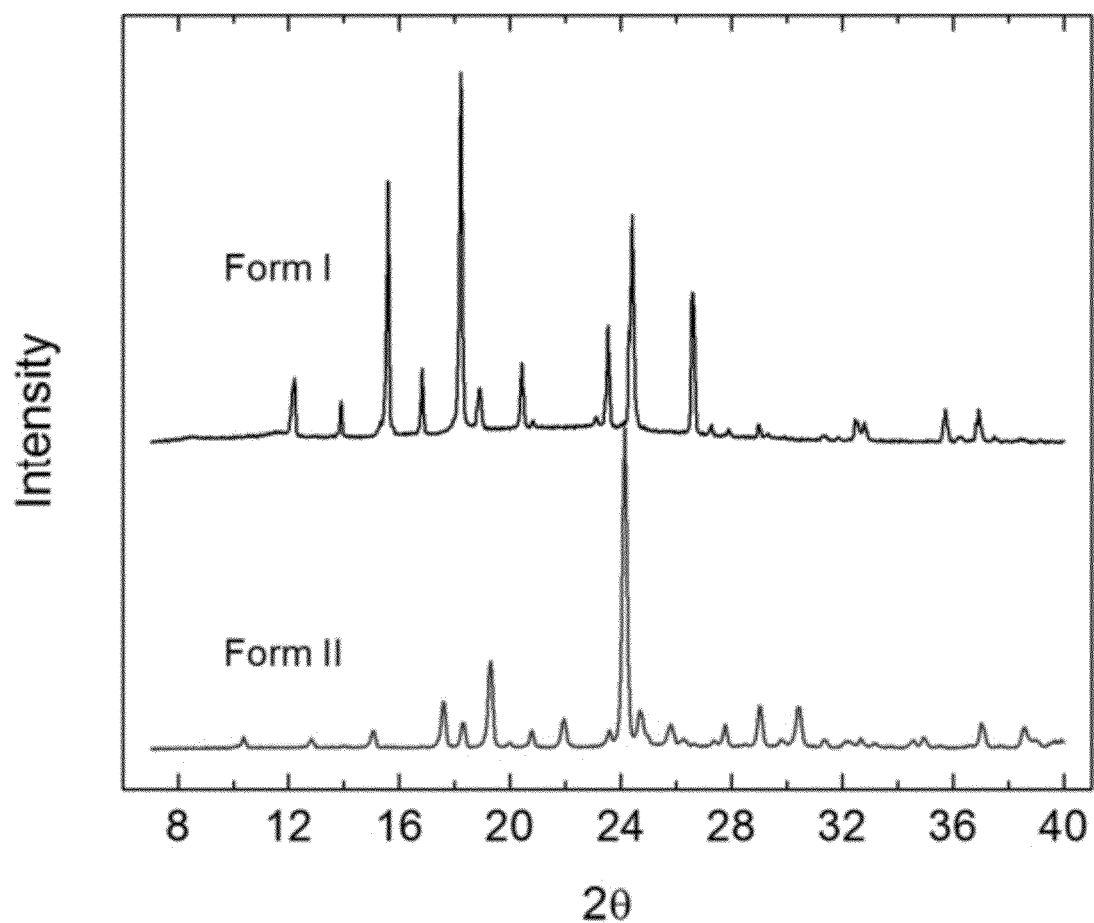
FIG. 22 includes XRD patterns of acetaminophen form I (same patterns observed for 50% ACM content in layers of HPMC or KolliCoat IR or Chitosan) and form II (Chitosan ACM form II and pure ACM form II samples by heating samples again after preparing samples by rapid melt quenching).
Figure 23A:
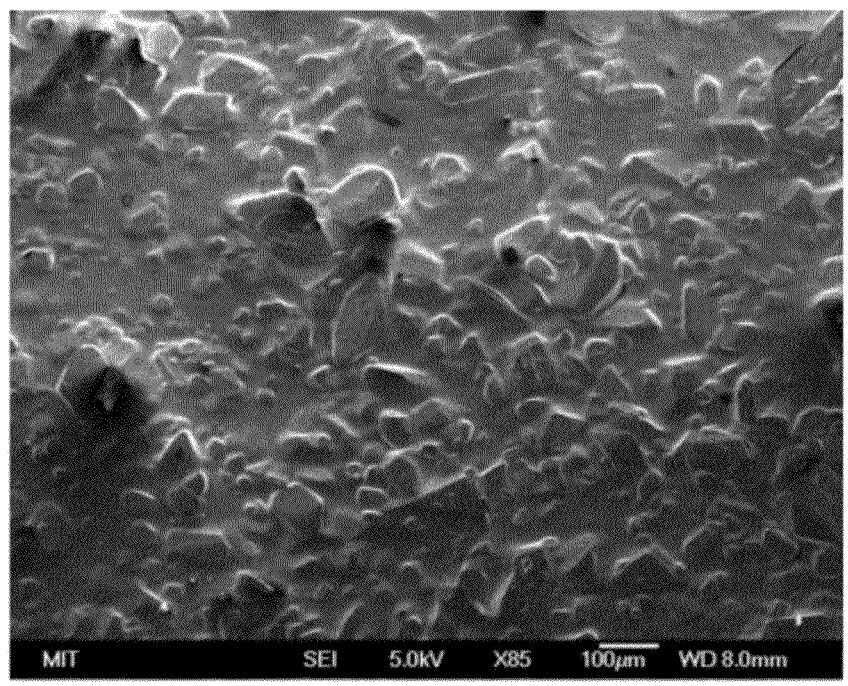
FIGS. 23A-23B include SEM images of the surface morphology of (a) an acetaminophen and Chitosan layer and (b) an acetaminophen and Killicoat IR layer cast with a wet thickness of 1.2 mm at 20° C. and 50% R.H.
Figure 23B:
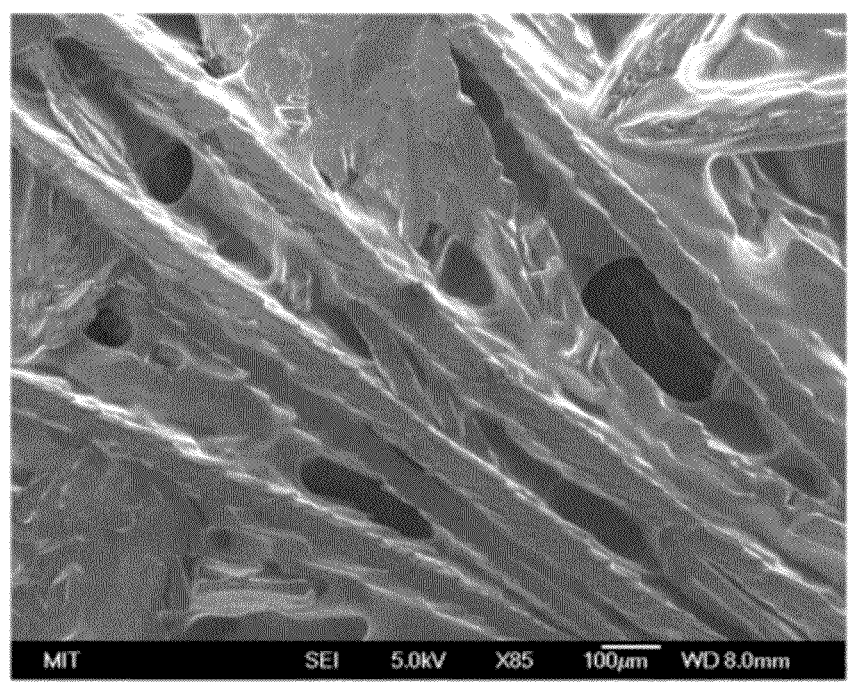

The unheated Chitosan/ACM samples were confirmed to contain Form I ACM by XRD (FIG. 22). After the heating/cooling cycle, Form II was observed for all three types of thin layers. The morphology of ACM crystals varied significantly with different excipients, as shown in the SEM images in FIG. 23. Irregular shaped cubes 50 micrometers to 120 micrometers in size were observed for chitosan/ACM layers and long needle like crystals (80 micrometers×1-3 cm) were observed for KolliCoat IR/ACM layers.

Figure 24A:
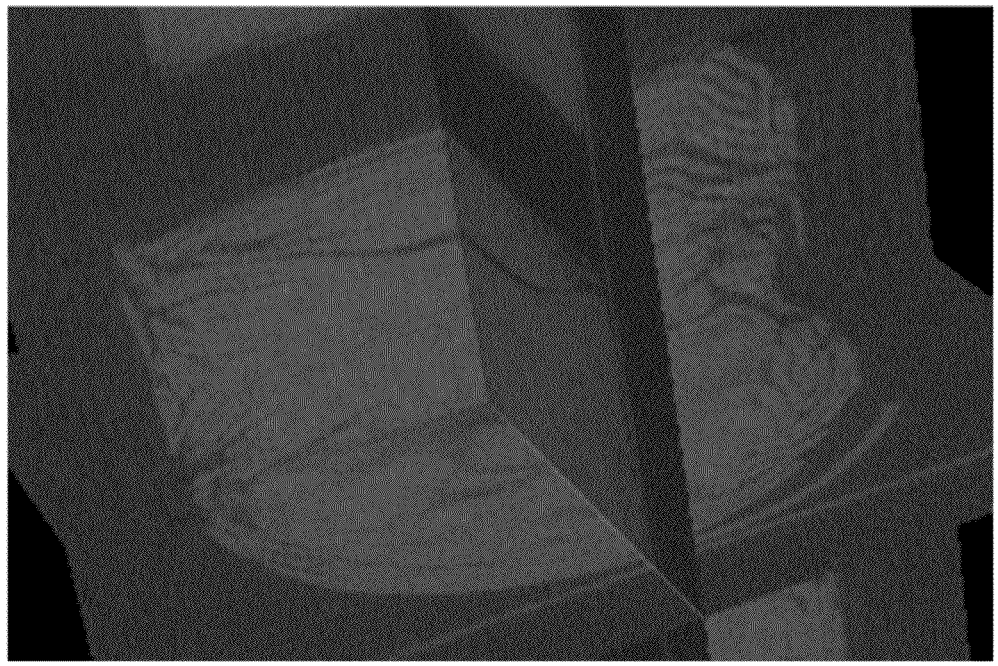
FIGS. 24A-24C include micro-CT cross sectional views of manually compressed thin layer tablets of: a) HPMC/acetaminophen; b) Chitosan/acetaminophen; c) KolliCoat IR/acetaminophen.
Figure 24B:
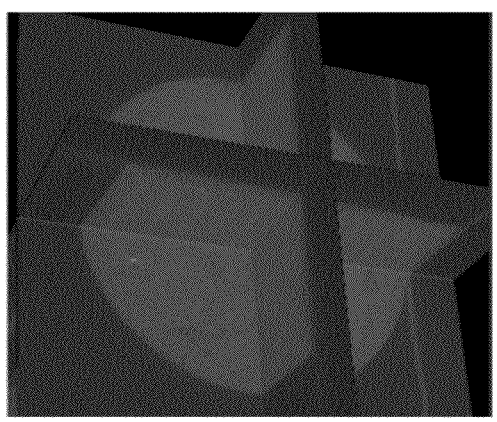
Figure 24C:
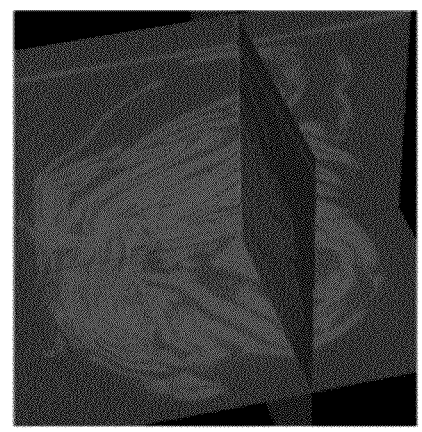

It was confirmed that the thin layer formulation could be made into tablets. Cross-sectional 3D images of HPMC/ACM, Chitosan/ACM and KollicoatIR/ACM samples are shown in FIG. 24. It can be seen that both HPMC/ACM and Chitosan/ACM layers can be shaped into tablets without further deformation. In particular, Chitosan and Form I ACM were easily compressed into high quality tablets without substantial void space inside (FIG. 24B), an observation that contradicts the acknowledged premise that Form I of ACM is hard to compress. Without wishing to be bound by any particular theory, it is believed that the process provides a route to manufacturing thermally stable monoclinic acetaminophen via thin layer into a final tablet. In particular, the exact shape and size of the tablet can depend on the amount and duration of pressure application, and deformation characteristics of the films. Deformation models for multiple of thin-films can be developed (as explained later) and appropriate tablet-sizing can be achieved.

EXAMPLE 2

This example describes a system design for polymeric thin-film tablet manufacturing. In particular, to convert thin-film polymeric layers into tablets, one or more of the following steps may be carried out in a systematic and controlled fashion: (a) Solution preparation (b) Casting for making of thin-films (c) Folding (d) Compaction (e) Shaping and (f) Coating. Integration and execution of all these steps in a continuous manner is key to overall and continuous making of tablets.

Figure 25:
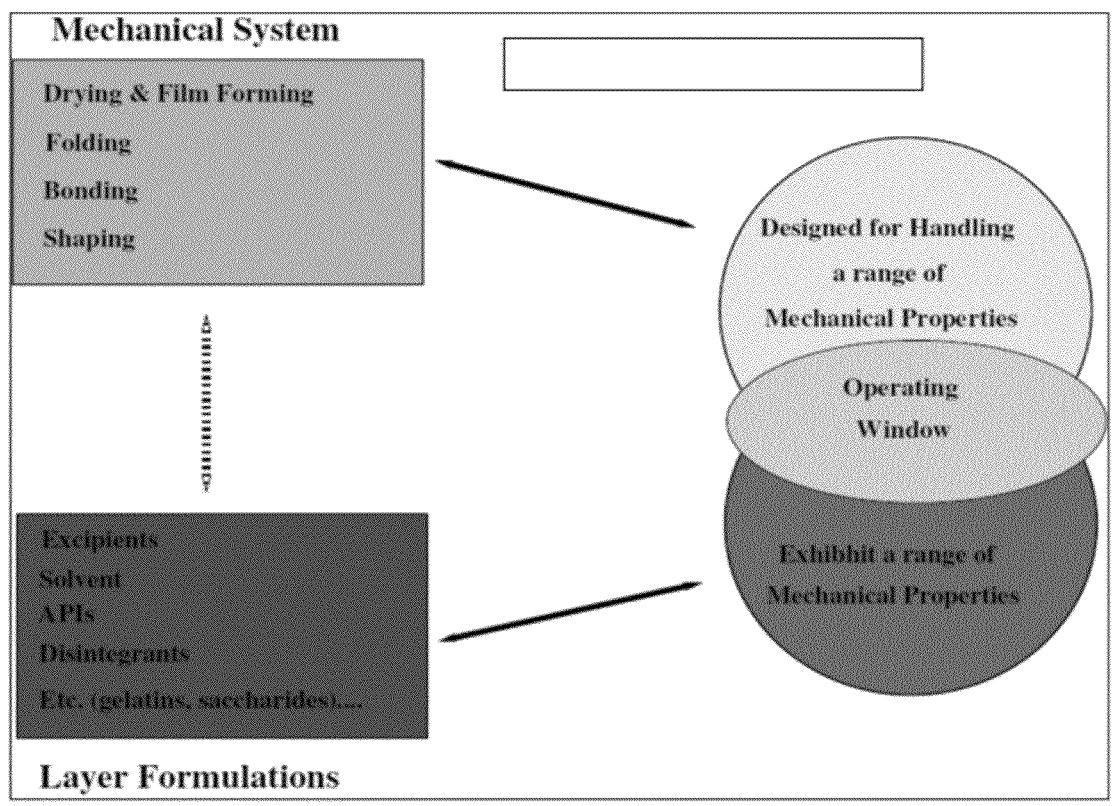
FIG. 25 is an exemplary schematic diagram for the deployment of a mechanical system for converting thin-films into tablets, according to some embodiments.

It was found that, in many cases, thin-films with only certain specific properties can be transformed into tablets through proof-of-concept experiments. The composition of initial solution is the starting point which influences the properties of thin-films, and in particular, mechanical and bonding properties of thin-polymeric-films are affected. The integrated system should be able to operate on thin-polymeric-films with the certain specific properties and be able to transform them into tablets. Thus, design of integrated system is largely based on properties and processing parameters for thin-polymeric-films. FIG. 25 illustrates this concept. Next we first discuss these steps in tablet making in detail and then return to FIG. 25 for a complete example of all steps in an integrated system.

It is worthwhile mentioning that the integrated system shown in FIG. 25 is being designed to operate on 9% PEG formulation which has Elastic Modulus of 323.2 MPa, Tensile Strength of 8.73 MPa % Elongation at break 72.6, and hardness value of 13 MPa. The thin-films which exhibit mechanical properties in a similar range can be successfully converted into tablets by current system (or by slight alterations in the operating points). We shall refer to these properties as a reference film. Whenever, in the example embodiments described herein, a reference to key mechanical properties is made, the implied reference is to (Elastic Modulus, Tensile Strength, % Elongation at break, poisons ratio and hardness).

Casting/Drying:

It has been identified that several properties of formulation/solution are important in successfully casting thin-polymeric-films. The main ingredients of the solution are: Active Pharmaceutical Ingredient (API), Film-forming agent (a base polymer in these examples), Plasticizer and organic or aqueous solvents. Here, we provide qualitative and quantitative details on properties that solution should have:

Chemical Compatibility: It is preferable that the ingredients of the solution are chemically compatible and mix homogeneously.

Viscosity: Solution preferably has high enough viscosity so that solution could be spread out, for HPMC formulation it was found that ballpark viscosity of 2800 mPa·s at room temperature at a shear rate 25 s-1 was noted.

Drying Time: Under regulatory requirements assumed in this example, we required ethanol<0.5% and water %<0.5% in the final films. To achieve this task we limited the drying temperature to be 70 degrees Centigrade and estimated 60 mins to be the minimum time required for drying and film-making. All formulations at initial thin-film thickness of 100 micron and drying time less than this are acceptable.

Figure 27:
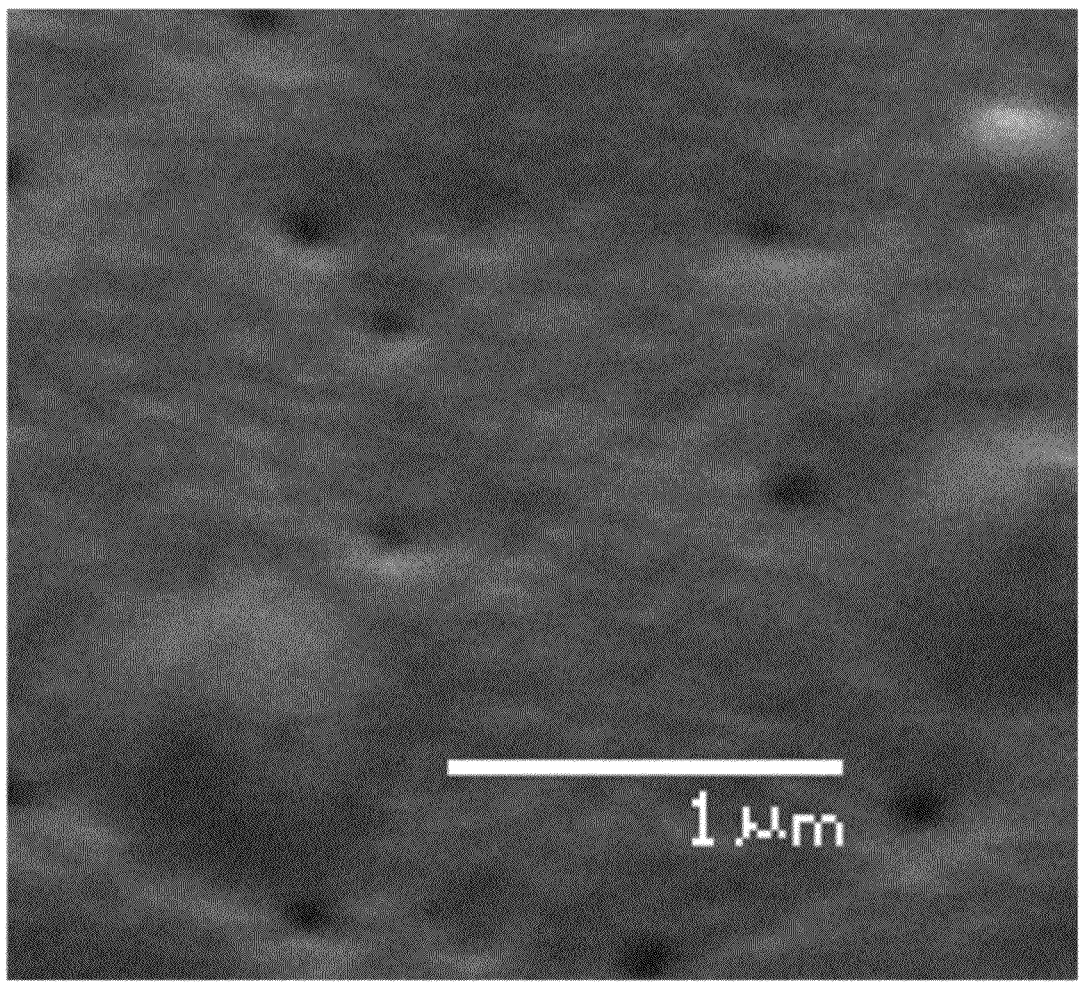
FIG. 27 is an SEM image of polymeric thin-films showing the non-smooth surface and indicating the need of pressure to achieve better overlap, according to some embodiments.

Another aspect of drying process is the quality of film-surface after drying. The bonding of films, in many cases, relies on molecular inter-diffusion and therefore a good bonding is achieved through larger overlapping area of films. In many cases, it is beneficial if the drying process is not overly forced, or else blisters will be formed on the surface and then due to poor film-surface, poor bonding may be achieved. FIG. 27 shows surface asperities on surface of thin-films.

The casting system, such as is illustrated schematically in FIG. 25, may be designed with features such that drying time and rate can be altered depending upon the requirements and is capable of handling a wide-range of properties.

Once the films are formed in casting section; then they are passed into the folding section. The films are peeled-off from the liner at the interface of two sections; and a buffer is provided between the two sections so as to balance any unequal flow-rates of films.

Folding:

First, in embodiments in which multiple members with adjacent surfaces are formed by folding a larger layer, such as a thin polymer film, we have identified that thin-films should have desired flexural properties (or bend ability) so that they don't fail during folding. For several thin-films studied (up to 100 micron thicknesses) this has not been found an issue. Smaller stresses are generated in thin-films and hence folding is achieved without any failure. In particular, for material properties mentioned here-in folding is achieved successfully.

In folding through a roller-mechanism, stations gradually convert a larger thin sheet into a precise layered, prismatic stack. The layered stacks are furthered bonded and shaped. The folding rolls are based on a modular stack design so that roll geometry may be quickly and easily changed. The system can be scaled up with different number of folds. Key Design parameters for folding rollers are:

Bending Radius
Bending Angle
Penetration depth

Figure 31:
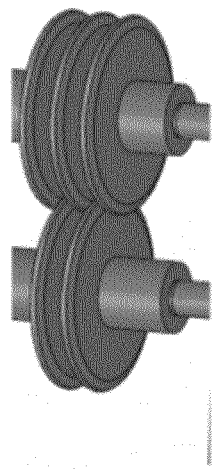
FIG. 31 is an exemplary schematic diagram illustrating a design for achieving folding through rollers by reducing the friction effects, according to some embodiments.

FIG. 31 illustrates one stage of rollers which can be used to fold a film.

Bonding:

We have identified that, in many cases, a certain amount of pressure and dwell time is necessary for polymeric-thin films. In this section, the process parameters and, without being bound by any specific theory of bonding between layers, a description of a suitable bonding mechanism in continuous mode is described.

Figure 26:
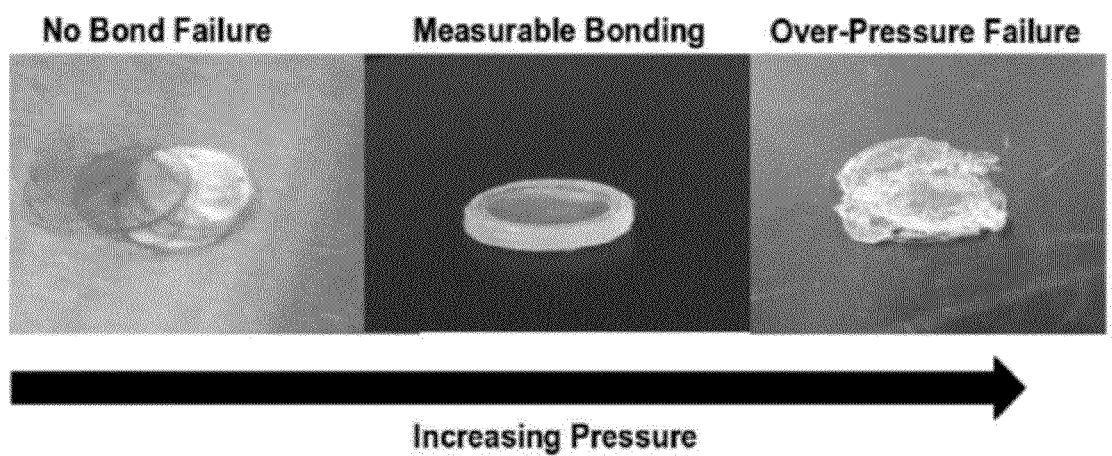
FIG. 26 is a set of exemplary photographs showing the effect of compaction pressure on bonding of thin-film layers, according to some embodiments.

Compaction Pressure: It was found that, in certain cases, certain pressure application is necessary to achieve bonding in between multiple layers of films. The films produced have surface asperities which prevent an overlap or intimate contact between them. Depending on the mechanical properties of films (Young's modulus, hardness, etc.). The goal of the pressure is to cause local plastic deformation for the asperities and achieve very good overlap. Once the overlap is established then inter-molecular diffusion occurs, and bonding starts. The drawback of pressure is that films undergo bulk deformation and strain-hardening. Based on experiments we found that 26 MPa is optimum to bond reference film. FIG. 26 suggests effect of pressure on thin-films. Too low pressure is insufficient to cause bonding, whereas at higher pressures films fail.

Figure 29:
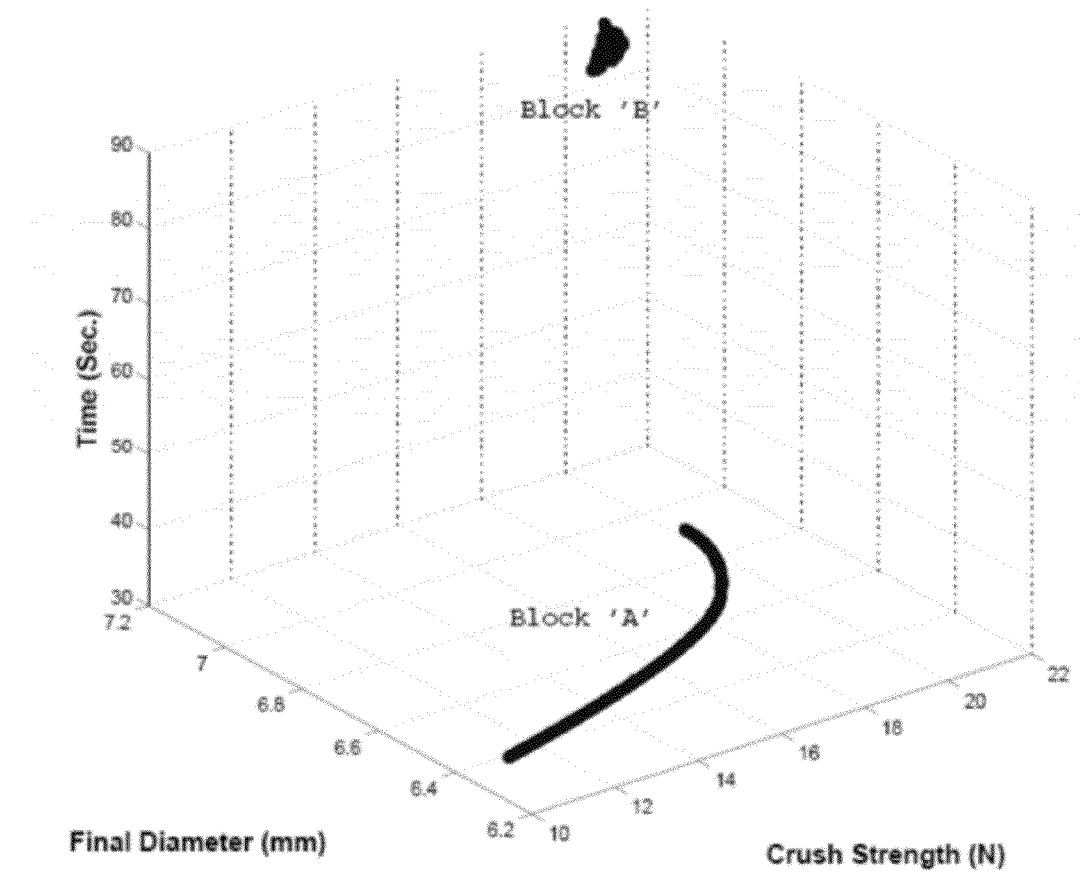
FIG. 29 illustrates sample results for process modeling and optimization of three objectives, according to some embodiments.
Figure 30:
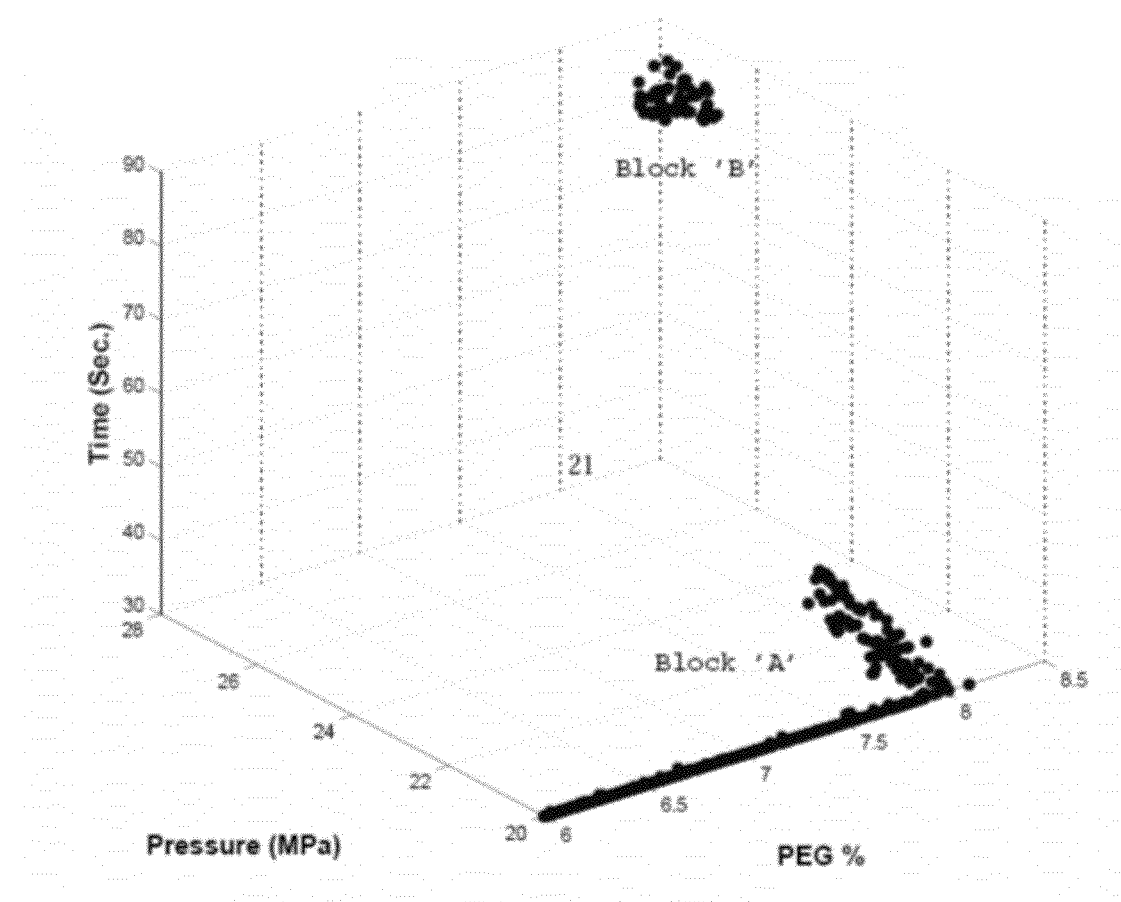
FIG. 30 includes sample results for process parameters yielding enhanced performance, according to some embodiments.
Figure 33:
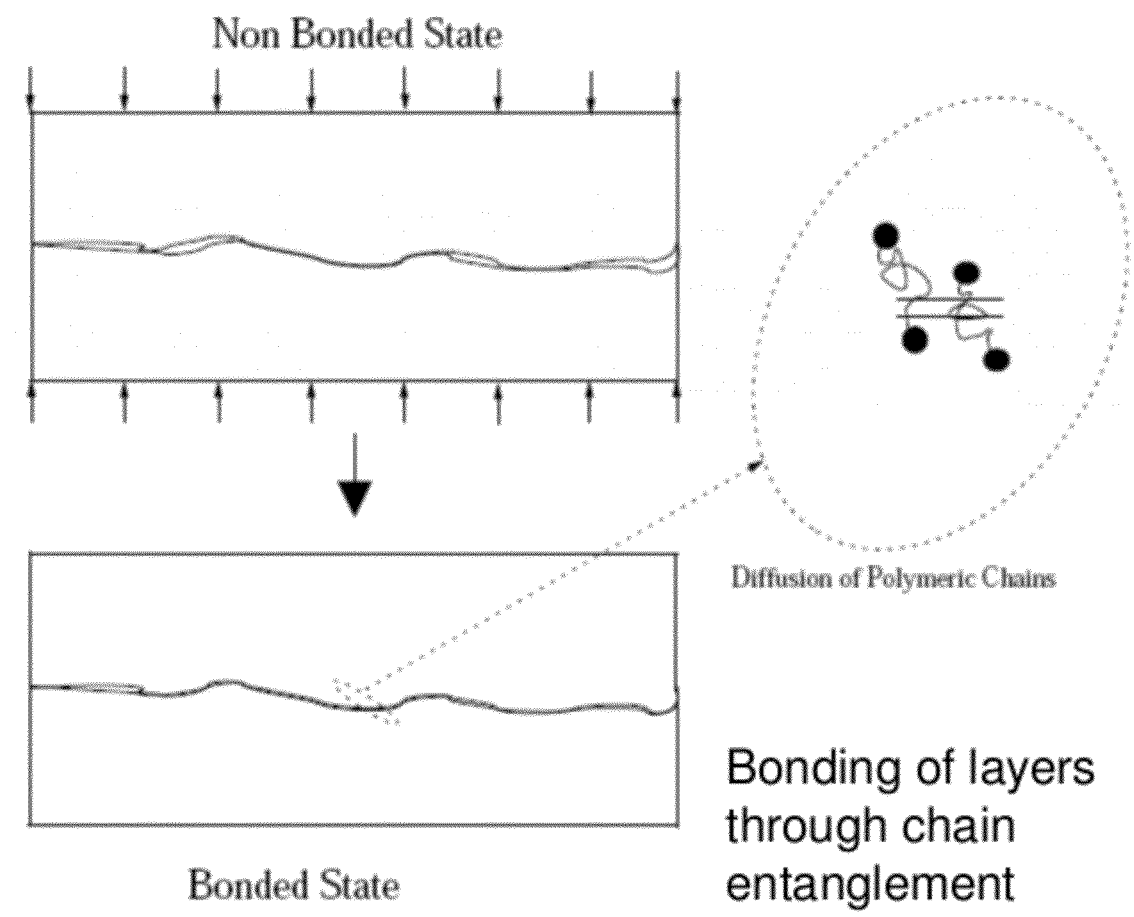
FIG. 33 outlines a conceptual mechanism for bonding of polymeric thin-films, according to some embodiments.

Dwell Time: We found that bonding occurs through intermolecular diffusion and bond-strength increases as time passes by. FIG. 33 shows the bonding mechanism through molecular inter-diffusion. For reference film, we found that for 30 secs. or more a desirable crush strength of 20 N for 6 mm tablets is obtained. For larger dwell times increase crush-strength is marginal. Process modeling and multi-objective optimization was carried out for reference thin-films. The modeled process objectives are shown in FIG. 29 and corresponding process objectives are shown in FIG. 30.

Figure 32:
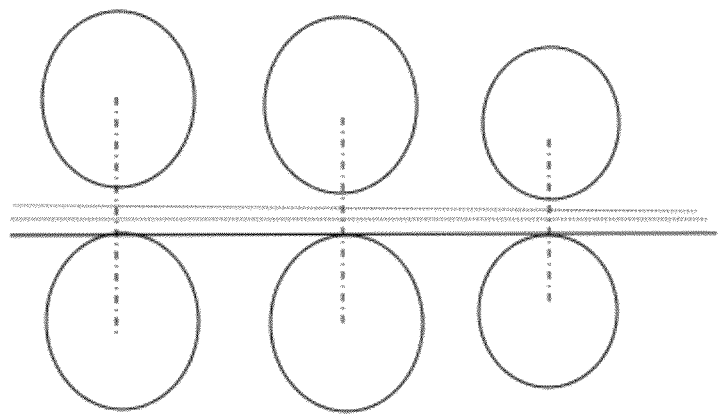
FIG. 32 is an exemplary schematic diagram illustrating a design of multiply reducing rollers for achieving dwell time under specific compaction pressure, according to some embodiments.

Bonding mechanism—in the example embodiment of FIG. 32, a multiple roller reduction strategy for applying incremental pressures and desired dwell time to achieve boding is illustrated. Such a strategy may simplify the application of sufficient pressure and dwell time for bonding. In this multiple reduction strategy pressure is applied incrementally as films are passed through bonding stage. There are several rollers which apply increasing pressure, stationed one after another. By controlling the gap between the rollers incremental pressures can be achieved. The multiple reduction strategy can also be scaled-up as desired.

Residual Stress Issues: It is anticipated that due to friction or pulling there might be some residual stresses in the bonded layers/films. The residual stresses, of too large, can result in de-lamination. Approaches to reducing residual stress may include pulling the films slowly and minimizing friction.

Shaping—In this embodiment, once the layers are bonded they are passed through a pair of shaping rollers which continuously cut out tablets from bonded stack of films. The cavity-profiles within the continuous shaping rollers can be designed such that tablets of desired shapes can be made. An advantage of using mechanical rollers is that a high degree of precision can be achieved on the shapes of the tablets through mechanical-shaping-operation as opposed to any other mode of shaping (heat sealing etc.).

As mentioned earlier, the integrated system of this exemplary embodiment, is designed to operate and transform reference point films into tablets. The default processing parameters are thus set for operating on reference film. For tackling films with properties different from the reference there are two potential strategies that we propose: (a) Modify the system characteristics such that desired processing conditions are achieved, or (b) Alter the properties of films till they fall in the ball-park reference film properties. For practical purposes a combination of both will be needed in most cases. FIG. 25 demonstrates this idea.

The alteration of system characteristics can be done by modifying one or more of the following:
 (a) Throughput rate
 (b) Thickness of films
 (c) Changing the drying conditions
 (d) Folding parameters (bend angles, radius, number of folds, spacing between folding stations)
 (e) Bonding parameters (number of bonding rollers, roller-radius, vertical-gap between rollers, spacing between rollers)

Another important aspect of this system design is that by controlling formulation and film-thickness, desired mechanical properties can be achieved as well as various dosage-sizes (tablets) can be made. In other words, for an amount of API loading the film thickness can be altered and an appropriate number of layers can be folded, bonded and shaped to achieve desired dosage forms.

The design of the system is done such that all elements can be enclosed within an $N_2$ environment. This is important from the stand-point of handling highly hygroscopic API-based films.

Figure 28:
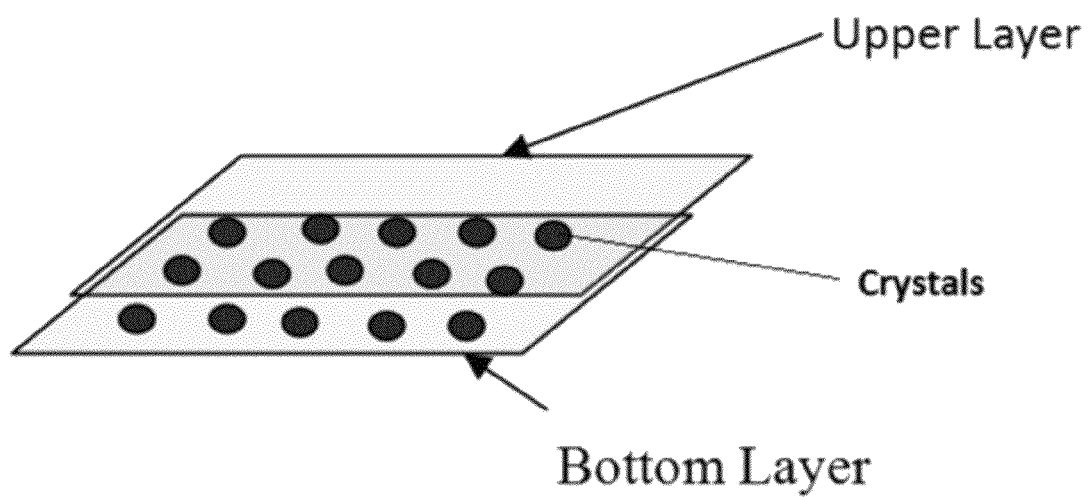
FIG. 28 is an exemplary schematic diagram illustrating the concept of incorporating crystalline APIs within the thin-film polymer layers, according to some embodiments.

Although, the current system tackles thin-films containing amorphous drug dispersed throughout their volume, the current system can be modified to incorporate crystalline APIs. There could be a deposition or growth of crystal on the top surface of films which is could be covered by another layer of film; and subsequent folding, bonding and shaping operations could be performed. FIG. 28 illustrates this concept.

EXAMPLE 3

Figure 34:
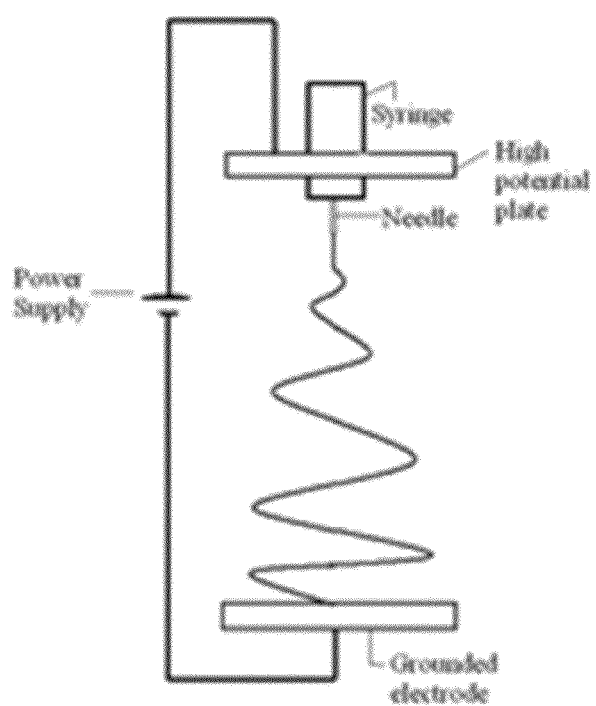
FIG. 34 is a schematic illustration of a single-needle electrospinning apparatus.

This example describes the preparation of films for forming tablets by electrospinning. Solutions of 10 wt % 1.3 MDa Polyvinyl pyrrolidone (PVP) and 5 wt % Aliskiren (SPP), 10 wt % 1.3 MDa PVP and 5 wt % Carbamazepine (CBZ), and 10 wt % 1.3 MDa PVP and 5 wt % Ibuprofen sodium salt (IBU) were prepared. The solutions were electrospun using a single-needle apparatus as illustrated in FIG. 34.

The electrospinning parameters are listed in Table 7:

TABLE 7

| | Electrospinning parameters | | | |
|---|---|---|---|---|
| Drug (wt %) | PVP 1,300,000 MW (wt %) | Flow Rate (mL/min) | Distance (in) | Voltage (kV) |
| IBU, 5% | 10% | 0.01 | 8 | 30 |
| CBZ, 5% | 10% | 0.02 | 8 | 30 |
| SPP100, 5% | 10% | 0.01 | 10 | 23 |

Figure 35:
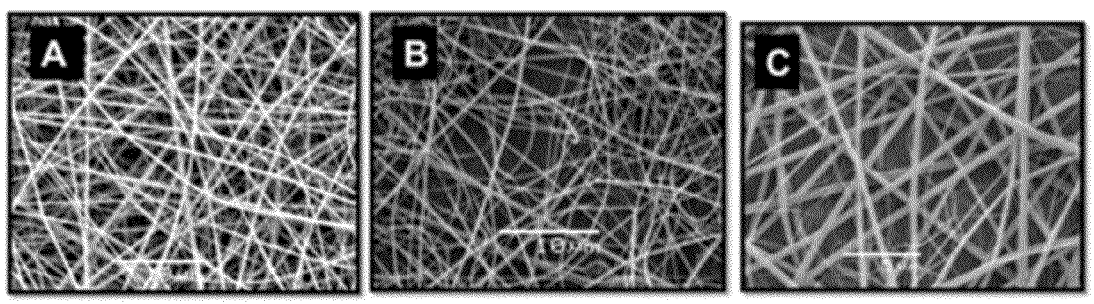
FIG. 35A-C are photographs of electrospun fibers from IBU/PVP (A), CBZ/PVP (B), and SPP/PVP (C).
Figure 36:
FIG. 36 illustrates CBZ/PVP tablets compressed using a Carver Press.

The electrospun fiber mats were characterized by scanning electron microscopy. The images are shown in FIG. 35A-C Approximately 40 mg of the resulting electrospun mats were rolled, folded and packed into a die for compression. They were compressed using a Carver Press with 2 MT pressure and a hold time of 10 s. Examples of the resulting tablets are shown in FIG. 36.

Figure 37:
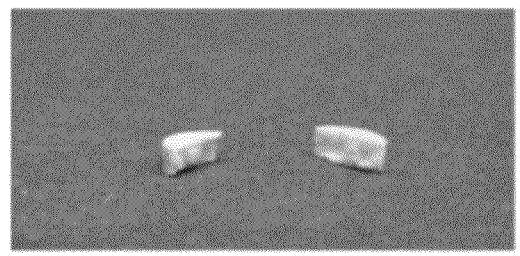
FIG. 37 illustrates CBZ/PVP tablets after hardness test.

The CBZ/PVP tablets and IBU/PVP tablets were tested for hardness. The CBZ/PVP tablets had an average hardness of 221 N and primarily failed by breaking in half (FIG. 37).

Figure 38:
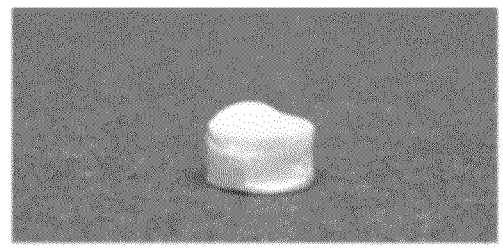
FIG. 38 illustrates IBU/PVP tablets after hardness test.

The IBU/PVP tablets had an average hardness of 81 N and primarily failed by squishing and lamination (FIG. 38):

Dissolution tests were performed on all three formulations. The parameters are shown in Table 8:

TABLE 8

| | Parameters for Dissolution Testing | | | | |
|---|---|---|---|---|---|
| Drug | Media | Apparatus | Temperature | Paddle Rate | Number of tablets tested |
| IBU | Phosphate Buffer, pH 10 | I | 37° C. | 100 rpm | 3 |
| SPP | 0.01N HCl | I | 37° C. | 100 rpm | 3 |
| CBZ | 1 wt % SDS in Water | II | 37° C. | 75 rpm | 3 |

Figure 39:
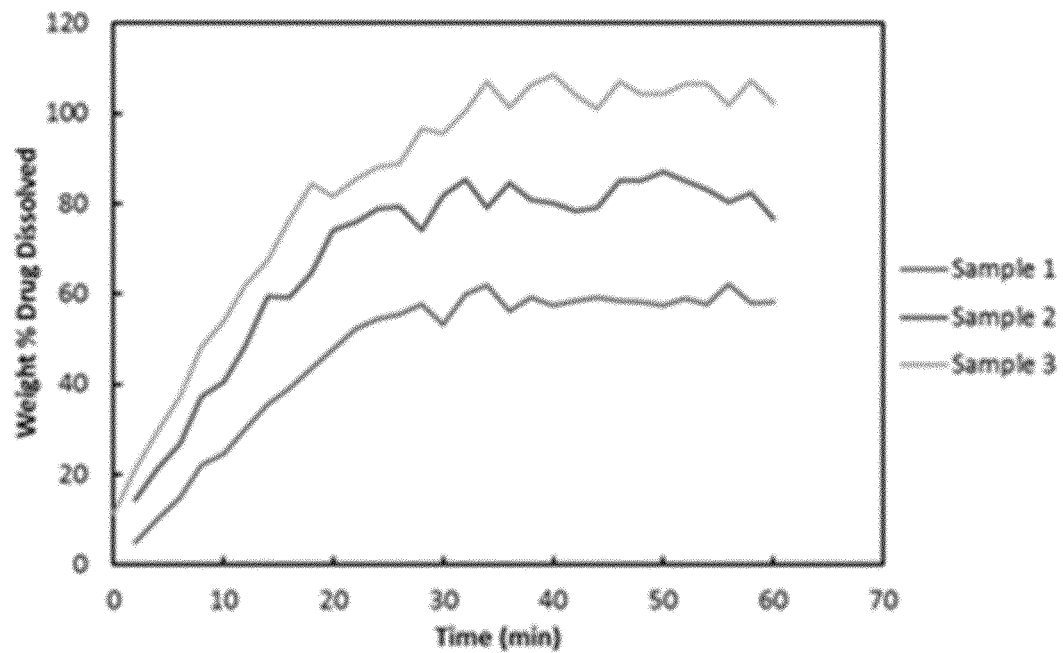
FIG. 39 illustrates Weight Percent IBU released from tablets prepared from electrospun mats as a function of time during dissolution tests.

The dissolution testing results for the IBU/PVP tablets prepared from electrospun mats are shown in FIG. 39.

Figure 40:
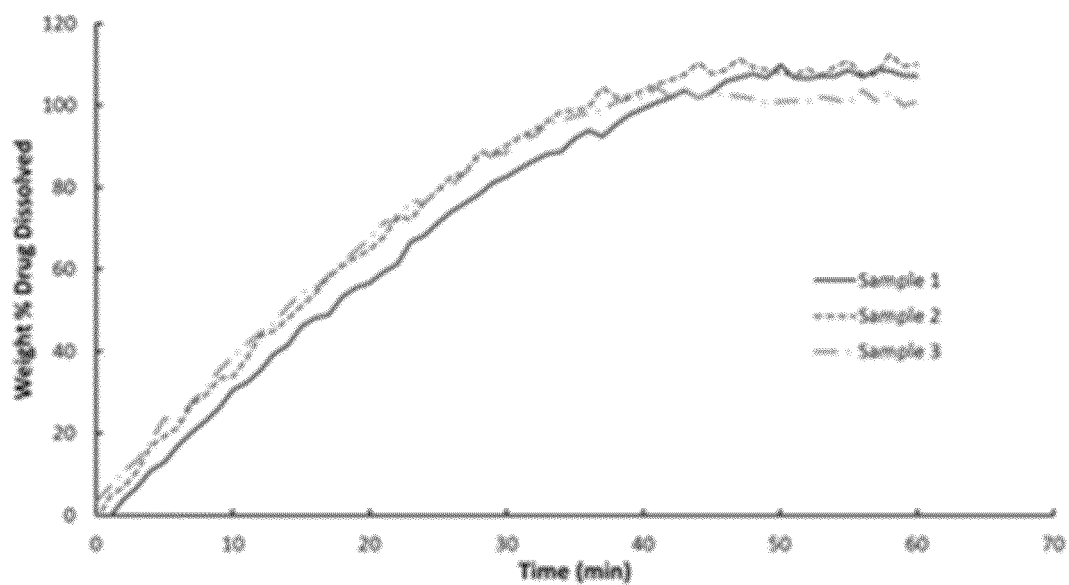
FIG. 40 illustrates Weight Percent SPP released from tablets prepared from electrospun mats as a function of time during dissolution tests.

The dissolution testing results for SPP/PVP tablets prepared from electrospun mats are shown in FIG. 40

Figure 41:
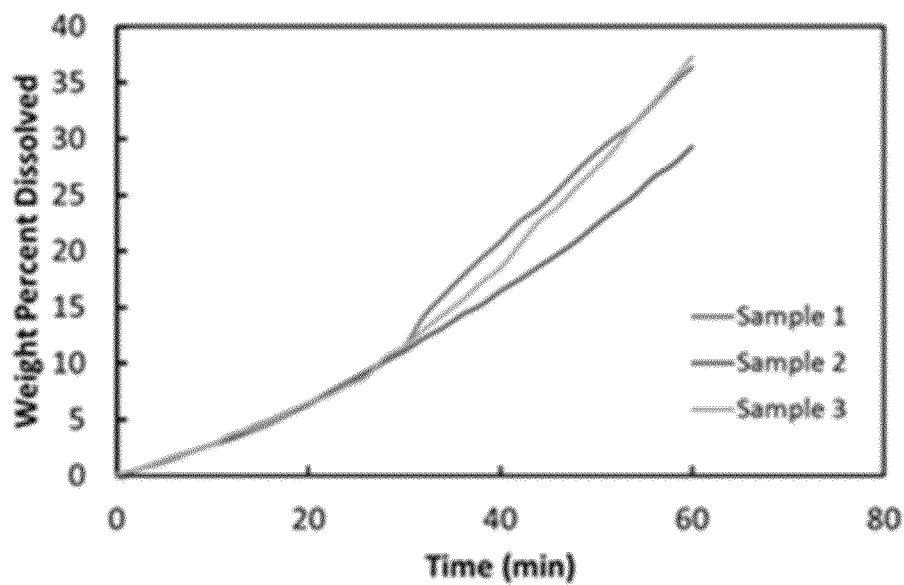
FIG. 41 illustrates Weight Percent CBZ released from tablets prepared from electrospun mats as a function of time during dissolution tests.

The dissolution testing results for CBZ/PVP tablets prepared from electrospun mats are shown in FIG. 41.

EXAMPLE 4

This example describes the preparation of films for forming tablets by electrospraying. Electrospraying is the atomization of a liquid into a spray of fine charged droplets of sizes ranging from several microns down to a few nanometers, brought about by a suitably strong applied electric field. As a process, it can offer several advantages over other mechanical means of atomization and charging of liquids to form charged droplets. It can bring about the atomization of a liquid under the influence of an electric field into extremely fine (nanometers to microns in size) charged droplets. The droplets can be much smaller in size than obtained by other mechanical means of atomization and typically show a bimodal size distribution (primary and secondary droplets). The resulting spray is usually self-dispersing in space due the electrostatic repulsion between similarly charged droplets and the fine nature of the droplets offers a large interfacial area for mass transfer and hence, efficient and quick drying. Thus, electrospraying of solutions containing dissolved solids in a suitable solvent can produce fine droplets that very quickly solidify and dry into solid nano/micro particles. Electrospraying may thus be conveniently used to formulate solid drug-excipient micro/nano particles exhibiting characteristic and controllable dissolution profiles depending on their size and composition. Such drug micro/nanoparticles are also expected to result in better bioavailability of the drug substance. When these particles are used to formulate solid products, the resulting solid formulations (tablets, capsule etc.) are expected to show characteristic dissolution properties.

Figure 42:
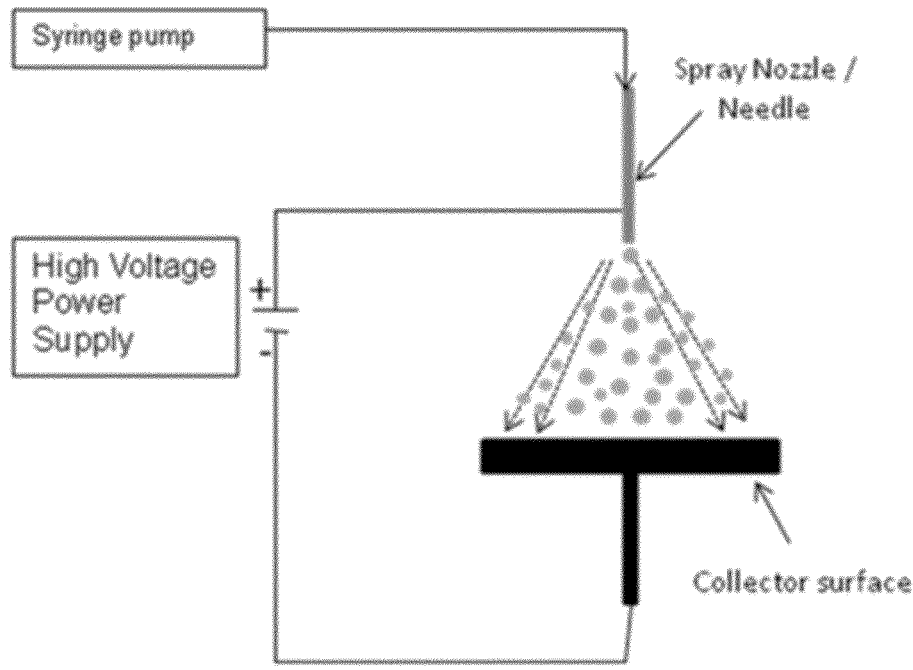
FIG. 42 illustrates Electrospraying Apparatus.

An example of a suitable electrospraying apparatus is provided in with FIG. 42.

Formulation of Novel Solid Formulations Using Electrospraying

Electrospraying can allow for the formulation of solid particles from the corresponding liquid solutions. While the fine nature of the droplets can ensure quick solidification and drying into nano/micro particles with unique properties, the resulting fine powder can be, in many cases, very difficult to handle. Such fine charged powders exhibit poor flow properties, in many cases. The charge can cause dispersion of the powder with particles flying around due to repulsion between similarly charged particles. This is seen from the divergent nature of the electrospray. Conventional solids handling may not be suitable to formulate solid products from such charged fine powders, in many cases. Further, conventional solids handling is generally labor intensive and discontinuous in nature and results in wastage of material and valuable processing time. It would be advantageous to exploit electrospraying as a means to fabricate drug nano/micro particles and also to directly formulate the final dosage form from constituent drug nano-micro, circumventing conventional solids handling.

Figure 43:
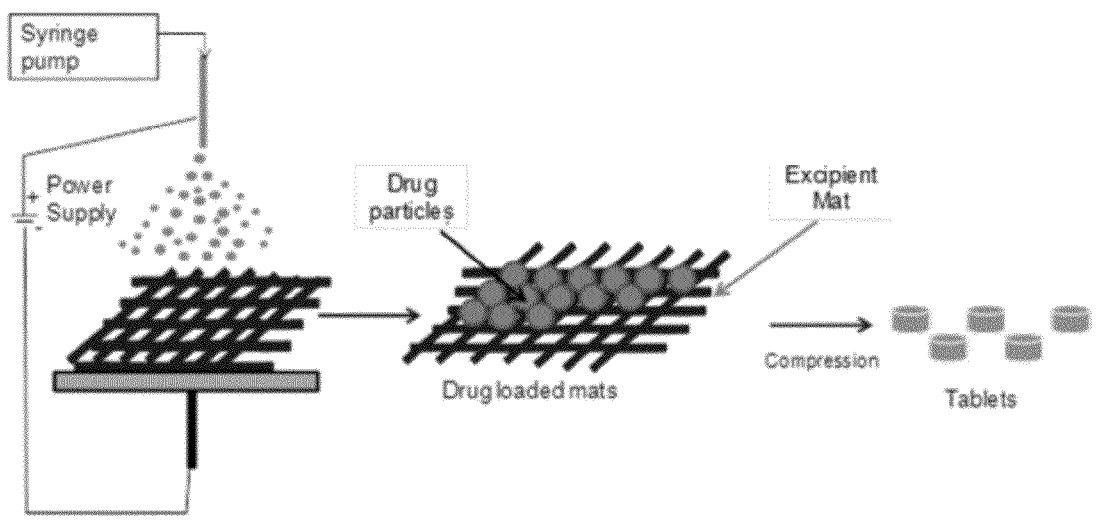
FIG. 43 illustrates schematically formulation of drug loaded excipient mats.

An approach (as outlined in the schematic of FIG. 43) involves electrospraying a solution of the API in a suitable solvent directly onto a pre-fabricated excipient mesh or excipient sheet or mat of other suitable composition. Without being bound by any particular theory of operation, the particles are expected to adhere to the fibers or get caught in the intermediate spaces or pores in the mesh network of a mat as shown in the schematic of FIG. 43. Such drug loaded excipient mats can then be either administered directly or further processed by stacking one over the other, folding, rolling and compressing into tablets. In some embodiments, such mats may be used as the layers described above processed using techniques as described herein to form an article serving as a pharmaceutical product or precursor therefore.

Direct spraying on pre-made excipient mats will allow continuous dispensation of one or more drugs onto a suitable excipient without having to worry about focusing for controlled deposition of electrosprayed particles or post fabrication handling of these particles. Multiple nozzles may be used in this case to ensure uniform spraying over large areas in a continuous manner. In some embodiments, electrospinning and electrospraying may be used in conjunction to alternately fabricate fiber mats by electrospinning and spray drug particles onto these by electrospraying in a layer by layer manner. We can further use such controlled deposition to deposit multiple drugs and excipients at different locations to create novel formulations designed to bring about controlled release of APIs. Such direct formulation of solid product from liquid solutions is expected to greatly simplify Pharmaceutical Operations, eliminating tedious, multiple processing steps. Experiments involving the fabrication of such drug loaded excipient mats using electrospraying, conversion of such mats to tablets and characterization of drug release from such tablets are noted below.

Experiment 1: Electrospraying of API onto Excipient Mats to Make Tablets

Aim:

To study electrospraying of a drug substance onto a pre-fabricated excipient mat Chemicals:

Carbamazepine, SPP 100, Polyvinylpyrrolidone (MW≈1,300,000), ethanol and methanol Experimental Procedure:

A non-woven PVP mat was fabricated by electrospinning a PVP mat from a solution of PVP in a mixture of ethanol and methanol (2 gmPVP+10 ml Ethanol+5 ml Methanol). The imposed flow rate was 0.1 ml/min and the applied voltage between the needle and a collector placed 20 cm away was 25 kV. 10 ml of the solution was filled into a syringe and spun into a mat. Methanol was added to the solution to reduce solution viscosity and to prevent gelling and clogging of needle. The mat was taken off the aluminum collector and weighed. The weighed mat was now placed on a new piece of aluminum foil. PVP is hygroscopic in nature and hence, the mats must preferably be stored in a desiccator and should be weighed just before electrospraying the drug substance onto the mat to ensure that the mass of API sprayed is recorded accurately.

Electrospraying of Carbamazepine:

Experiments involving CBZ showed that spherical particles of CBZ could be obtained by electrospraying solutions of CBZ in methanol. These particles appeared to be in a non-crystalline state as observed from their SEM images. CBZ dissolved in methanol (5 wt %) was chosen as the solution for electrospraying CBZ onto our PVP mats. 5 wt % solutions are close to saturation, ensuring a reasonably high rate of CBZ deposition without crystallization or solidification onto the spray nozzle. CBZ was sprayed for a fixed period of time (60 minutes). The drug loading may be controlled by varying the time period of drug electrospraying. These mats were further compressed into tablets using a Carver Press to yield tablets with varying drug loading (1-15 wt %).

Electrospraying of SPP 100:

Initial experiments with electrospraying of ethanolic solutions of SPP 100 showed that it was difficult to obtain smooth spherical particles. Typically, pear shaped particles and q-tips were formed. The shape and size of the particles obtained may be controlled by controlling the drying conditions or solution properties. In a subsequent experimental setup, the drying conditions are dictated by the external environmental conditions. Thus, we resorted to altering the solution properties by incorporating PVP in the solution. A variety of solutions of PVP and SPP 100 in ethanol yield smooth spherical particles. For the present experiments, a highly concentrated solution of SPP 100 was desired so as to ensure maximum solid deposition for the operational flow rate. We used a solution containing 3 gm SPP 100, 2 gm PVP (MW≈10,000) in 10 ml Ethanol and 2 ml Methanol. Methanol was added to reduce solution viscosity. The solution was sprayed at a flow rate of 0.01 ml/min with a potential difference of 26.9 kV applied between the spray nozzle and the aluminum foil (onto which the PVP mat was placed) placed at a distance of 25 cm. The time period for spraying onto each mat was calculated to achieve a desired drug loading by depositing a required amount of SPP 100. Tablets ranging in drug loading from 10 wt % to 50 wt % SPP100 were created.

Figure 44A:
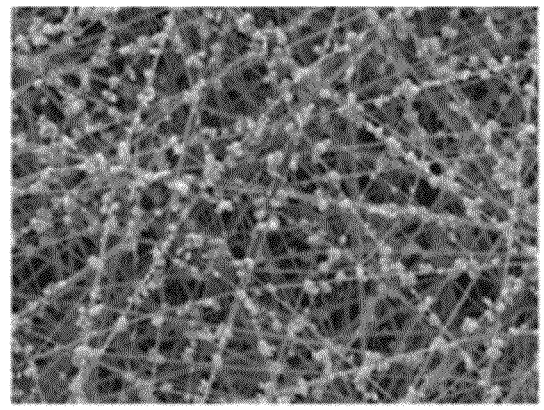
FIGS. 44A and 44B are photographs of a) CBZ electrosprayed onto PVP mats b) SPP 100 electrosprayed onto PVP mats.
Figure 44B:
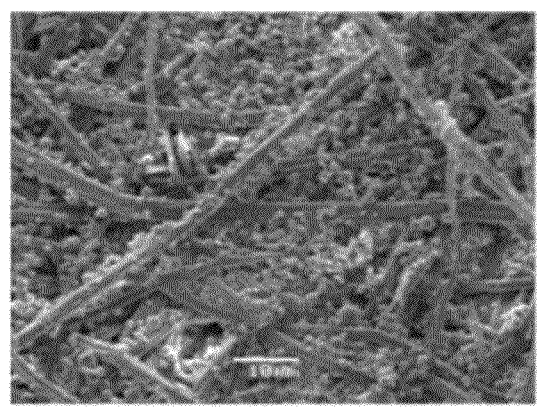
Figure 45:
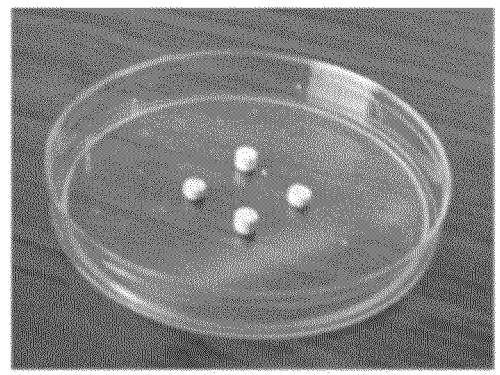
FIG. 45 illustrates CBZ loaded PVP tablets.

Observations:

In FIG. 44, particles of CBZ (about 1 µm in size) are observed to adhere to the fibers. Similarly particles of SPP 100 (about 2-3 µm in size) were observed to be deposited onto the PVP mats as seen from the SEM image on the right. These mats were compressed using a dye on a Carver press or a tablets press to a thickness of about 4 mm and diameter of 9 mm, as illustrated in FIG. 45.

Conclusion:

Active Pharmaceutical Ingredients may be electrosprayed onto pre-fabricated solid substrates such as electrospun mats that may be further processed into solid products such as tablets. Such electrospray deposition of the API offers a convenient solution to solid product formulation without requiring the design of complex electric fields for focusing.

Experiment 2: Dissolution Testing of SPP 100 Loaded PVP Tablets

Aim:

To study the dissolution profile of SPP 100 tablets formulated by compressing SPP 100 loaded electrospun PVP mats Experimental Procedure:

SPP 100 loaded electrospun PVP were fabricated by electrospraying SPP 100+PVP solutions as described in Experiment 1. For dissolution testing, tablets with an approximate drug loading of 30-40% by weight were selected. SPP 100 dissolution testing makes use of the basket method with SPP 100 absorbing at 279 nm An automated dissolution testing apparatus (Cooney Lab) was employed for the test. Three tablets fabricated from a SPP 100 loaded PVP mat (with approximate drug loading of 30-40 wt %) were used for the dissolution test. The tablets were introduced into the baskets and immersed in individual sinks maintained at 37° C. A 0.01N hydrochloric acid solution was used as the dissolution medium. The speed of rotation for the baskets was set at 100 rpm. The absorbance measurement of the dissolution medium is proportional to the concentration of SPP 100 in the medium and is measured at 0.8 minute intervals. A standard solution containing a known amount of SPP 100 was used to calibrate the absorbance against concentration. A detailed description of the procedure for preparation of standard solution and operation of the apparatus may be found in the operating manual. The output data recorded in the experiment is a plot of the absolute (or percentage absorbance) against time.

Observations and Discussion:

We used a single PVP mat with a drug loading of about 40 wt %. The mat was cut into smaller parts, each weighing about 300 mg. It is difficult to weigh out exactly 300 mg sections of the mat, with the tools used of this experiment, and hence the corresponding tablets made from these mats weighed roughly 300 mg. Further, each of the sections formed did not have the same drug loading (since the spraying of the SPP-PVP particles on the mat is not exactly uniform). This results in variation of drug loading from one tablet to another. The exact drug loading for each tablet may be calculated by determining the absorbance at complete dissolution and comparing it with the absolute absorbance as measured for the standard solution of known concentration. However, in other embodiments, less variation may be achieved.

|  | Tablet 1 | Tablet 2 | Tablet 3 |
| --- | --- | --- | --- |
| Total Mass of Tablet (mg) | 295.5 | 283.7 | 294.4 |
| Mass of SPP 100 in Tablet (mg) | 112.6 | 94.5 | 95.1 |
| % Drug Loading | 38.1 | 33.3 | 32.3 |

Figure 46:
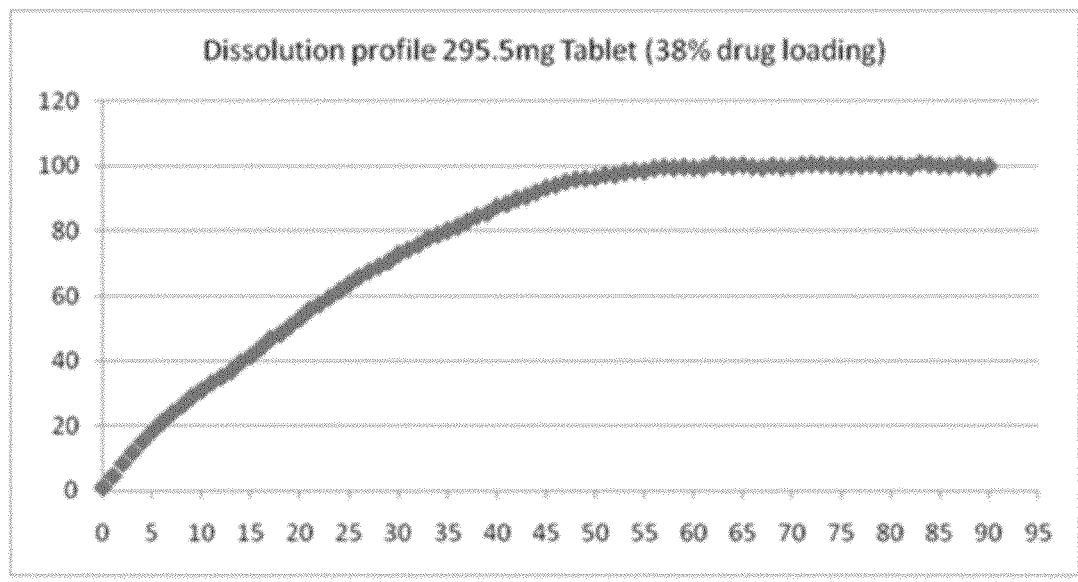
FIG. 46 illustrates a drug release profile for tablets formulated from SPP100 loaded PVP mats.

The tablets were observed to dissolve completely in about 50-60 minutes as observed from the dissolution profile shown in FIG. 46 for 'Tablet 1'. The x-axis is the time in minutes while the y-axis is the percentage absorbance.

300 mg tablets with 50 wt % drug loading are used as the market formulation for SPP 100. These are observed to dissolve completely in about 40-45 minutes. Thus while our formulation does not dissolve as fast as the market formulation, the value is still in the same ballpark and can be tuned to achieve faster dissolution. In commercial production, a mechanism for uniform deposition of the electrosprayed material onto the excipient mats may be employed to eliminate the variability arising after a given mat is cut into cross sections to formulate tablets. Alternatively, mats can be cut into preweighed sections and the drug can be electrosprayed onto these pre-cut sections for a specified period of time to eliminate this variation.

We also observe that a substantial amount of the electrosprayed material is deposited onto the aluminum foil as the particles pass through the interstitial spaces between the network of fibers in the electrospun mat. This not only results in wastage of substantial amounts of API, but also makes it impossible to estimate the drug loading of the mats without actually weighing the mats before and after electrospraying the drug substance. One or more suitable techniques may be used to circumvent this problem, including:

a) Make the mat thicker so that more number of fibers now form a dense network with smaller interstitial gaps, resulting in better trapping of the electrosprayed particles b) Instead of using non-woven mats with random interstitial gaps, use woven mats with well defined interstitial gaps of a size smaller than that of the particles c) Use continuous films of the excipient material instead of woven or non-woven mats that ensure that none of the API lands on the aluminum foil.

Conclusions:

Through this experimental study we have demonstrated that APIs may be electrosprayed onto solid substrates (excipient mats) that can be handled more readily and further processed into the final solid dosage form (tablets). The experiment shed light on a number of practical problems such as uniformity of deposition and apriori prediction of drug loading.

Figure 47:
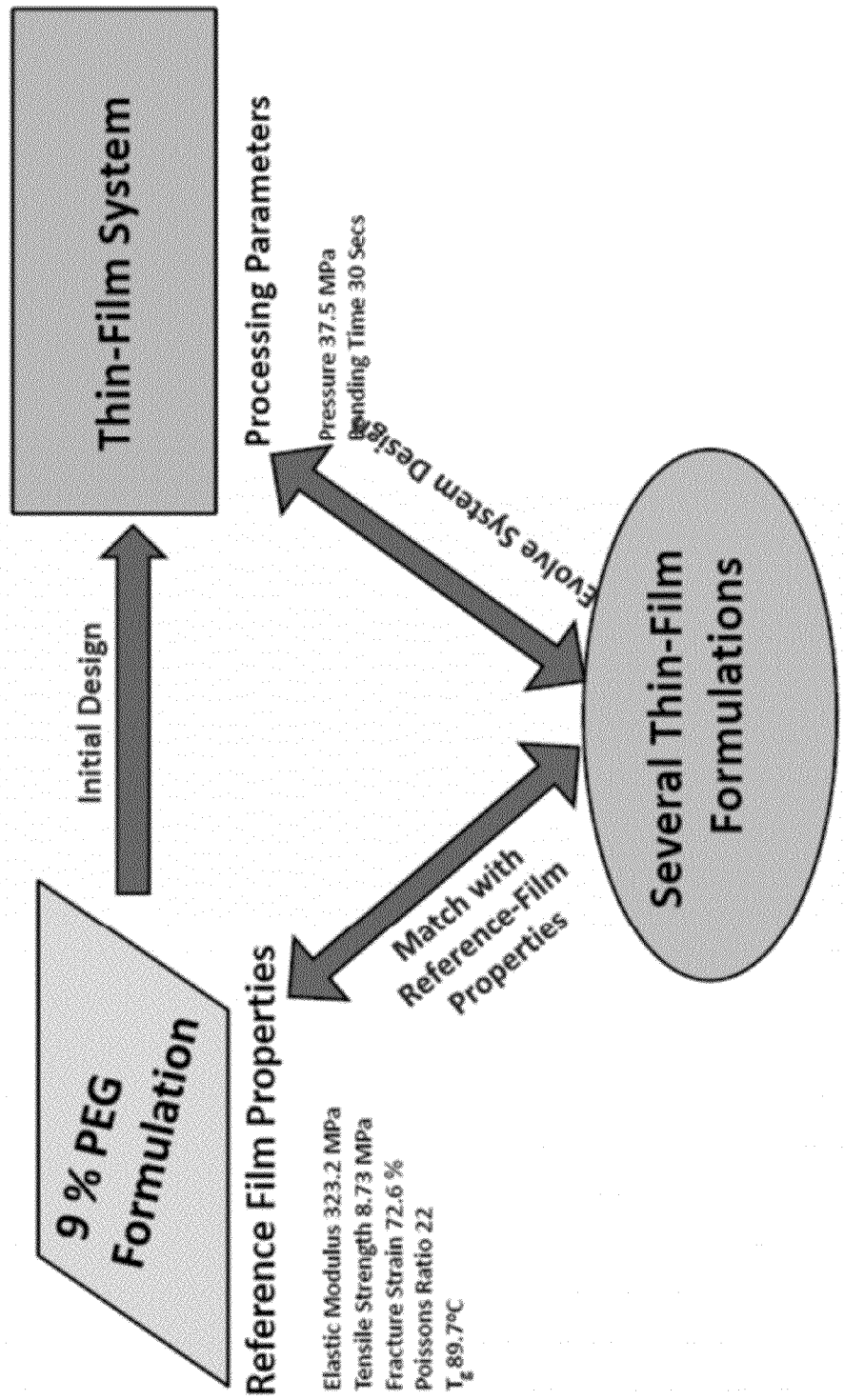
FIG. 47 is a conceptual illustration of an approach for refining a manufacturing system using layers.
Figure 48:
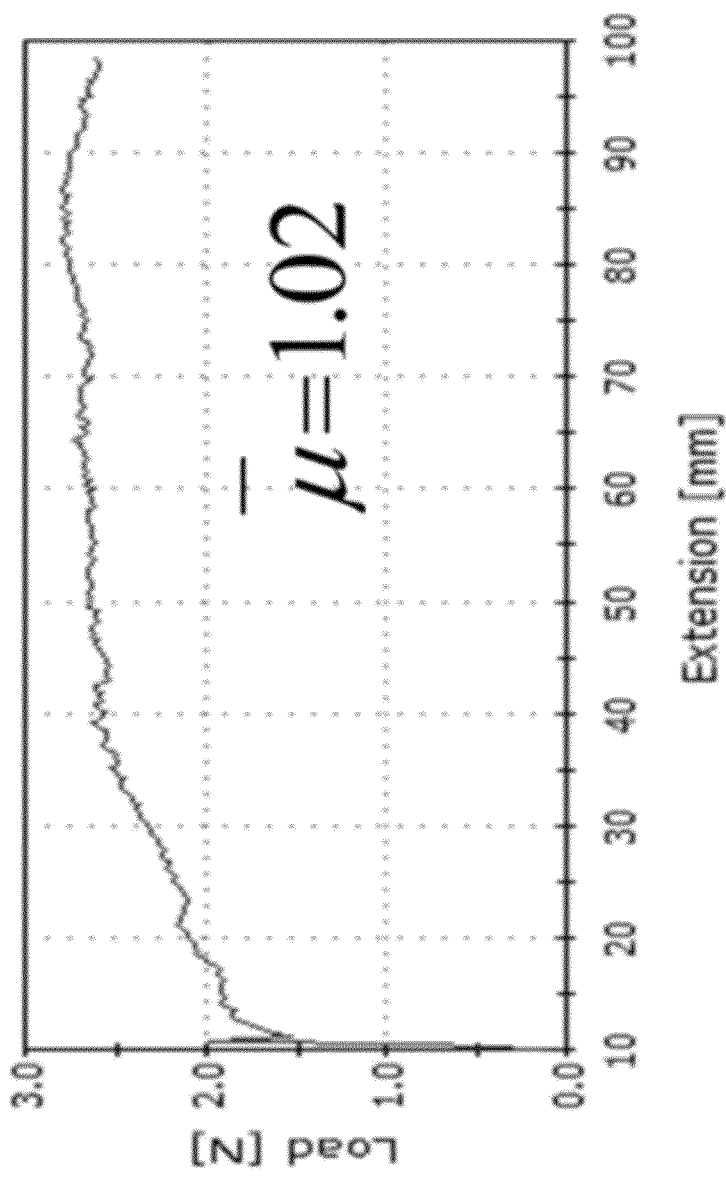
FIG. 48 is a graph of a mechanical property of a thin film, incorporating a pharmaceutically active composition and manufactured using a system as described herein.
Figure 49:
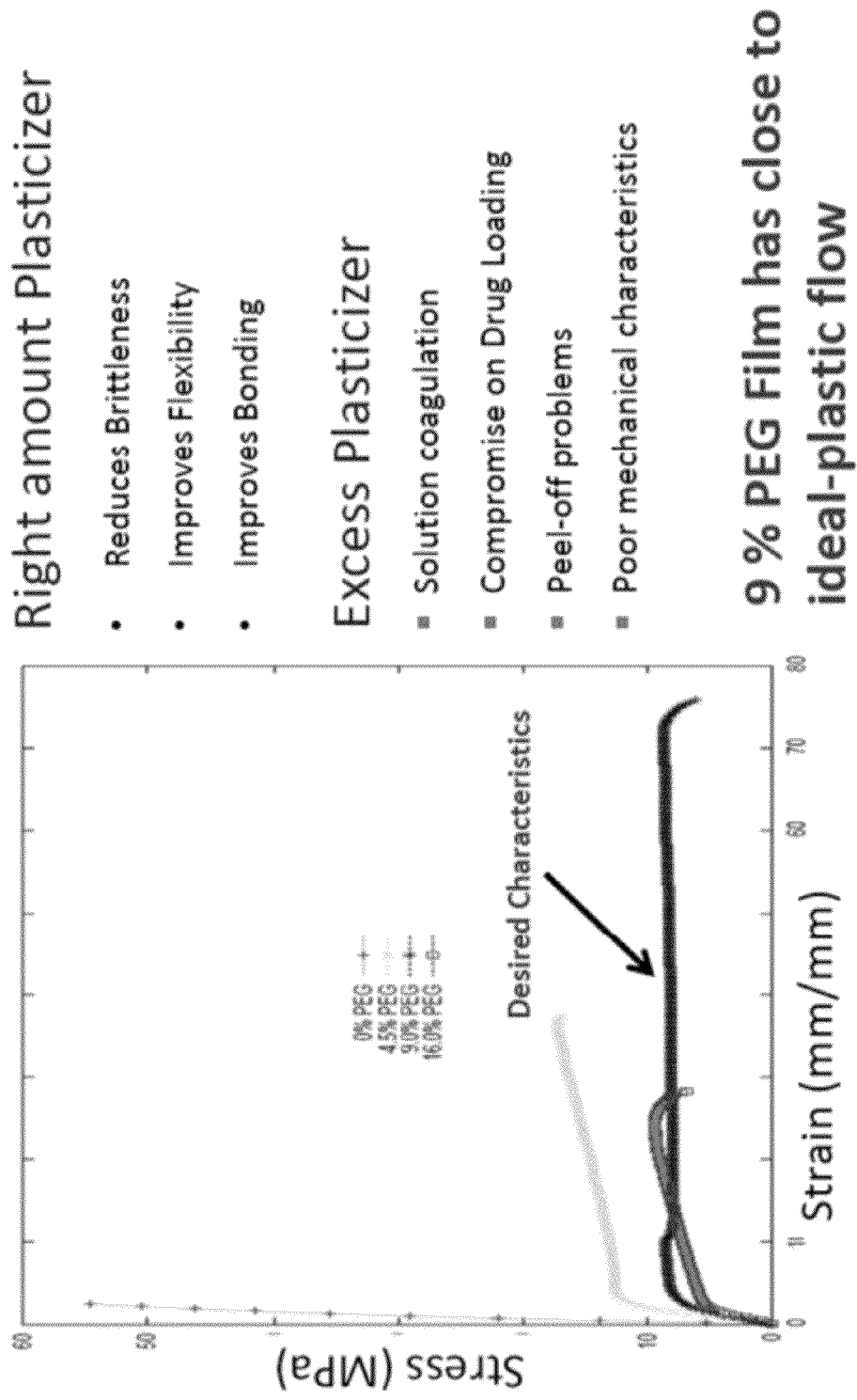
FIG. 49 is a graph illustrating selection of a suitable amount of plasticizer (9% PEG in this example).
Figure 50:
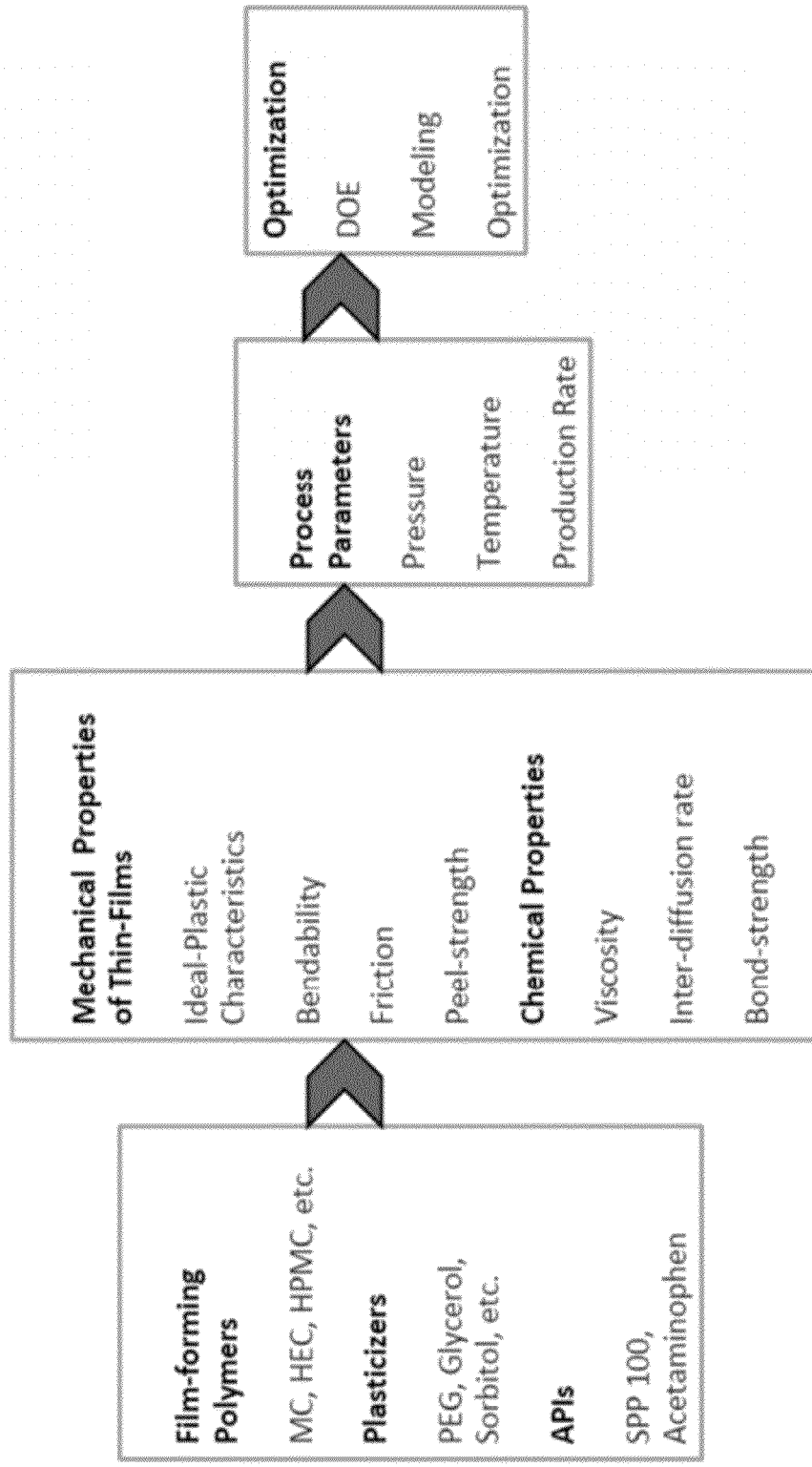
FIG. 50 is a schematic illustration of a thin film table manufacturing plan.

FIGS. 47-50 provide an example of how the above teachings may be applied. FIG. 47 is a conceptual illustration of an approach for refining a manufacturing system using layers. In this example, a formulation using 9% PEG is illustrated as providing reference properties. However, it should be appreciated that this value is not a limitation on the invention. For example, in some embodiments, a value approximately equal to 9%, such as a % of PEG in the range of 8.8 to 9.2, may be used. Though, in other embodiments, the percentage of PEG need not approximate 9% and in other embodiments, PEG may not be used at all. FIG. 48 is a graph of a mechanical property of a thin film, incorporating a pharmaceutically active composition, manufactured using a system as described herein. FIG. 49 is a graph illustrating selection of a suitable amount of plasticizer (9% PEG in this example). FIG. 50 is a schematic illustration of a thin film table manufacturing plan.

U.S. Provisional Patent Application Ser. No. 61/480,756, filed on Apr. 29, 2011, and entitled "Layer Processing for Pharmaceuticals" is incorporated herein by reference in its entirety for all purposes.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention.

For example, though it is described herein that a single large sheet is manipulated to allow bonding together of different portions of the layer to form an article, it is not a requirement that the multiple portions be initially formed from a single sheet. Multiple separate sheets may be positioned with their surfaces adjacent to each other, and these sheets may have different API's. Moreover, even when multiple sheets are used, the sheets may be manipulated as described herein to increase the thickness of the article produced.

Also, it is described that in some embodiments, the layer is consolidated. Such consolidation may result in bonding of the planar members to each other to form a unitary article. Such consolidation may alternatively or additionally result in removal of air, solvent or otherwise increase the density of the article. Though, it should be appreciated that bonding and increasing the density may be performed in the same or separate manufacturing operations.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for manufacturing an article comprising an ingestible pharmaceutical product or a precursor thereof, comprising:

producing a pharmaceutically active composition from a precursor by reacting the precursor within a fluid to form the pharmaceutically active composition;

depositing the fluid comprising the pharmaceutically active composition on a substrate;

forming a layer comprising the pharmaceutically active composition, the layer having an elongated dimension;

manipulating the layer about its elongated dimension to form the article, wherein an average thickness of the article is at least about two times an average thickness of portions of the layer used to form the article; and bonding adjacent portions of the layer into a unitary structure, wherein forming the layer comprising the pharmaceutically active composition comprises removing material deposited with the fluid from the substrate.

2. A method as in claim 1, wherein manipulating the layer about the elongated dimension comprises folding at least a portion of the layer across the elongated dimension such that a first portion of a surface of the layer is folded onto a second portion of the same surface.

3. A method as in claim 2, wherein manipulating the layer comprises folding at least a portion of the layer to produce at least one crease.

4. A method as in claim 1, wherein the layer comprises a first surface and a second, opposite surface, and manipulating the layer comprises bringing at least a portion of the first surface into contact with at least a portion of the second surface.

5. A method as in claim 4, wherein manipulating the layer about the elongated dimension comprises rolling at least a portion of the layer around an axis parallel to the elongated dimension.

6. A method as in claim 1, wherein the ingestible pharmaceutical product comprises a tablet.

7. A method as in claim 1, wherein the pharmaceutically active composition comprises an amorphous composition.

8. A method as in claim 1, wherein the pharmaceutically active composition comprises a crystalline composition.

9. A method as in claim 1, wherein the layer has an average thickness of less than about 1 mm.

10. A method as in claim 1, further comprising drying the layer.

11. A method as in claim 1, wherein the layer comprises polyethylene glycol.

12. A method as in claim 1, further comprising applying a compressive force to at least a portion of the layer.

13. A method as in claim 1, wherein bonding adjacent portions of the layer into a unitary structure comprises applying a compressive force to bond adjacent portions of the layer into the unitary structure.

14. A method as in claim 1, wherein the layer is a free standing layer.

15. A method as in claim 1, wherein the pharmaceutically active composition extends through the layer such that a first surface and a second surface, opposite the first surface, contain the pharmaceutically active composition.

16. A method as in claim 1, comprising combining an excipient with the fluid used to form the layer.

17. A method as in claim 1, comprising forming the precursor in the fluid.

18. A method as in claim 1, wherein depositing the fluid containing the pharmaceutically active composition to form the layer comprises casting the fluid.

19. A method for manufacturing an article comprising an ingestible pharmaceutical product or a precursor thereof, comprising:

depositing a fluid comprising a pharmaceutically active composition on a substrate;

forming a layer comprising the pharmaceutically active composition, the layer having an elongated dimension;

manipulating the layer about its elongated dimension to form the article, wherein an average thickness of the article is at least about two times an average thickness of portions of the layer used to form the article; and bonding adjacent portions of the layer into a unitary structure, wherein depositing the fluid comprising the pharmaceutically active composition comprises electro spinning the fluid, and wherein forming the layer comprising the pharmaceutically active composition comprises removing material deposited with the fluid from the substrate.

20. A method as in claim 19, wherein manipulating the layer about the elongated dimension comprises folding at least a portion of the layer across the elongated dimension such that a first portion of a surface of the layer is folded onto a second portion of the same surface.

21. A method as in claim 19, wherein manipulating the layer about the elongated dimension comprises rolling at least a portion of the layer around an axis parallel to the elongated dimension.

22. A method as in claim 19, wherein the ingestible pharmaceutical product comprises a tablet.

23. A method as in claim 19, wherein the pharmaceutically active composition comprises an amorphous composition.

24. A method as in claim 19, wherein the layer has an average thickness of less than about 1 mm.

25. A method as in claim 19, wherein the layer comprises polyethylene glycol.

26. A method as in claim 19, wherein bonding adjacent portions of the layer into a unitary structure comprises applying a compressive force to bond adjacent portions of the layer into the unitary structure.

27. A method as in claim 19, wherein the layer is a free standing layer.

28. A method as in claim 19, wherein the pharmaceutically active composition extends through the layer such that a first surface and a second surface, opposite the first surface, contain the pharmaceutically active composition.

29. A method as in claim 19, comprising combining an excipient with the fluid used to form the layer.

30. A method as in claim 19, wherein the electrospun layer comprises at least one polymeric pharmaceutical excipient.

31. A method as in claim 19, wherein the electrospun layer comprises at least one active pharmaceutical ingredient.

32. A method for manufacturing an article comprising an ingestible pharmaceutical product or a precursor thereof, comprising:

depositing a fluid comprising a pharmaceutically active composition on a substrate;

forming a layer comprising the pharmaceutically active composition, the layer having an elongated dimension;

manipulating the layer about its elongated dimension to form the article, wherein an average thickness of the article is at least about two times an average thickness of portions of the layer used to form the article; and bonding adjacent portions of the layer into a unitary structure, wherein depositing the fluid comprising the pharmaceutically active composition comprises electro spinning a second fluid substantially free of the pharmaceutically active composition while, simultaneously, electro spraying the fluid comprising the pharmaceutically active composition, and wherein forming the layer comprising the pharmaceutically active composition comprises removing material deposited with the fluid from the substrate.

33. A method as in claim 32, wherein manipulating the layer about the elongated dimension comprises folding at least a portion of the layer across the elongated dimension such that a first portion of a surface of the layer is folded onto a second portion of the same surface.

34. A method as in claim 32, wherein manipulating the layer about the elongated dimension comprises rolling at least a portion of the layer around an axis parallel to the elongated dimension.

35. A method as in claim 32, wherein the ingestible pharmaceutical product comprises a tablet.

36. A method as in claim 32, wherein the pharmaceutically active composition comprises an amorphous composition.

37. A method as in claim 32, wherein the layer comprises polyethylene glycol.

38. A method as in claim 32, wherein bonding adjacent portions of the layer into a unitary structure comprises applying a compressive force to bond adjacent portions of the layer into the unitary structure.

39. A method as in claim 32, wherein the layer is a free standing layer.

40. A method as in claim 32, comprising combining an excipient with the fluid used to form the layer.

41. A method as in claim 32, wherein the electrospun layer comprises at least one polymeric pharmaceutical excipient.

42. A method for manufacturing an article comprising an ingestible pharmaceutical product or a precursor thereof, comprising:
  depositing a fluid comprising a pharmaceutically active composition on a substrate;
  forming a layer comprising the pharmaceutically active composition, the layer having an elongated dimension;
  manipulating the layer about its elongated dimension to form the article, wherein an average thickness of the article is at least about two times an average thickness of portions of the layer used to form the article; and
  bonding adjacent portions of the layer into a unitary structure,
  wherein depositing the fluid comprising the pharmaceutically active composition comprises spin coating the fluid, and
  wherein forming the layer comprising the pharmaceutically active composition comprises removing material deposited with the fluid from the substrate.

* * * * *